United States Patent [19]

Jadhav

[11] Patent Number: 5,491,149

[45] Date of Patent: Feb. 13, 1996

[54] DIHYDROXYPROPYLAMINE CONTAINING RETROVIRAL PROTEASE INHIBITORS

[75] Inventor: Prabhakar K. Jadhav, Wilmington, Del.

[73] Assignee: The Du Pont Merck Pharmaceutical Company, Wilmington, Del.

[21] Appl. No.: 296,998

[22] Filed: Aug. 26, 1994

Related U.S. Application Data

[63] Continuation-in-part of Ser. No. 760,519, Sep. 16, 1991, abandoned.

[51] Int. Cl.$^6$ .................... C07D 217/12; C07D 401/08; A61K 31/47
[52] U.S. Cl. .................... 514/307; 546/146; 546/147; 546/194; 546/198; 546/199; 546/207; 546/225; 546/227; 546/281; 548/159; 548/306.1; 548/527; 548/530; 548/531; 540/596; 540/597; 540/602; 540/610; 514/212; 514/318; 514/321; 514/322; 514/330; 514/343; 514/367; 514/394; 514/423; 514/326
[58] Field of Search .................... 546/146, 147, 546/194, 193, 199, 207, 225, 227, 281; 514/307, 212, 318, 321, 322, 326, 330, 343, 367, 397, 423; 548/159, 306.1, 527, 530, 531; 540/596, 597, 602, 610

[56] References Cited

U.S. PATENT DOCUMENTS 5,294,720  3/1994  Jadhav et al. .................... 546/265

FOREIGN PATENT DOCUMENTS

| 2026382 | 3/1991 | Canada. |
| 346847 | 12/1989 | European Pat. Off.. |
| 386611 | 9/1990 | European Pat. Off.. |
| 402646 | 12/1990 | European Pat. Off.. |
| 434365 | 6/1991 | European Pat. Off.. |

*Primary Examiner*—C. Warren Ivy
*Assistant Examiner*—Zinna N. Davis
*Attorney, Agent, or Firm*—Karen H. Kondrad; Gerald L. Boudreaux

[57] ABSTRACT

This invention relates to substituted dihydroxypropylamines, a process to prepare intermediates useful for the synthesis of these compounds, compositions comprising such compounds, and a method of treating retroviral infection.

42 Claims, No Drawings

DIHYDROXYPROPYLAMINE CONTAINING RETROVIRAL PROTEASE INHIBITORS

CROSS-REFERENCE TO EARLIER FILED APPLICATIONS

This application is a continuation-in-part of U.S. patent application Ser. No. 07/760519 filed Sep. 16, 1991, now abandoned. The disclosure of this earlier filed application is hereby incorporated herein by reference.

FIELD OF THE INVENTION

This invention relates to substituted dihydroxypropylamines, a process to prepare intermediates useful for the synthesis of these compounds, compositions comprising such compounds and a method of treating viral infection.

BACKGROUND OF THE INVENTION

Current treatments for viral diseases usually involve administration of compounds that inhibit viral DNA synthesis. Current treatments for AIDS (Dagani, *Chem. Eng. News*, Nov. 23, 1987 pp. 41–49) involve administration of compounds such as 2',3'-dideoxycytidine, trisodium phosphonoformate, ammonium 21-tungsto-9-antimoniate, 1-b-D-ribofuranoxyl-1,2,4-triazole-3-carboxamide, 3'-azido-3'-deoxythymidine, and adriamycin that inhibit viral DNA synthesis; compounds such as AL-721 and polymannoacetate which may prevent HIV from penetrating the host cell; and compounds which treat the opportunistic infections caused by the immunosupression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. However, no therapeutically useful renin protease inhibitors have been developed, due to problems of oral availability and in vivo stability.

The genomes of retroviruses encode a protease that is responsible for the proteolytic processing of one or more polyprotein precursors such as the pol and gag gene products. See Wellink, *Arch. Virol.* 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford, *J. Virol.* 53, 899 (1985); Katoh et al., *Virology* 145 280 (1985). Therefore, retroviral protease inhibition provides an attractive possible target for antiviral therapy. See Mitsuya, *Nature* 325 775 (1987).

Moore, *Biochem. Biophys. Res. Commun.*, 159 420 (1989) discloses peptidyl inhibitors of HIV protease. Erickson, European Patent Application No. WO 89/10752, discloses derivatives of peptides which are inhibitors of HIV protease. Kemf, European Patent Application No. 90109319.5, discloses derivatives of peptides which are inhibitors of HIV protease. Also Handa, European Patent Application No. 89110717.9 discloses aminoacid derivatives as inhibitors of HIV protease. Jadhav, U.S. patent application Ser. No. 07/531,971, filed Jun. 1, 1990 (now abandoned), discloses inhibitors of HIV protease.

EP 402 646 discloses retroviral protease inhibiting compounds of the formula: A-X-B where A and B are independently substituted amino, functionalized alkyl, functionalized acyl, functionalized heterocyclic or functionalized (heterocyclic)alkyl and X is a linking group.

The ability to inhibit a viral protease provides a method for blocking viral replication and therefore a treatment for diseases, and AIDS in particular, that may have fewer side effects and be more efficacious when compared to current treatments. The topic of this patent application is substituted dihydroxypropylamine containing peptide derivatives, which compounds are capable of inhibiting viral protease and which compounds serve as a means of combating viral diseases such as AIDS. The substituted dihydroxypropylamine containing peptide derivatives of this invention provide significant improvements over protease inhibitors that are known in the art. A large number of compounds have been reported to be renin inhibitors, but have suffered from lack of adequate bio-availability and are thus not useful as therapeutic agents. This poor activity has been ascribed to the unusually high molecular weight of renin inhibitors, to inadequate solubility properties, and to the presence of a number of peptide bonds, which are vulnerable to cleavage by mammalian proteases. Retroviral proteases, HIV protease in particular, is capable of cleaving phenylalanine-proline or tyrosine-proline peptide bonds. However, phenylalanine-proline or tyrosine-proline peptide bonds are not susceptible to cleavage by mammalian proteases. The dihydroxypropylamine containing derivatives described herein have a distinct advantage in this regard, in that many of them are derivatives of dipeptide isosteres of phenylalanine-proline or tyrosine-proline. This feature makes them highly specific inhibitors HIV protease. The compounds of this invention do not inhibit enzymes such as renin or pepsin; nor are they cleaved by chymotrypsin. The structure-activity requirements of HIV protease inhibitors differ from those of renin inhibitors suggesting that HIV protease inhibitors may not be inhibitors of human renin.

Other HIV protease inhibitors have been reported, but to date very few have shown activity against viral replication in human cells. This lack of cellular activity is probably due in part to the factors discussed above for renin inhibitors. Unlike other HIV protease inhibitors, the dihydroxypropylamine containing peptide derivatives disclosed herein show potent inhibition of viral replication in human cells. The compounds of this invention, in addition to basic nitrogens, contain a highly hydrophilic diol unit which imparts favorable physical properties such as solubility in common organic and aqueous media. These physical characteristics are important in improving the bioavailability of HIV protease inhibitors.

Another aspect of the present invention is a process for the preparation of 1,2-diols. The 1,2-diol unit is one of the most ubiquitous funtional groups in nature, and consequently a wealth of methods leading to its synthesis have been developed. Foremost in this arsenal are the catalytic osmylation of olefins (Wai et al., J. Am. Chem. Soc. 1989, 111, 1123), ring opening of epoxides (Behrens and Sharpless, J. Org. Chem., 1985, 50, 5696), reduction or alkylation of a-hydroxy/alkoxy carbonyls (Davis et al., J. Org. Chem., 1989, 54, 2021). Common to all of these approaches is the preexistence of the central carbon-carbon bond of the diol function. Methods that lead directly to a 1,2-diol via formation of this bond are less common and include the reaction of an a-alkoxy anion (Cohen and Lin, J. Am. Chem. Soc., 1984, 106, 1130), with a carbonyl and the reductive coupling of two carbonyls (ie., pinacol coupling). Pons and Santelli, Tetrahedron, 1988, 44, 4295.

Of all these methods, pinacol coupling is conceptually one of the simplest methods for the synthesis of 1,2-diols. Consequently, a number of methods have been developed which utilize this reaction for the preparation of these compounds. For example, McMurry et al. report the preparation of a 1,2-diol by pinacol coupling of a dialdehyde in the presence of $TiCl_3$(dimethoxyethane)$_2$/Zn-Cu in dimethoxyethane. McMurray et al., Tetrahedron Lett., 1989, 30, 1173. In a recent review article, Pons and Santelli describe many other methods leading to 1,2-diols which rely on low valent titanium complexes. Pons and Santelli, Tetrahedron, 1988, 44, 4295. Freudenberger et al. disclose a method which utilizes a vanadium (II) complex, $[V_2Cl_3(THF)_6]_2[Zn_2Cl_6]$ to couple aldehydes. Freudenberger et al., J. Am. Chem. Soc., 1989, 111, 8014. Finally an improved method for the preparation of 1,2-diols which utilizes the catalyst of Freudenberger et al. has been disclosed. Jadhav, see U.S. Pat. No. 5,294,720.

While these methods are generally useful for the preparation of 1,2-diols, only Jadhav, U.S. patent application Ser. No. 07/531,971, filed Jun. 1, 1990 teaches how amino moieties can be incorporated into the diols. There is a need for other processes capable of providing such diols. It is an object of the present invention to provide such a process. In addition, the process of the present invention is capable of providing stereochemically pure diols containing at least three contiguous chiral centers. In these respects, the current invention is an improvement over the prior art.

SUMMARY OF THE INVENTION

This invention provides novel substituted dihydroxypropylamines, and derivatives thereof, having the basic formula as set forth in formula (I) described below. The compounds according to the invention inhibit the HIV protease and thereby inhibit HIV replication. The compounds have been shown to decrease HIV viral yield and to decrease multiplicity of the virus in human T-cells in vitro.

In one aspect, the present invention provides substituted dihydroxypropylamines of formula (I), and derivatives thereof.

In another aspect, the present invention provides pharmaceutical compositions containing the compounds of formula (I), and derivatives thereof, and a pharmaceutically acceptable carrier.

In a further aspect, the present invention provides methods of using such compounds and compositions for the inhibition of HIV in a sample containing HIV, and using such compounds and compositions for the treatment of HIV viral infections in a patient.

DETAILED DESCRIPTION OF THE INVENTION

The present invention also includes methods of inhibiting HIV or treating HIV infection by administering a compound of formula (I), or derivatives thereof, in combination with one or more second therapeutic agents selected from other inhibitors of HIV and/or therapeutic agents for the treatment of HIV-mediated disease conditions.

Also included in the present invention are pharmaceutical kits comprising one or more containers containing pharmaceutical dosage units comprising a compound of formula (I), or derivaties thereof, for the treatment of HIV infection.

There is provided by this invention a compound of the formula:

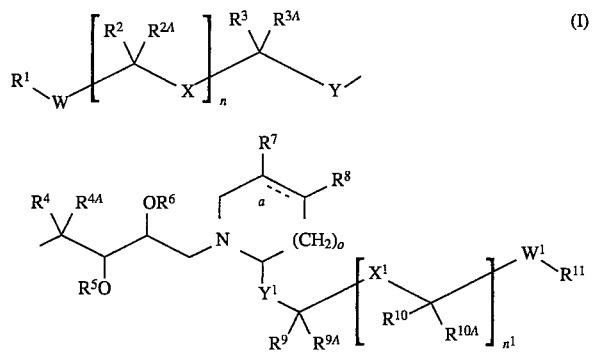

or a pharmaceutically acceptable salt, prodrug, chiral, diastereomeric or racemic form thereof wherein:

$R^1, R^2, R^3, R^4, R^7, R^8, R^9, R^{10}$, and $R^{11}$ are independently selected from the following groups:

hydrogen;

$C_1$–$C_8$ alkyl substituted with 0–3 $R^{12}$;

$C_2$–$C_8$ alkenyl substituted with 0–3 $R^{12}$;

$C_3$–$C_8$ alkynyl substituted with 0–3 $R^{12}$;

$C_3$–$C_8$ cycloalkyl substituted with 0–3 $R^{12}$;

$C_6$–$C_{10}$ bicycloalkyl substituted with 0–3 $R^{12}$;

aryl substituted with 0–3 $R^{13}$;

a $C_6$–$C_{14}$ carbocyclic residue substituted with 0–3 $R^{13}$;

a heterocyclic ring system substituted with 0–2 $R^{13}$, composed of 5 to 10 atoms including at least one nitrogen, oxygen or sulfur atom;

additionally, $R^7$ and $R^8$ may join together to form a saturated or unsaturated hydrocarbon ring system substituted with 0–3 $R^{12}$, or a heterocyclic ring system substituted with 0–2 $R^{13}$, said heterocyclic ring system being composed of 5 to 10 atoms including at least one nitrogen, oxygen, or sulfur atom;

$R^{2A}, R^{3A}, R^{4A}, R^{9A}$, and $R^{10A}$ are independently selected from the following groups:

hydrogen;

$C_1$–$C_4$ alkyl substituted with halogen or $C_1$–$C_2$ alkoxy;

benzyl substituted with halogen or $C_1$–$C_2$ alkoxy;

$R^5$ and $R^6$ are independently selected from the following groups:

hydrogen;

$C_1$–$C_6$ alkoxycarbonyl;

$C_1$–$C_6$ alkylcarbonyl;

benzoyl;

phenoxycarbonyl; or phenylaminocarbonyl; wherein said alkyl residues are substituted with 0–3 $R^{12}$, and said aryl residues are substituted with 0–3 $R^{13}$; or any other group that, when administered to a mammalian subject, cleaves to form the original diol in which $R^5$ and $R^6$ are hydrogen;

$R^{12}$ is selected from one or more of the following:

keto, halogen, cyano, , —$NR^{14}R^{15}$, —$CO_2R^{14}$, —$OC(=O)R^{15}$,

—OR$^{14}$, C$_2$–C$_6$ alkoxyalkyl, —S(O)$_m$R$^{14}$, —NHC(=NH)NHR$^{14}$,
—C(=NH)NHR$^{14}$, —C(=O)NR$^{14}$R$^{15}$,
—NR$^{15}$C(=O)R$^{15}$,
—NR$^{15}$C(=O)OR$^{15}$, —OC(=O)NR$^{14}$R$^{15}$,
—NR$^{14}$C(=O)NR$^{14}$R$^{15}$,
—NR$^{15}$SO$_2$NR$^{14}$R$^{15}$, —NR$^{15}$SO$_2$R$^{14}$,
—SO$_2$NR$^{14}$R$^{15}$, C$_1$–C$_4$ alkyl C$_2$–C$_4$ alkenyl, C$_3$–C$_6$ cycloalkyl, C$_3$–C$_6$ cycloalkylmethyl;

a C$_5$–C$_{14}$ carbocyclic residue substituted with 0–3 R$^{13}$;

aryl substituted with 0–3 R$^{13}$;

or a heterocyclic ring system substituted with 0–2 R$^{13}$, composed of 5 to 10 atoms including at least one nitrogen, oxygen or sulfur atom.

R$^{13}$, when a substituent on carbon, is selected from one or more of the following:

phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C$_{10}$ arylalkyl, alkoxy, —NR$^{14}$R$^{15}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{14}$, —SO$_2$NR$^{14}$R$^{15}$, —NHSO$_2$R$^{15}$;

or R$^{13}$ may be a 3- or 4-carbon chain attached to adjacent carbons on the ring to form a fused 5- or 6-membered ring, said 5- or 6-membered ring being optionally substituted on the aliphatic carbons with halogen, C$_1$–C$_4$ alkyl, C$_1$–C$_4$ alkoxy, hydroxy, or NR$^{14}$R$^{15}$; or, when R$^{13}$ is attached to a saturated carbon atom it may be carbonyl or thiocarbonyl;

and R$^{13}$, when a substituent on nitrogen, is selected from one or more of the following:

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —NR$^{14}$R$^{15}$, C$_2$–C$_6$ alkoxyalkyl, C$_1$–C$_4$ haloalkyl, C$_1$–C$_4$ alkoxycarbonyl, C$_1$–C$_4$ alkylcarbonyloxy, C$_1$–C$_4$ alkylcarbonyl;

R$^{14}$ is H, phenyl, benzyl or C$_1$–C$_6$ alkyl;

R$^{15}$ is H or C$_1$–C$_4$ alkyl;

or R$^{14}$ and R$^{15}$ can join to form (CH$_2$)$_4$, (CH$_2$)$_5$, (CH$_2$CH$_2$N(R$^{16}$)CH$_2$CH$_2$), or (CH$_2$CH$_2$OCH$_2$CH$_2$);

R$^{16}$ is H or CH$_3$;

a is a double or single bond;

m is 0, 1 or 2;

n and n$^1$ are independently 0 or 1;

o is 0, 1, 2 or 3;

W and W$^1$ are independently selected from the following:

—NR$^{16}$C(=Q)NR$^{16}$—;
—C(=Q)NR$^{16}$—;
—C(=Q)O—;
—NR$^{16}$C(=Q)O—;
—OC(=Q)NR$^{16}$—;
—NR$^{16}$C(=Q)—;
—C(=Q)—;
—C(=Q)CH—;
—NR$^{16}$SO$_2$NR$^{16}$—
—NR$^{16}$SO$_2$—
—SO$_2$NR$^{16}$—
—SO$_2$—;
—QCH$_2$—;
—Q—;
—(CH$_2$)$_p$NR$^{16}$—;
—CH$_2$CH$_2$—;
—CH=CH—;
—CH(OH)CH(OH)—;
—CH(OH)CH$_2$—;
—CH$_2$CH(OH)—;
—CH(OH)—;
—NH—NH—;
—C(=O)NH—NH—;
—C(Cl)=N—;
—C(—OR$^{16}$)=N—;
—C(—NR$^{16}$R$^{17}$)=N—;
—OP(=O)(Q$^1$R$^{16}$)O—;
—P(=O)(Q$^1$R$^{16}$)O—;
—SO$_2$NHC(=O)NH—; or
a direct bond;

X and X$^1$ are independently selected from the following:
—C(=Q)NR$^{16}$—;
—C(=Q)O—;
—C(=Q)—;
—CH$_2$C(=Q)—;
—CH$_2$C(=Q)CH$_2$—;
—C(=Q)CH$_2$—;
—SO$_2$NR$^{16}$—
—SO$_2$—;
—CH$_2$QCH$_2$—;
—CH$_2$Q—;
—CH$_2$NR$^{16}$—;
—CH$_2$CH$_2$—;
—CH=CH—;
—CH(OH)CH(OH)—;
—CH(OH)CH$_2$—;
—CH$_2$CH(OH)—;
—CH(OH)—;
—C(=O)NH—NH—;
—C(—OR$^{16}$)=N—;
—C(—NR$^{16}$R$^{17}$)=N—;
—C(L)=N—;

Y and Y$^1$ are independently selected from the following:
—C(=Q)NR$^{16}$—;
—(CH$_2$)$_p$C(=Q)NR$^{16}$—;
—SO$_2$NR$^{16}$—;
—CH$_2$NR$^{16}$—;
—C(L)=N—;
—C(—OR$^{16}$)=N—;
—C(—NR$^{16}$R$^{17}$)=N—;
—NR12C(=O)NR$^{16}$—;
—(CH$_2$)$_p$NR12C(=O)NR$^{16}$—;
—OC(=O)NR$^{16}$—;
—(CH$_2$)$_p$OC(=O)NR$^{16}$—;

R$^{17}$ is H, benzyl or C$_1$–C$_4$ alkyl;

R$^{18}$ is H or C$_1$–C$_4$ alkyl;

L is Cl or Br;

p is 1 or 2;

Q is selected from oxygen or sulfur; and

Q$^1$ is selected from oxygen, sulfur, NR$^{14}$ or a direct bond.

There is also provided by the present invention a process for the preparation of compounds of formulae:

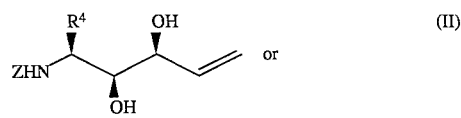

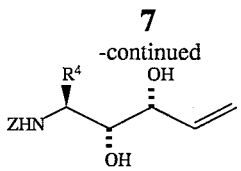

(III)

comprising the steps of (a) reacting a borane reagent of formula:

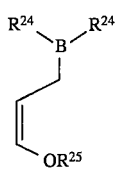

(IV)

with an aldehyde of formula:

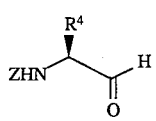

(V)

in an aprotic solvent,
wherein:
$R^4$ is as defined above;
$R^{24}$ is (+)-3-caranyl, (−)-3-caranyl, (+)-2-caranyl or (−)-2-caranyl, (−)-3-pinanyl, (+)-3-pinanyl;
$R^{25}$ is $CH_3$, $CH_{2OCH3}$, $CH_2OCH_2CH_2Si(CH_3)_3$ or $CH_2OC(CH_3)_3$; and
Z is any suitable nitrogen protecting group.

The present invention also provides methods for the treatment of viral infections comprising administering to a host in need of such treatment a pharmaceutically effective antiviral amount of a compound of formula (I):

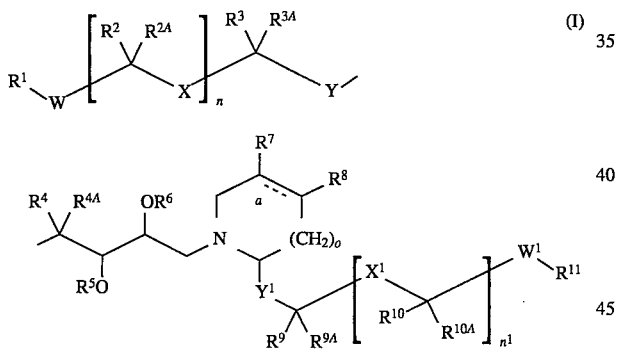

(I)

wherein:
$R^1$, $R^2$, $R^3$, $R^4$, $R^7$, $R^8$, $R^9$, $R^{10}$, and $R^{11}$ are independently selected from the following groups:
hydrogen;
$C_1$–$C_8$ alkyl substituted with 0–3 $R^{12}$;
$C_2$–$C_8$ alkenyl substituted with 0–3 $R^{12}$;
$C_3$–$C_8$ alkynyl substituted with 0–3 $R^{12}$;
$C_3$–$C_8$ cycloalkyl substituted with 0–3 $R^{12}$;
$C_6$–$C_{10}$ bicycloalkyl substituted with 0–3 $R^{12}$;
aryl substituted with 0–3 $R^{13}$;
a $C_6$–$C_{14}$ carbocyclic residue substituted with 0–3 $R^{13}$;
a heterocyclic ring system substituted with 0–2 $R^{13}$, composed of 5 to 10 atoms including at least one nitrogen, oxygen or sulfur atom;
additionally, $R^7$ and $R^8$ may join together to form a saturated or unsaturated hydrocarbon ring system substituted with 0–3 $R^{12}$, or a heterocyclic ring system substituted with 0–2 $R^{13}$, said heterocyclic ring system being composed of 5 to 10 atoms including at least one nitrogen, oxygen, or sulfur atom;

$R^{2A}$, $R^{3A}$, $R^{4A}$, $R^{9A}$, and $R^{10A}$ are independently selected from the following groups:
hydrogen;
$C_1$–$C_4$ alkyl substituted with halogen or $C_1$–$C_2$ alkoxy;
benzyl substituted with halogen or $C_1$–$C_2$ alkoxy;

$R^5$ and $R^6$ are independently selected from the following groups:
hydrogen;
$C_1$–$C_6$ alkoxycarbonyl;
$C_1$–$C_6$ alkylcarbonyl;
benzoyl;
phenoxycarbonyl; or
phenylaminocarbonyl; wherein said alkyl residues are substituted with 0–3 $R^{12}$, and said aryl residues are substituted with 0–3 $R^{13}$; or any other group that, when administered to a mammalian subject, cleaves to form the original diol in which $R^5$ and $R^6$ are hydrogen;

$R^{12}$ is selected from one or more of the following:
keto, halogen, cyano, $-NR^{14}R^{15}$, $-CO_2R^{14}$, $-OC(=O)R^{15}$,
$-OR^{14}$, $C_2$–$C_6$ alkoxyalkyl, $-S(O)_mR^{14}$,
$-NHC(=NH)NHR^{14}$,
$-C(=NH)NHR^{14}$, $-C(=O)NR^{14}R^{15}$,
$-NR^{15}C(=O)R^{15}$,
$-NR^{15}C(=O)OR^{15}$, $-OC(=O)NR^{14}R^{15}$,
$-NR^{14}C(=O)NR^{14}R^{15}$,
$-NR^{15}SO_2NR^{14}R^{15}$, $-NR^{15}SO_2R^{14}$,
$-SO_2NR^{14}R^{15}$, $C_1$–$C_4$ alkyl,
$C_2$–$C_4$ alkenyl, $C_3$–$C_6$ cycloalkyl, $C_3$–$C_6$ cycloalkylmethyl;
a $C_5$–$C_{14}$ carbocyclic residue substituted with 0–3 $R^{13}$;
aryl substituted with 0–3 $R^{13}$;
or a heterocyclic ring system substituted with 0–2 $R^{13}$, composed of 5 to 10 atoms including at least one nitrogen, oxygen or sulfur atom.

$R^{13}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, alkoxy, $-NR^{14}R^{15}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, $-S(O)_mR^{14}$, $-SO_2NR^{14}R^{15}$, $-NHSO_2R^{15}$; or $R^{13}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or $NR^{14}R^{15}$; or, when $R^{13}$ is attached to a saturated carbon atom it may be carbonyl or thiocarbonyl;

and $R^{13}$, when a substituent on nitrogen, is selected from one or more of the following:
phenyl, benzyl, phenethyl, hydroxy, $C_1$–$C_4$ hydroxyalkyl, $C_1$–$C_4$ alkoxy, , $C_1$–$C_4$ alkyl, $C_3$–$C_6$ cycloalkyl, $C_3$–$C_6$ cycloalkylmethyl, $-NR^{14}R^{15}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl;

$R^{14}$ is H, phenyl, benzyl or $C_1$–$C_6$ alkyl;

$R^{15}$ is H or $C_1$–$C_4$ alkyl;

or $R^{14}$ and $R^{15}$ can join to form $(CH_2)_4$, $(CH_2)_5$, $(CH_2CH_2N(R^{16})CH_2CH_2)$, or $(CH_2CH_2OCH_2CH_2)$;

$R^{16}$ is H or $CH_3$;

a is a double or single bond;

m is 0, 1 or 2;

n and $n^1$ are independently 0 or 1;

o is 0, 1, 2 or 3;

W and $W^1$ are independently selected from the following:
—$NR^{16}C(=Q)NR^{16}$—;
—$C(=Q)NR^{16}$—;
—$C(=Q)O$—;
—$NR^{16}C(=Q)O$—;
—$OC(=Q)NR^{16}$—;
—$NR^{16}C(=Q)$—;
—$C(=Q)$—;
—$C(=Q)CH_2$—;
—$NR^{16}SO_2NR^{16}$—
—$NR^{16}SO_2$—
—$SO_2NR^{16}$—
—$SO_2$—;
—$QCH_2$—;
—$Q$—;
$(CH_2)_pNR^{16}$—;
—$CH_2CH_2$—;
—$CH=CH$—;
—$CH(OH)CH(OH)$—;
—$CH(OH)CH_2$—;
—$CH_2CH(OH)$—;
—$CH(OH)$—;
—$NH$—$NH$—;
—$C(=O)NH$—$NH$—;
—$C(Cl)=N$—;
—$C(-OR^{16})=N$—;
—$C(-NR^{16}R^{17})=N$—;
—$OP(=O)(Q^1R^{16})O$—;
—$P(=O)(Q^1R^{16})O$—;
—$SO_2NHC(=O)NH$—; or
a direct bond;

X and $X^1$ are independently selected from the following:
—$C(=Q)NR^{16}$—;
—$C(=Q)O$—;
—$C(=Q)$—;
—$CH_2C(=Q)$—;
—$CH_2C(=Q)CH_2$—;
—$C(=Q)CH_2$—;
—$SO_2NR^{16}$—
—$SO_2$—;
—$CH_2QCH_2$—;
—$CH_2Q$—;
—$CH_2NR^{16}$—;
—$CH_2CH_2$—;
—$CH=CH$—;
—$CH(OH)CH(OH)$—;
—$CH(OH)CH_2$—;
—$CH_2CH(OH)$—;
—$CH(OH)$—;
—$C(=O)NH$—$NH$—;
—$C(-OR^{16})=N$—;
—$C(-NR^{16}R^{17})=N$—;
—$C(L)=N$—;

Y and $Y^1$ are independently selected from the following:
—$C(=Q)NR^{16}$—;
—$(CH_2)_pC(=Q)NR^{16}$—;
—$SO_2NR^{16}$—;
—$CH_2NR^{16}$—;
—$C(L)=N$—;
—$C(-OR^{16})=N$—;
—$C(-NR^{16}R^{17})=N$—;

—$NR12C(=O)NR^{16}$—;
—$(CH_2)_pNR12C(=O)NR^{16}$—;
—$OC(=O)NR^{16}$—;
—$(CH_2)_pOC(=O)NR^{16}$—;

$R^{17}$ is H, benzyl or $C_1$-$C_4$ alkyl;

$R^{18}$ is H or $C_1$-$C_4$ alkyl;

L is Cl or Br;

p is 1 or 2;

Q is selected from oxygen or sulfur; and $Q^1$ is selected from oxygen, sulfur, $NR^{14}$ or a direct bond; and pharmaceutically acceptable salts and prodrugs thereof.

Preferred Embodiments

Compounds preferred for use in the method of this invention include those compounds above wherein:

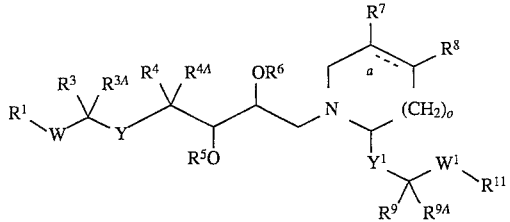

wherein:

$R^1$ and $R^{11}$ are independently selected from the following:
hydrogen;
$C_1$-$C_6$ alkyl substituted with 0–2 $R^{12}$;
$C_2$-$C_4$ alkenyl substituted with 0–2 $R^{12}$;
$C_3$-$C_6$ cycloalkyl substituted with 0–2 $R^{12}$;
$C_6$-$C_{10}$ bicycloalkyl substituted with 0–2 $R^{12}$; p2 aryl substituted with 0–3 $R^{13}$;
a $C_6$-$C_{14}$ carbocyclic residue substituted with 0–2 $R^{13}$;
a heterocyclic ring system substituted with 0–2 $R^{13}$, composed of 5 to 10 atoms including at least one nitrogen, oxygen or sulfur atom;

$R^3$ and $R^9$ are independently selected from the following groups:
hydrogen;
$C_1$-$C_5$ alkyl substituted with 0–2 $R^{12}$;
$C_2$-$C_4$ alkenyl substituted with 0–2 $R^{12}$;
$C_3$-$C_6$ cycloalkyl substituted with 0–2 $R^{12}$;
with the proviso that the total number of non-hydrogen atoms comprising $R^3$ is less than or equal to 6, and the total number of non-hydrogen atoms comprising $R^9$ is less than or equal to 6;

$R^4$ is selected from the following groups:
hydrogen;
$C_1$-$C_5$ alkyl substituted with 0–3 $R^{12}$;
$C_2$-$C_4$ alkenyl substituted with 0–2 $R^{12}$;
$C_3$-$C_6$ cycloalkyl substituted with 0–2 $R^{12}$;
$C_6$-$C_{10}$ bicycloalkyl substituted with 0–3 $R^{12}$;
a $C_6$-$C_{14}$ carbocyclic residue substituted with 0–3 $R^{12}$;
a heterocyclic ring system substituted with 0–2 $R^{13}$, composed of 5 to 10 atoms including at least one nitrogen, oxygen or sulfur atom;

$R^{3A}$ and $R^{4A}$ are independently selected from the following groups:
hydrogen;
$C_1$-$C_2$ alkyl;

$R^5$ and $R^6$ are independently selected from the following groups:
hydrogen; or any other group that, when administered to a mammalian subject, cleaves to form the original diol in which $R^5$ and $R^6$ are hydrogen;

$R^7$ and $R^8$ may join together to form a saturated or unsaturated hydrocarbon ring structure or a heterocycle, or are independently selected from the following groups:
hydrogen;
$C_1$–$C_2$ alkyl, substituted with halogen or $C_1$–$C_2$ alkoxy;

$R^{12}$ is selected from one or more of the following:
keto, halogen, cyano, —$NR^{14}R^{15}$, —$CO_2R^{14}$, —$OC(=O)R^{15}$, —$OR^{14}$, $C_2$–$C_6$ alkoxyalkyl, —$S(O)_mR^{14}$, —$NHC(=NH)NHR^{14}$, —$C(=NH)NHR^{14}$, —$C(=O)NR^{14}R^{15}$, —$NR^{15}C(=O)R^{15}$, —$NR^{15}C(=O)OR^{15}$, —$OC(=O)NR^{14}R^{15}$, $NR^{14}C(=O)NR^{14}R^{15}$, —$NR^{15}SO_2NR^{14}R^{15}$, $NR^{15}SO_2R^{14}$, —$SO_2NR^{14}R^{15}$, $C_1$–$C_4$ $C_2$–$C_4$ alkenyl, $C_3$–$C_6$ cycloalkyl, $C_3$–$C_6$ cycloalkylmethyl;
a $C_5$–$C_{14}$ carbocyclic residue substituted with 0–3 $R^{13}$;
aryl substituted with 0–3 $R^{13}$;
or a heterocyclic ring system substituted with 0–2 $R^{13}$, composed of 5 to 10 atoms including at least one nitrogen, oxygen or sulfur atom;

$R^{13}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl alkoxy, —$NR^{14}R^{15}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{14}$, —$SO_2NR^{14}R^{15}$, —$NHSO_2R^{15}$;
or $R^{13}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or $NR^{14}R^{15}$; or, when $R^{13}$ is attached to a saturated carbon atom it may be carbonyl or thiocarbonyl;
and $R^{13}$, when a substituent on nitrogen, is selected from one or more of the following:
benzyl, hydroxy, $C_1$–$C_4$ alkoxy, $C_1$–$C_5$ hydroxyalkyl, $C_1$–$C_4$ alkyl, $C_3$–$C_6$ cycloalkyl, $C_3$–$C_6$ cycloalkylmethyl, $C_1$–$C_4$ alkoxycarbonyl, $C_1$–$C_4$ alkylcarbonyloxy, $C_1$–$C_4$ alkylcarbonyl;

$R^{14}$ is H, benzyl or $C_1$–$C_4$ alkyl;

$R^{15}$ is H or $C_1$–$C_4$ alkyl;

or $R^{13}$ and $R^{14}$ can join to form $(CH_2)_4$, $(CH_2)_5$, $(CH_2CH_2N(R^{16})CH_2CH_2)$, or $(CH_2CH_2OCH_2CH_2)$;

$R^{16}$ is H or $CH_3$;

a is a double or single bond;

m is 0, 1 or 2;

o is 0, 1 or 2;

W and $W^1$ are independently selected from the following:
—$NR^{16}C(=Q)NR^{16}$—;
—$C(=Q)NR^{16}$—;
—$OC(=Q)NR^{16}$—;
—$NR^{16}SO_2NR^{16}$—
—$SO_2NR^{16}$—
—$(CH_2)_pNR^{16}$—;
—$P(=O)(Q^1R^{16})O$—;
—$SO_2NHC(=O)NH$—; or
a direct bond;

Y and $Y^1$ are independently selected from the following:
—$C(=Q)NR^{16}$—; —$NR12C(=O)NR^{16}$—;
—$OC(=O)NR^{16}$—;

$R^{17}$ is H or $C_1$–$C_2$ alkyl;

Q is selected from oxygen or sulfur; and $Q^1$ is selected from oxygen, sulfur, $NR^{14}$ or a bond;

and pharmaceutically acceptable salts and prodrugs thereof.

More preferred compounds of the invention for greater activity and/or ease of synthesis are those compounds from above of structure:

wherein:
$R^1$ and $R^{11}$ are independently selected from the following:
hydrogen;
$C_1$–$C_6$ alkyl substituted with 0–1 $R^{18}$;
$C_2$–$C_4$ alkenyl substituted with 0–1 $R^{18}$;
aryl substituted with 0–1 $R^{20}$;
a heterocyclic ring system, substituted with 0–1 $R^{20}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

wherein $R^{18}$ is chosen from the following group:
keto, halogen, cyano, —$NR^{14}R^{15}$, —$CO_2R^{14}$, —$OC(=O)R^{15}$, —$OR^{14}$, $C_2$–$C_6$ alkoxyalkyl, —$S(O)_mR^{14}$, —$NHC(=NH)NHR^{14}$, —$C(=O)NR^{14}R^{15}$, —$NR^{15}C(=O)R^{15}$, —$NR^{15}C(=O)OR^{15}$, —$OC(=O)NR^{14}R^{15}$, $NR^{14}C(=O)NR^{14}R^{15}$, —$NR^{15}SO_2NR^{14}R^{15}$, —$NR^{15}SO_2R^{14}$, —$SO_2NR^{14}R^{15}$, $C_1$–$C_4$ alkyl, $C_2$–$C_4$ alkenyl, or $C_3$–$C_6$ cycloalkyl;
a $C_5$–$C_{14}$ carbocyclic residue substituted with 0–3 $R^{20}$;
aryl substituted with 0–2 $R^{20}$;
or a heterocyclic ring system substituted with 0–2 $R^{20}$, selected from selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

wherein $R^{20}$, when a substituent on carbon, is selected from the following:
halogen, hydroxy, nitro, cyano, methyl, methoxy, —$NR^{13}R^{14}$, $C_1$–$C_4$ haloalkyl, $C_1$–$C_2$ alkoxycarbonyl, $C_1$–$C_2$ alkylcarbonyloxy, $C_1$–$C_2$ alkylcarbonylamino, —$SO_2NR^{13}R^{14}$, or —$NHSO_2R^{14}$;
and $R^{20}$, when a substituent on nitrogen, is $C_1$–$C_4$ alkyl;

$R^3$ and $R^9$ are independently selected from the following groups:
hydrogen;
$C_1$–$C_5$ alkyl substituted with 0–3 halogen or 0–1 $R^{23}$;
$C_2$–$C_4$ alkenyl substituted with 0–3 halogen or 0–1 $R^{23}$;
$C_3$–$C_6$ cycloalkyl substituted with 0–3 halogen or 0–1 $R^{23}$;

wherein $R^{23}$ is selected from the following groups:
keto, amino, methylamino, dimethylamino, —C(=O)NH$_2$, C(=O)NMe$_2$, —C(=O)NHMe, or C$_3$–C$_5$ cycloalkyl;
with the proviso that the total number of non-hydrogen atoms comprising $R^3$ is less than or equal to 6, and the total number of non-hydrogen atoms comprising $R^9$ is less than or equal to 6;

$R^4$ is selected from the following groups:
hydrogen;
C$_1$–C$_4$ alkyl substituted with 0–3 halogen or 0–3 $R^{26}$;
aryl substituted with 0–1 $R^{26}$;
a heterocyclic ring system, selected from pyridyl, thienyl, indolyl, pyrolyl, piperazyl, N-methylpiperazyl, or imidazolyl, substituted with 0–2 $R^{27}$;

wherein $R^{26}$ is selected from one or more of the following:
keto, halogen, cyano, —NR$^{14}$R$^{15}$, —CO$_2$R$^{14}$, —OC(=O)R$^{15}$, —OR$^{14}$, C$_2$–C$_6$ alkoxyalkyl, —S(O)$_m$R$^{14}$, C$_3$–C$_6$ cycloalkyl, C$_3$–C$_6$ cycloalkylmethyl;
aryl substituted with 0–3 $R^{13}$;
or a heterocyclic ring system, selected from pyridyl, thienyl, pyrolyl, indolyl, piperazyl, N-methylpiperazyl, or imidazolyl, substituted with 0–2 $R^{27}$;

wherein $R^{27}$, when a substituent on carbon, is selected from one or more of the following:
phenyl, benzyl, benzyloxy, halogen, hydroxy, nitro, C$_1$–C$_4$ alkyl, C$_1$–C$_4$ alkoxy, amino, methylamino, dimethylamino, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino;
and $R^{27}$, when a substituent on nitrogen, is C$_1$–C$_4$ alkyl;

$R^{3A}$ and $R^{4A}$ are hydrogen;

$R^5$ and $R^6$ are independently selected from the following groups:
hydrogen, or any other group that, when administered to a mammalian subject, cleaves to form the original diol in which $R^5$ and $R^6$ are hydrogen;

$R^7$ and $R^8$ join together to form a saturated or unsaturated hydrocarbon ring structure;

$R^{14}$ and $R^{15}$ are independently selected from H or C$_1$–C$_2$ alkyl;

m is 0, 1 or 2;
n and n$^1$ are 0;
o is 1;

W and W1 are independently selected from the following:
—NR$^{16}$C(=Q)NR$^{16}$—;
—C(=O)NR$^{16}$—;
—OC(=O)NR$^{16}$—;
—(CH$_2$)$_p$NR$^{16}$—; or
a direct bond;

Y and Y$^1$ are independently selected from the following:
—C(=O)NR$^{16}$—;
—NR12C(=O)NR$^{16}$—;
—OC(=O)NR$^{16}$—;

$R^{16}$ is H or methyl;
Q is selected from oxygen or sulfur;
and pharmaceutically acceptable salts and prodrugs thereof.

More further preferred compounds of the invention are those compounds from above of the structure:

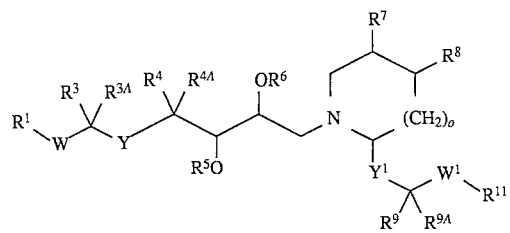

wherein:

$R^1$ is selected from the following:
hydrogen;
C$_1$–C$_3$ alkyl substituted with 0–1 $R^{18}$;
wherein $R^{18}$ is chosen from the following group:
keto, halogen, cyano, or C$_3$–C$_6$ cycloalkyl;
aryl substituted with 0–2 $R^{20}$;
or a heterocyclic ring system substituted with 0–2 $R^{20}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, pyrrolidinyl, tetrahydroquinolinyl, or tetrahydroisoquinolinyl;
wherein $R^{20}$, when a substituent on carbon, is halogen, methyl, or methoxy; and $R^{20}$, when a substituent on nitrogen, is methyl;

$R^3$ is selected from the following groups:
hydrogen;
C$_1$–C$_3$ alkyl optionally substituted with 0–3 halogen or C(=O)NH$_2$;
with the proviso that the total number of non-hydrogen atoms comprising $R^3$ is less than or equal to 6;

$R^9$, $R^{9A}$, and $R^{11}$ are independently selected from C$_1$–C$_2$ alkyl or hydrogen $R^4$ is selected from the following groups:
C$_1$–C$_4$ alkyl substituted with 0–3 halogen or 0–1 $R^{26}$;
wherein $R^{26}$ is selected from the following groups:
C$_3$–C$_6$ cycloalkyl; aryl; or a heterocyclic ring system selected from pyridyl, thienyl, pyrolyl, or indolyl;

$R^{3A}$ and $R^{4A}$ are hydrogen;

$R^5$ and $R^6$ are hydrogen;

$R^7$ and $R^8$ join together to form a saturated or unsaturated 5 or 6 membered hydrocarbon ring structure;

W is selected from the following:
—NR$^{16}$C(=O)NR$^{16}$—;
—C(=O)NR$^{16}$—;
—OC(=O)NR$^{16}$—; or
a direct bond;

W$^1$ is a direct bond;

Y and Y$^1$ are —C(=O)NR$^{16}$—;

$R^{16}$ is H or methyl;

and pharmaceutically acceptable salts and prodrugs thereof.

Most preferred compounds of the invention are those compounds from above of the structure:

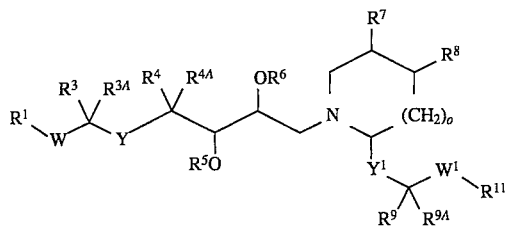

wherein:

R¹ is selected from the following:
  hydrogen;
  $C_1$–$C_2$ alkyl substituted with 0–1 $R^{18}$;
  wherein $R^{18}$ is chosen from the following group:
    aryl substituted with 0–2 $R^{20}$;
    or a heterocyclic ring system substituted with 0–2 $R^{20}$, selected from pyridyl, thienyl, pyrrolyl, pyrazolyl, imidazolyl, tetrazolyl, benzothiophenyl, indolyl, quinolinyl, isoquinolinyl, or benzimidazolyl;
  wherein $R^{20}$, when a substituent on carbon, is halogen, methyl, or methoxy;
  and $R^{20}$, when a substituent on nitrogen, is methyl;

R³ is selected from the following groups:
  $C_1$–$C_3$ alkyl optionally substituted with C(=O)NH₂;
  with the proviso that the total number of non-hydrogen atoms comprising R³ is less than or equal to 6;

$R^9$, $R^{9A}$, and $R^{11}$ are independently selected from methyl or hydrogen R⁴ is selected from the following groups:
  $C_1$–$C_2$ alkyl substituted with 0–3 halogen or 0–1 $R^{26}$;
  wherein $R^{26}$ is selected from the following groups:
    $C_3$–$C_6$ cycloalkyl; aryl; or a heterocyclic ring system selected from pyridyl, thienyl, pyrolyl, or indolyl;

$R^{3A}$ and $R^{4A}$ are hydrogen;

R⁵ and R⁶ are hydrogen;

R⁷ and R⁸ join together to form a saturated or unsaturated 5 or 6 membered hydrocarbon ring structure;

W is selected from the following:
  —NHC(=O)NH—;
  —C(=O)NH—; or
  —OC(=O)NH—;

W¹ is a direct bond;

Y and Y¹ are —C(=O)NH—;

and pharmaceutically acceptable salts and prodrugs thereof.

Specific examples of compounds useful in various embodiments of the invention include compounds of the formula:

a) [3S-[2[1R*(R*),2R*,3S*],3a,4ab,8ab]]-(phenylmethyl)[ 3-amino-1-[[[4-[3-[[(1,1-dimethylethyl)amino]carbonyl]octahydro-2(1H)-isoquinolinyl]-2,3-dihydroxy-1(phenylmethyl)butyl]amino]carbonyl] -3-oxopropyl]carbamate

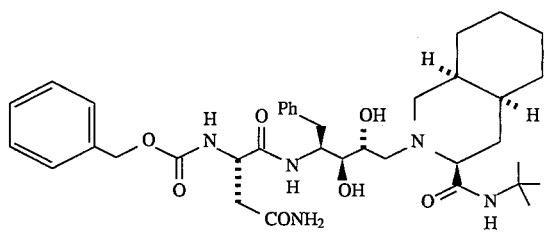

b) [3S-[2[1R*(R*),2R*,3S*],3a,4ab,8b]]-N1-[4-[3-[ [(1,1-dimethylethyl)amino]carbonyl]octahydro-2(1H)-isoquinolinyl] -2,3-dihydroxy-1-(phenylmethyl)butyl]-2-[(2-quinolinylcarbonyl)amino]butanediamide

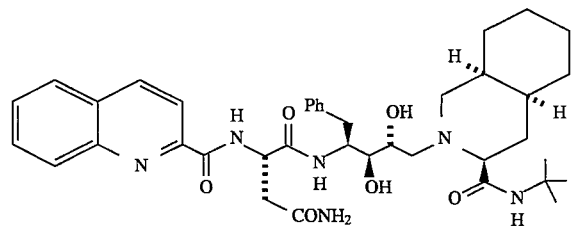

c) [3-[2[1R*(R*),2R*,3S*],3a,4ab,8ab]]-(phenylmethyl)[ 1-[[[4-[3-[[(1,1-dimethylethyl)amino]carbonyl]octahydro- 2(1H)-isoquinolinyl- 2,3-dihydroxy-1-(phenylmethyl)butyl]amino]carbonyl]- 2-methylpropyl]carbamate

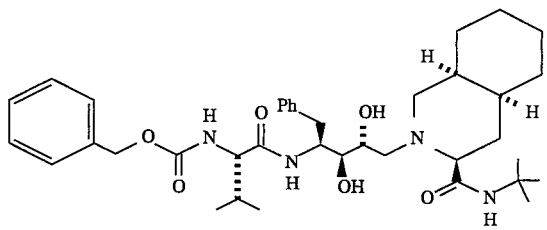

d) [3S-[2[1R*(R*,R*),2R*,3S*],3a,4ab,8ab]]-(phenylmethyl)[ 1-[[[4-[3-[[(1,1-dimethylethyl)amino]carbonyl] octahydro- 2(1H)-isoquinolinyl] -2,3-dihydroxy-1-(phenylmethyl)butyl] amino]carbonyl]-2-methylbutyl] carbamate

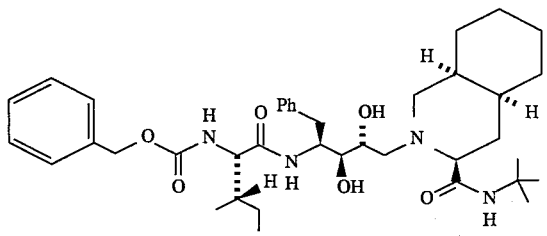

e) [3S-[2[1R*(R*),2S*,3R*],3a,4ab,8ab]]-(phenylmethyl)[ 3-amino-1-[[[4-[3-[[(1,1-dimethylethyl)amino]carbonyl]octahydro-2(1H)-isoquinolinyl]-2,3-dihydroxy-1-(phenylmethyl)butyl] amino]carbonyl] -3-oxopropyl]carbamate

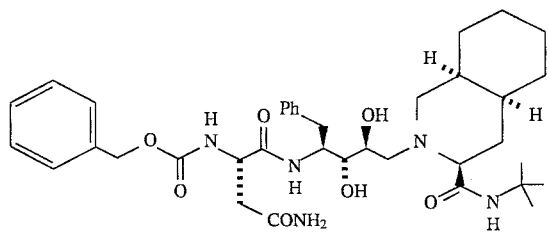

f) [3S-[2[1R*(R*),2S*,3R*],3a,4ab,8ab]]-N1-[4-[3-[ [(1,1-dimethylethyl)amino]carbonyl]octahydro-2(1H)-isoquinolinyl] -2,3-dihydroxy-1-(phenylmethyl)butyl]-2-[(2-quinolinylcarbonyl)amino] butanediamide

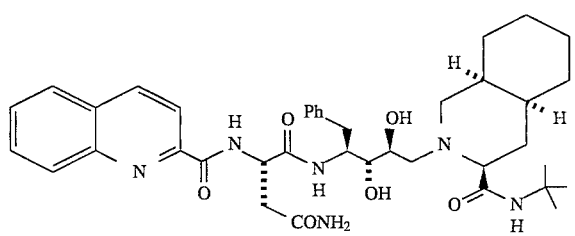

g) [3S-[2[1R*(R*),2R*,3R*],3a,4ab,8ab]]-N1-[4-[3-[ [(1,1-dimethylethyl)amino]carbonyl]octahydro-2(1H)-isoquinolinyl] -2,3-dihydroxy-1-(phenylmethyl)butyl]-2-[(2-quinolinylcarbonyl)amino] butanediamide

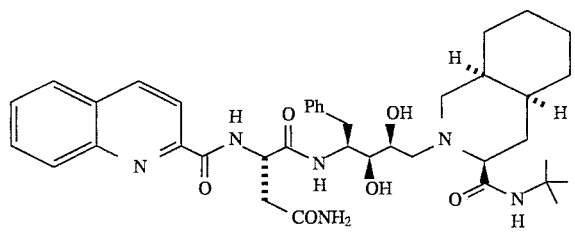

h) [3S-[2[1R*(R*),2S*,3S*],3a,4ab,8ab]]-(phenylmethyl)[ 3-amino-1-[[[4-[3-[[(1,1-dimethylethyl)amino] carbonyl]octahydro- 2(1H)-isoquinolinyl-2,3-dihydroxy-1-(phenylmethyl)butyl] amino]carbonyl] -3-oxopropyl]carbamate

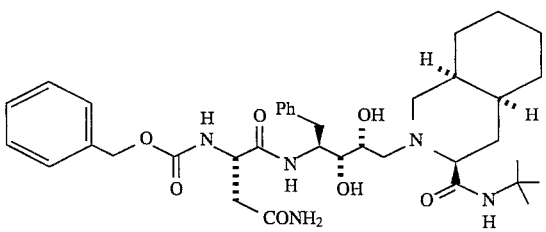

i) [3S-[2[1R*(R*),2S*,3S*],3a,4ab,8ab]]-N1-[4-[3-[ [(1,1-dimethylethyl)amino]carbonyl]octahydro-2(1H)-isoquinolinyl]-2,3-dihydroxy-1-(phenylmethyl)butyl]-2-[(2-quinolinylcarbonyl)amino] butanediamide

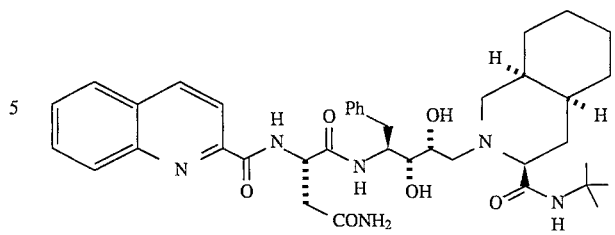

The compounds herein described may have asymmetric centers. All chiral, diastereomeric and racemic forms are included in the present invention. Many geometric isomers of olefins, C=N double bonds, and the like can also be present in the compounds described herein, and all such stable isomers are contemplated in the present invention.

When any variable (for example, $R^1$ through $R^{18}$, $R^{24}$ through $R^{9A}$, m, n, p, Q, W, X, Y, Z, etc.) occurs more than one time in any constituent or in formula (I), its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic.

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or decahydroisoquinolinyl. The term "substituted", as used herein, means that an one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive: isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

The present invention provides compounds of formula (I). These compounds can be prepared via many procedures well known to those skilled in the art of organic synthesis. One of these methods is derivitization of the alcohol moieties of a compound of formula (VI), as shown below.

condensation reaction to from an ester derivative. In the case where L is hydroxy, a coupling reaction can be carried out in the presence of any of the coupling reagents known in the art. Such coupling reagents include, but are not limited to, dicyclohexylcarbodiimide (DCC), 3-ethyl-3'-(dimethylamino)propylcarbodiimide (EDC), bis(2-oxo-3-oxazolidinyl)-phosphinic chloride (BOP-Cl), dipenylphosphoryl azide (DPPA) and the like. In addition $R^5$-L or $R^6$-L can be acid halides or other activated ester derivatives which are useful for the coupling reactions. Acid halide derivatives include the acid chloride. Activated ester derivatives include activated esters commonly used by those skilled in the art for activating carboxylic acid groups for coupling with an amine to form an amide bond or for coupling with an alcohol to form an ester bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy- 5-norbornene-2,3-dicarboxamide derived esters, 2,4,5-trichlorophenol derived esters and the like.

Compounds of formula (I) in which $R^5$ does not equal $R^6$ may be prepared by reacting one equivalent of a derivatizing reagent, e.g. $R^5$, with a compound of formula (VI) followed by purification of the resultant mono-derivatized intermediate. Reaction of this intermediate with one equivalent of a different derivatizing reagent, e.g. $R^6$, would yield a compound of formula (I) in which $R^5$ does not equal $R^6$.

Compounds of formula (VI) can be prepared by reaction of an epoxide of formula (VII) with an amine of formula (VIII). Any of the numerous reaction conditions employed by those skilled in the art of organic synthesis to react amines with epoxides may be employed to effect the reaction

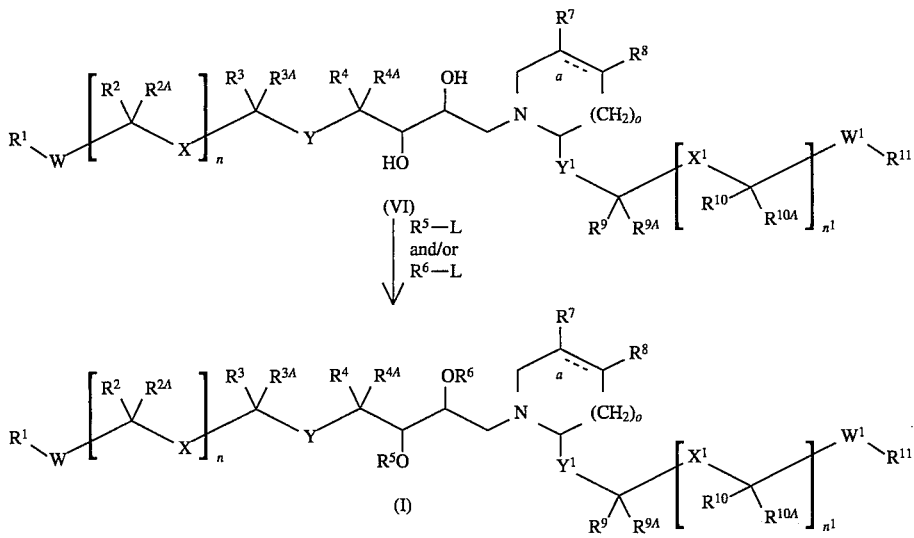

In this reaction, a derivatizing agent, $R^5$-L or $R^6$-L, is reacted with a compound of formula (VI) to give a compound of formula (I). $R^5$ and $R^6$ are as described above. L can be a leaving group, such as a halide or tosylate or any other group capable of displacement in a substitution reaction. L can also be a group capable of undergoing a coupling reaction either in the absence or presence of a coupling reagent. Where L is hydroxyl, the derivatizing agent can participate in a of epoxide (VII) with amine (VIII). The reaction may be carried out in a wide variety of solvents. Preferred solvents are methanol, ethanol and dimethylformamide. The reaction may be performed within the temperature range of room temperature to 150° C. In most cases, the use of a base is not required; however, in some cases, it may be advantageous to use a mild base, such as sodium or potassium carbonate.

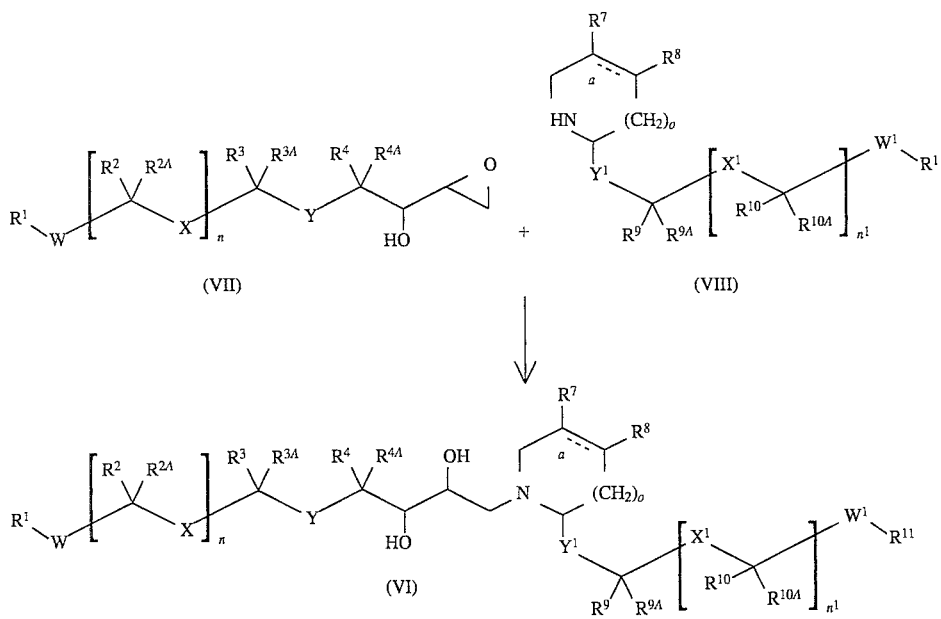

Epoxides of formula (VII) can be prepared via oxidation of an olefin of formula (IX). The oxidation is preferably carried out using an organic peracid such as peracetic acid, perbenzoic acid, a haloperbenzoic acid such as m-chloroperbenzoic acid, perphthalic acid or the like, although it can also be carried out using hydrogen peroxide. The oxidation is more preferably carried out using tert-butyl hydroperoxide in the presence of diisopropyl tartarate-titanium tetraisopropoxide. See M. G. Finn and K. B. Sharpless, in "Asymmetric Synthesis" Vol 5, pp 247–308, J. D. Morrison, ed. Academic Press, Inc. 1985. The oxidation is conveniently carried out in the presence of an organic solvent which is inert to the reaction conditions, for example, an alcohol such as methanol, ethanol etc., a halogenated hydrocarbon such as methylene chloride etc., and the like. The oxidation can be carried out within a wide temperature range, for example, a range between about −70° C. and about room temperature.

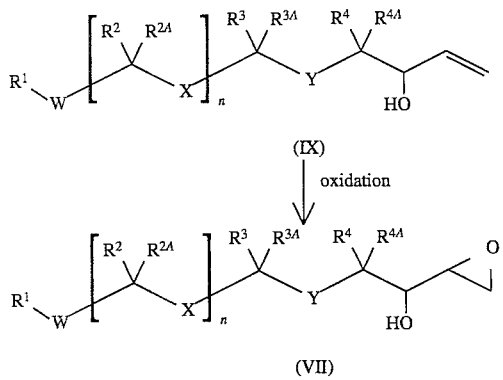

Compounds of formula (IX) can be prepared in a number of ways well known to those skilled in the art. Some preferred ways are shown below.

Compounds of formula (IX) wherein n=zero and Y is —C(=Q)NR$^{14}$ can be prepared by reaction of a carboxylic acid or carboxylic ester of formula (X) with an amine of formula (XI), as shown below. R$^{25}$ of formula (X) is hydrogen or an activating group capable of activating carboxylic acids to nucleophilic substitution. For a review discussing this reaction and activating groups, see Bodanszky and Bodanszky, *The Practice of Peptide Synthesis*, Springer-Verlag, Berlin, 1984, Chapter II pp. 89–150.

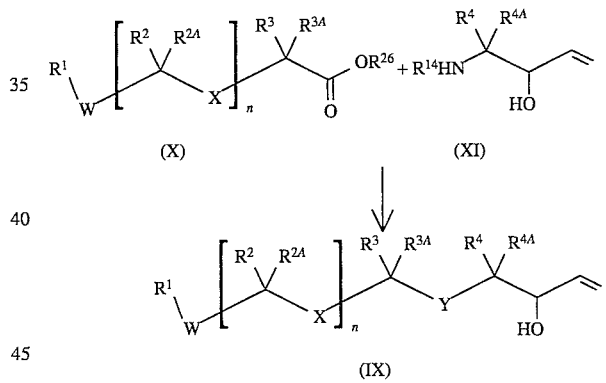

Compounds of formula (X) can be either obtained commercially or synthesized. Hodge, U.S. patent application Ser. No. 659,442, filed Feb. 21, 1991, which is hereby incorporated by reference, discloses a number of methods for the synthesis of compounds of formula (X).

Compounds of formula (IX) wherein Y is SO$_2$NHR$^{14}$ can be prepared by the reaction of (XI) with an activated sulfonate such as (XII):

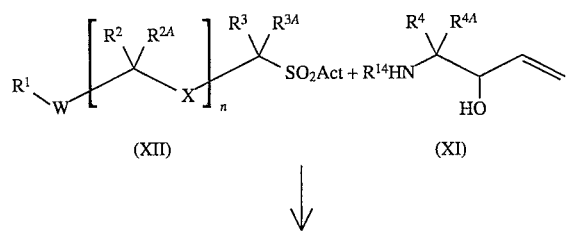

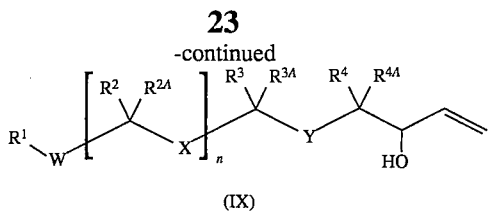

(IX)

For a discussion of activated sulfonates see March, *Advanced Organic Chemistry*, Wiley, New York, 1985, p445. Hodge, U.S. patent application Ser. No. 07/659,442 discloses a number of methods for the synthesis of compounds of formula (XII).

Compounds of formula (VIII) may be either obtained commercially or synthesized. For example, compounds of formula (VIII) wherein Y is —C(=O)NR$^{14}$ can be prepared by reaction of an N-protected carboxylic acid or carboxylic ester of formula (XIII) with an amino moiety of a compound of formula (XIV), followed by removal of the protecting group, as shown below:

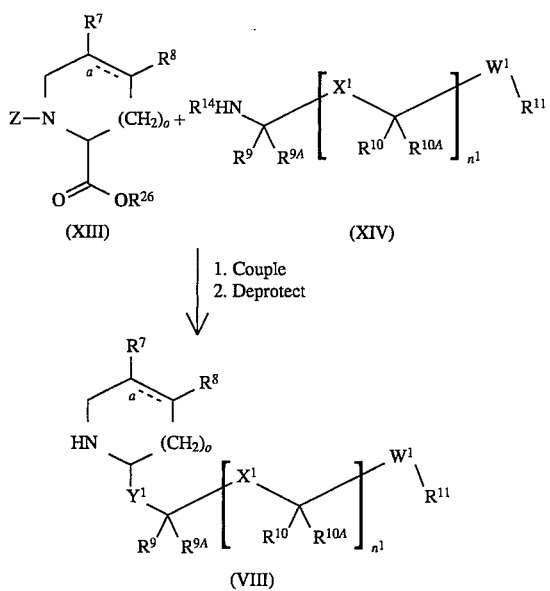

$R^{25}$ of formula (XII) is hydrogen or an activating group capable of activating carboxylic acids to nucleophilic substitution. For a review discussing this reaction and activating groups, see Bodanszky and Bodanszky, *The Practice of Peptide Synthesis*, Springer-Verlag, Berlin, 1984, Chapter II, pp. 89–150. The compounds of formula (XIV) may be peptides which are either commercially obtained or synthesized using techniques well known to those skilled in the art. The compounds of formula (XIII) may be either obtained commercially or may be synthesized using techniques well known to those skilled in the art of organic synthesis.

The synthesis of a compound of formula (XIII) is illustrated by the synthesis of (3S)- decahydroisoquinolinecarboxylic t-butylamide (XV), which is a compound of general formula (XIII), from (3S)-decahydroisoquinolinecarboxylic acid (XVI) and t-butylamide (XVII) as shown below:

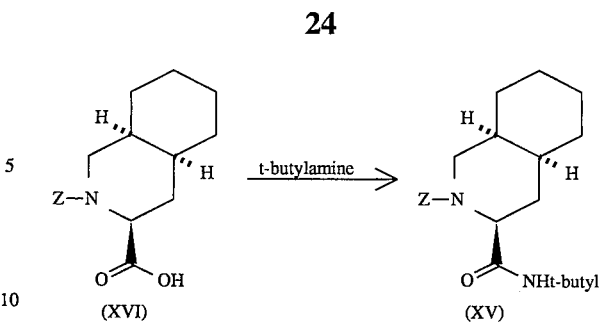

The reaction is carried out according to a procedure disclosed in EP 0 052 870 which is hereby incorporated by reference. In both (XVI) and (XV), Z is an amine protecting group. The acid (XVI) is prepared according to a procedure disclosed in EP 0 052 870 which is hereby incorporated by reference.

The present invention also provides a process for the preparation of compounds of formula (II) or formula (III) which are amine derivitized 1,2-diols. The general reaction scheme is shown below.

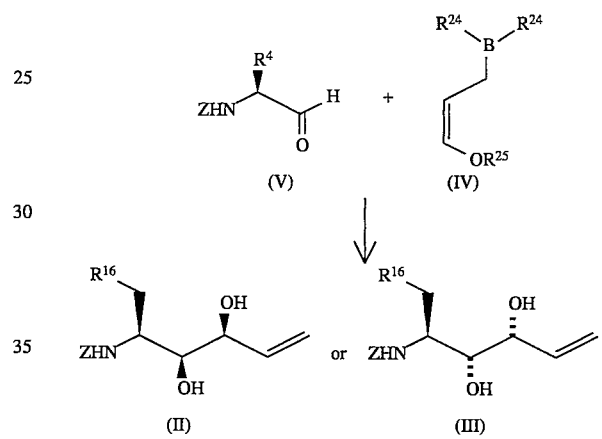

Brown et al. disclose a method for the preparation of 1,2-diols wherein simple, aliphatic aldehydes are reacted with compounds of formula (IV). H. C. Brown et al., J. Am. Chem. Soc., 1988, 1535–1538. The process of the present invention is distinguished from the disclosure of Brown et al. by the complexity of the compound of formula (V) which is the reagent reacted with the compound of formula (IV). The compounds of formula (V) utilized in the process of the present invention may be a-amino aldehydes, a-azido aldehydes or a-protected aminoaldehydes. These compounds are more complex than the simple aldehydes of Brown et al. It was not clear at the outset that such complex molecules would be capable of reaction in the process of the present invention. Furthermore, the compounds of formula (V) react with compounds of formula (IV) in the process of the present invention to give either a compound of formula (II) or a compound of formula (III) in high stereochemical purity. That molecules of such complexity would be capable of reacting to give products of such high stereochemical purity was a surprising result.

The process of the present invention makes possible the stereocontrolled formation of two asymmetric centers at one time. Furthermore, where the compound of formula (V) utilized possesses a chiral carbon atom adjacent to the aldehyde group, the chirality of that carbon atom is maintained in the product of the process. Thus, the process of the present invention can afford stereochemically pure products containing three contiguous chiral carbon atoms.

Reaction of a compound of formula (V) with a compound of formula (IV) in the process of the present invention can lead to either pure compound of formula (II) or a mixture of both (II) and a (III). The outcome is determined by the choice of compound of formula (IV) used in the process. For example, when the compound of formula (IV) that has $R^{24}$=3-pinanyl (derived from (−)-a-pinene) and $R^{25}$=OCH2OCH3 is reacted with a compound of formula (V) that has $R^4$=benzyl, only the corresponding compound of formula (II) is detected. However, when the compound of formula (IV) that has $R^{24}$=3-pinanyl (derived from (+)-a-pinene) and $R^{25}$=OCH2OCH3 is reacted with a compound of formula (V) that has $R^4$=benzyl, both the corresponding compound of formula (II) and the corresponding compound of formula (III) are detected; the ratio of (II) to (III) being 4:1.

In practicing this process, the compound of formula (IV) must be prepared. Compounds of formula (IV) are most easily prepared according to a known procedure. H. C. Brown et al., J. Am. Chem. Soc., 1988, 1535–1538. In general, an allyl ether, such as allyl methoxymethyl ether or allyl methyl ether, is dissolved in a dry, aprotic solvent and cooled in a bath maintained at −78° C. This is then treated with a solution containing an equimolar amount of an alkyl lithium reagent, such as sec-butyllithium. After stirring, the resultant mixture is then treated with either (+)-B-methoxydiisopinocampheylborane or (−)-B-methoxydiisopinocampheylborane. Finally, treatment of this mixture with a 1.3 molar excess of boron trifluoride etherate gives a compound of formula (IV). In preparing compounds of formula (IV) best results are obtained when the the compound is prepared, in situ, at −78° C. and used immediately.

The stereoselectivity of the reaction of compounds of formula (IV) with compounds of formula (V) is an important aspect of the process of the present invention. The resultant reaction product contains at least three contiguous stereocenters: one of these is from the compound of formula (V) and two are created in the reaction with a compound of formula (IV). The product stereocenter arising from the compound of formula (V) has the same stereochemistry as that of the carbon of the compound of formula (V). In operating the process of the present invention, the stereochemistry of the newly created stereocenters can be controlled.

In practicing the process of this invention, a compound of formula (V) is mixed with a compound of formula (IV) in an aprotic solvent. The reaction mixture is then stirred for a period of time, followed by work-up, isolation and purification.

A wide variety of compounds of formula (V) may be used in the process of the present invention. These include, but are not limited to a-amino aldehydes, a-azido aldehydes, a-amino protected aldehydes and any compound possessing a chiral center next to an aldehyde functionality. Preferred compounds include, but are not limited to, a-amino protected aldehydes.

A number of compounds of formula (IV) may be used in the process of the present invention. These include any terpene derived chiral boranes capable of stereospecific addition to a-amino protected aldehydes. Preferred compounds have $R^{24}$=3-pinanyl and $R^{25}$=methyl or methoxymethyl. Most preferred compounds have $R^{24}$=3-pinanyl and $R^{25}$=methoxymethyl.

A number of solvents can be used in the process of the present invention. These include, but are not limited to tetrahydrofuran, ethyl ether and hydrocarbons. The preferred solvent is tetrahydrofuran. Solvents which are incompatible with the process of the present invention include protic solvents, such as carboxylic acids, alcohols, and water; amines; ketones; and aldehydes.

The process of the present invention may be operated within the temperature range of −100° to 80° C. The preferred temperature range is −100° to −30° C. The most preferred temperature range is −100° to −60° C.

The process operates over a time range of 0.1 hour to 72 hours. The usual reaction time is from 0.1 hour to 18 hours.

In operating the process it is important that the reagents, solvents and glassware utilized be dry and oxygen free. Moisture, air and carbon dioxide should be rigorously excluded. The process should be conducted under an atmosphere of nitrogen, argon or helium. It is preferable to operate the process under an atmosphere of either argon or nitrogen.

The process may be operated at a pressure within the range 1 to 100 atmospheres. It is preferable to operate the process at a pressure within the range 1 to 2 atmospheres.

In operating the process, best results are obtained when the reaction mixture is slowly agitated.

After the process is complete, the crude compound of formula (I) produced by this process can be isolated using an aqueous procedure. For example, when it has been determined that the reaction is complete, the reaction mixture may be cooled and treated with 3N sodium acetate solution, followed by addition of 30% hydrogen peroxide. The crude product can then be isolated from the resultant mixture by extraction with an organic solvent, such as ethyl ether.

The crude compound of formula (I) obtained from the isolation step can be further purified by any of a variety of methods employed by those skilled in the art. Compounds of formula (I) which are liquids may be purified by distillation and/or chromatography. Compounds of formula (I) which are solids may be purified by crystallization and/or chromatography.

The compounds of formula (I) prepared were then tested in assays to determine their ability to inhibit HIV protease activity. The assay procedures are described in the example section. It was discovered that all of the compounds of formula (I) tested were active in the test assays.

It is believed the antiviral compounds of this invention can be administered as treatment for viral infections by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams per kilogram of body weight.

Dosage forms (compositions suitable for administration contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil was prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

EXAMPLES

General Details:

All solvents were purified according to procedures described in Perrin, D. D., Armarego, W. L. F. and Perrin, D. R. *Purification of Laboratory Chemicals*, 2nd Edition, Pergamon Press, New York, 1980. Reagents were purchased from Aldrich Chemical Co. Thin layer chromatography was performed on precoated plates of Silica Gel 60 $F_{254}$ (EM Science). Column chromatography was performed on Silica Gel 60 (230–400 mesh, EM Science). $^1$H NMR spectra were recorded at 500 MHz (GE Omega-500) and the chemical shifts in $CDCl_3$ are expressed relative to tetramethylsilane. Optical rotations were measured on a Perkin-Elmer model 241 (Perkin-Elmer, Analytical Instruments Division, Norwalk, Conn. 06856). FAB Mass Spectra were obtained with a VG ZAB-E double focusing mass spectrometer, ion source by VG Analytical Ltd. (Floats Road, Wythenshawe, Manchester, M23 9LE, UK).

EXAMPLE 1

This example details the synthesis of a compound of formula (I) having the structure:

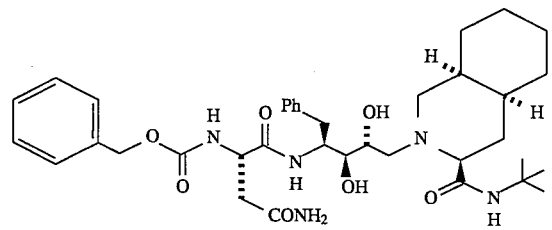

The synthetic pathway for the preparation of this compound is shown in Scheme I.

Intermediate 2:

(See H. C. Brown, P. K. Jadhav, and K. S. Bhat, J. Amer. Chem. Soc. 110, 1535, 1988) In a 1-L round bottom flask was placed 11.4 ml (98 mmol) of allyl methoxymethyl ether dissolved in 50 ml of tetrahydrofuran and cooled in a −78° C. dry ice-acetone bath. The mixture was then treated with 53.7 ml (79 mmol) of 1.47M sec-butyllithium in cyclohexane which was added slowly via syringe and stirred for 15 minutes in the −78° C. bath. 25 g (79 mmol) of (−)-B-methoxydiisopinocampheylborane in 50 ml tetrahydrofuran was then added via double-ended needle and the mixture stirred for 30 minutes at −78° C. bath. The mixture was then treated with 12.9 ml (105 mmol) of boron trifluoride etherate via syringe and stirred for 30 minutes in the −78° C. bath. 11.4 mL (98 mmol) of phenyacetaldehyde, 1, was then added via double-ended needle and the mixture allowed to warm to room temperature in the same bath and stirred for 18 hours. The mixture was then cooled in an ice bath and 30 ml of 3N sodium acetate solution was added slowly followed by 30 ml of 30% hydrogen peroxide solution dropwise. After stirring at room temperature for 2 hours the mixture was diluted with 500 ml water and extracted with 3×100 ml ether. The organic extracts were combined, dried over magnesium sulfate, filtered and concentrated. 100 mL of dodecane was added and the mixture distilled under vaccum to remove isopinocampheol which codistills away with dodecane. The residue purified (325 g silica gel column using 1:4 ethyl acetate/hexane to elute) to provide intermediate 2 (10.321 g; 58.7%).

$^1$H NMR ($CDCl_3$): 2.7(dd, 1H, $J_{AB}$=14 Hz, $J_{AX}$= 9 Hz), 2.9 (dd, 1H, $J_{AB}$=13.6 Hz, $J_{BX}$=3.6 Hz), 3.41(s, 3H) 3.82(m, 1H), 3.94(dd, $J_1$=$J_2$=6.3 Hz), 4.67(q, 2H, J=6.7 Hz), 5.35(m, 2H), 5.8(ddd, 1H), 7.3(m, 5H).

Intermediate 3:

A solution of 10.321 g of intermediate 2 (46.4 mmol) and 18.255 g (69.6 mmol) of triphenylphosphine in 150 ml dry tetrahydrofuran was stirred in a 0° C. ice bath. 11.0 ml (69.6 mmol) of diethylazodicarboxylate was added via syringe to the above mixture and stirred for 5 minutes at 0° C. This was followed by the addition of 15.0 ml (69.6 mmol) of diphenylphosphorylazide via syringe. The ice bath was removed and the mixture stirred for one hour at room temperature. The excess reagents were quenched by the addition of 2.84 ml (70 mmol) of methanol at 0° C. After stirring the mixture for 15 minutes at room temperature, it was concentrated to a small volume and purified (325 g silica gel column using hexane followed 1:40, 1:30, and finally 1:20 EtOAc:Hexane as the eluting solvent) to provide 9.178 g (80.0%) of intermediate 3 as an oil.

$^1$H NMR (CDCl3): 2.72(dd, 1H, $J_{AB}$=14.2 Hz, $J_{AX}$=10 Hz), 2.88(dd, 1H, $J_{AB}$= 14.2 Hz, $J_{BX}$4.6 Hz), 3.4(s, 3H), 3.70(ddd, 1H, $J_1$=4.6 Hz, $J_2$= 9.7 Hz, $J_3$=4.4 Hz), 4.14(dd, $J_1$=7.8 Hz, $J_2$=4.0 Hz), 4.67(q, 2H,J=6.8 Hz), 5.40(m, 2H), 5.84(ddd, 1H), 7.3(m, 5H).

Intermediate 4:

A solution of 9.178 g (37.1 mmol) of intermediate 3 in 100 ml methanol was cooled in a 0° C. ice bath. 5 ml of concentrated sulfuric acid was added slowly via syringe and the mixture allowed to warm to room temperature and stirred for 18 hours. The mixture was poured slowly with stirring into an ice-cold stirred solution of 200 ml 1N solution of Sodium Hydroxide. The mixture was transferred to a 500 ml separatory funnel and the aqueous layer extracted 3×100 ml with chloroform. The chloroform extracts were combined, dried over anhydrous magnesium sulfate, filtered, and concentrated. The residue was purified (325 g silica gel column using 1:20 followed by 1:10 EtOAc:Hexane as the eluting solvent) to provide 5.774 g (76.6%) of intermediate 4.

$^1$H NMR (CDCl3): 2.76(dd, 1H, $J_{AB}$=14.1 Hz, $J_{AX}$=9.2 Hz), 2.88(dd, 1H, $J_{AB}$=14.1 Hz, $J_{BX}$=4.8 Hz), 3.71(ddd, 1H, $J_1$= 4.6 Hz, $J_2$=9.1 Hz, $J_3$=4.4 Hz), 4.22(dd, 1H,$J_1$=9.9 Hz, $J_2$= 4.0 Hz), 5.36(m, 2H), 5.98(ddd, 1H), 7.3(m, 5H).

Intermediate 5:

A solution of 2.032 g (10 mmol) of intermediate 4 and 1.05 ml (5 mmol) diisopropyl-L-tartarate in 90 ml dichloromethane was stirred with 2 g molecular sieves 4A in a −5° C. dry ice-acetone bath. The mixture was then treated with 1.25 ml (4.15 mmol) of titanium(IV) isopropoxide via syringe and the mixture stirred for 5 minutes at −5° C. 6.65 ml (20 mmol) of 3.0M (in 2,2,4-trimethylpentane) t-butylhydroperoxide was added via syringe and the mixture stirred for 10 minutes in the −5° C. bath and then transferred to a −5° C. freezer for 18 hours. The contents were filtered and the filtrate concentrated. The residue was purified (130 g silica gel column using 1:2 EtOAc:Hexane as the eluting solvent) to provide 2.239 g of intermediate 5.

$^1$H NMR (CDCl3): 2.063, (d, 1H, J=3.0 Hz), 2.882(m, 3H), 3.079(dd, 1H, $J_1$= 4.5 Hz, $J_2$=14.1 Hz), 3.44(dd, 1H, $J_1$=6.7 Hz, $J_2$=3.68 Hz ), 3.756(m, 1H), 3.85(m, 1H), 7.3(m, 5H).

Intermediate 6:

A solution 283 mg (1.29 mmol) of intermediate 5, 280 mg (1.17 mmol) of (3S)-decahydroisoquinolinecarboxylic t-butylamide in 5 ml ethanol was heated in an 80° C. oil bath for one hour. The solvent was evaporated off and the residue purified (1:2 to remove excess compound 5 followed by 1:1 EtOAc:Hexane as the eluting solvent) to provide 395 mg (73.8%) of intermediate 6 as a white solid.

$^{13}$C NMR (CDCl3): 20.759, 26.016, 26.644, 28.968, 31.142, 31.263, 33.843, 36.259, 36.346, 51.783, 60.340, 61.777, 66.399, 66.748, 71.837, 127.068, 128.960, 129.862, 138.467, 173.097. The polarity of the mixture was increased to 10% methanol in chloroform to elute 30 mg (10.7%) of unreacted (3S)-decahydroisoquinolinecarboxylic t-butylamide.

Intermediate 7:

A solution of 395 mg (0.86 mmol) of intermediate 6 in 10 ml ethanol was stirred with a suspension of 40 mg of 10% Palladium on carbon as under 1 atmospheric hydrogen pressure for 18 hours at room temperature. The mixture was filtered through a celite pad and the residue washed with ethanol. The filtrate and washings were concentrated to provide 364 mg (98.1%) of intermediate 7 as a white solid which was converted to intermediate 8 without further purification.

Compound 8:

The compound of formula (I) having the above structure was prepared as follows: A solution of 364 mg (0.84 mmol) of intermediate 7 in 2 ml dimethylformamide was stirred with 464 mg (1.2 mmol) Z-L-asparagine nitrophenylester at room temperature for 18 hours. The mixture was made completely free of dimethylformamide and the residue purified [55 g silica gel column using 2% MeOH in CHCl$_3$ and 2.5% to elute p-nitrophenol (a side product) and unreacted Z-asparagine nitrophenyl ester, then increasing the MeOH content to 3% to elute an impurity and finally to 5–7% which began elution of desired compound] to provide 402 mg (70.1%) of compound 8 as a white solid.

$^{13}$C NMR (CDCl3): 17.803, 20.254, 24.784,25.382, 26.071, 28.146, 30.432, 30.526, 33.172, 33.877, 35.646, 36.985, 50.976, 51.093, 51.719, 52.800, 57.645, 59.290, 61.710, 66.219, 66.955, 70.510, 70.533, 126.019, 127.827, 128.054, 128.094, 128.360, 129.190, 135.899, 138.303, 156.114, 170.645, 173.166.

EXAMPLE 2

This example details the synthesis of a compound of formula (I) having the structure:

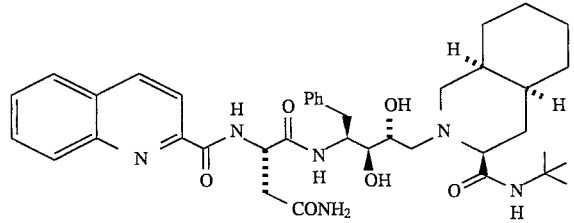

The synthetic pathway for the preparation of this compound is shown in Scheme I.

Intermediate 9:

A solution of 204 mg (0.30 mmol) of compound 8 in 5 ml ethanol was stirred with a suspension of 25 mg of 10% palladium on carbon under 1 atmospheric hydrogen pressure at room temperature for 18 hours. The mixture was filtered through a celite pad and the residue washed with ethanol. The filtrate and the washings were concentrated to provide 125 mg (91.6%) of intermediate 9 as a white solid which was converted to compound of example 2 without further purification.

Compound 10:

The compound of formula (I) having the above structure was prepared as follows: A solution of 120 mg (0.225 mmol) of intermediate 9 in 1 ml dimethylformamide was stirred with 99 mg (0.337 mmol) of quinaldic acid nitrophenylester at room temperature for one hour. The mixture was made completely free of dimethylformamide and the residue purified (33 g silica gel column using 2% followed by 4% MeOH in CHCl$_3$ to remove excess quinaldic acid nitrophenylester and the by-product p-nitrophenol, then increasing the MeOH content to 6% to start the elution and then 7% followed by 8% to to finish the elution) to provide 115 mg (72.9%) of compound 10 as a white solid.

$^{13}$C NMR (CDCl3): 20.453, 25.616, 26.132, 28.562, 30.653, 30.722, 33.354, 34.913, 35.757, 37.092, 50.218, 51.134, 53.766, 59.575, 61.634, 70.884, 118.745, 125.926, 127.561, 128.116, 129.292, 129.381, 130.039, 130.132, 137.332, 138.381, 146.506, 148.879, 164.682, 170.530, 172.950, 173.029.

EXAMPLE 3

This example details the synthesis of a compound of formula (I) having the structure:

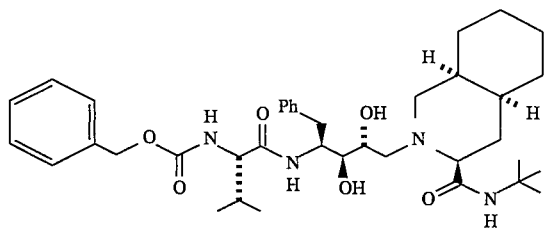

The synthetic pathway for the preparation of this compound is shown in Scheme I except Z-L-aspergine p-nitrophenylester is replaced with Z-L-valine N-hydroxysuccinimide ester as described below.

A solution of 200 mg (0.463 mmol) of intermediate 7 in 1 ml dimethylformamide was stirred with 161 mg (0.463 mmol) Z-L-valine N-hydroxysuccinimide ester at room temperature for 18 hours. The mixture was made completely free of dimethylformamide and the residue purified (33 g silica gel column using 0.5%, followed by 1% MeOH in CHCl$_3$ to elute the excess reagent and 1.5% followed by 2% to elute 221 mg (72%) of compound of example 3.

$^{13}$C NMR (CDCl3): 17.459, 19.303, 20.44, 25.657, 26.315, 28.641, 30.812, 33.479, 36.036, 51.234, 53.367, 59.813, 61.758, 66.392, 67.036, 71.235, 78.267 126.324, 127.991, 128.141, 128.374, 128.514, 129.286, 138.552, 156.55, 171.100, 172.644. [a] D at 25° C.—78.2° (C 1.01 g/ml, DMSO).

EXAMPLE 4

This example details the synthesis of a compound of formula (I) having the structure:

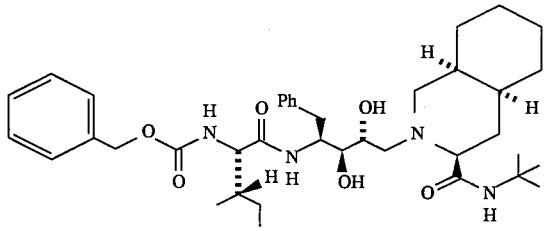

The synthetic pathway for the preparation of this compound is shown in Scheme I except Z-L-aspergine p-nitrophenylester is replaced with Z-L-isoleucine N-hydroxysuccinimide ester as described below.

A solution of 200 mg (0.463 mmol) of intermediate 7 in 1 ml dimethylformamide was stirred with 168 mg (0.463 mmol) Z-L-valine N-hydroxysuccinimide ester at room temperature for 18 hours. The mixture was made completely free of dimethylformamide and the residue purified (33 g silica gel column using 0.5%, followed by 1% MeOH in CHCl$_3$ to elute the excess reagent and 1.5% followed by 2% to elute 198 mg (63%) of compound of example 4.

$^{13}$C NMR (CDCl3): 11.412, 15.538, 20.449, 24.417, 25.661, 26.318, 28.648, 30.826, 33.486, 35.006, 36.044, 37.123, 51.246, 53.524, 59.811, 60.158, 61.700, 66.467, 67.062, 71.202, 77.203, 78.215, 126.340, 128.018, 128.166, 128.388, 128.524, 129.283, 138.564, 156.55, 171.123, 172.632. [a] D at 25° C.–75.9° (C 0.94 g/ml, DMSO).

EXAMPLE 5

This example details the synthesis of a compound of formula (I) having the structure:

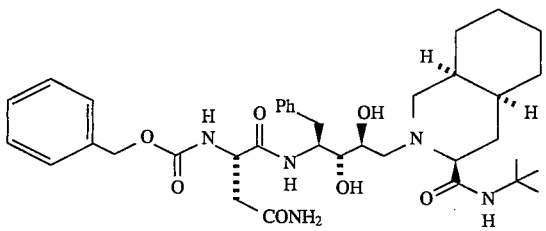

The synthetic pathway for the preparation of this compound is shown in Scheme II.

Intermediate 11:

In a 200 ml R.B. Flask was placed 3.000 g (14.77 mmol) of intermediate 4 from Example 1 and 5.814 g (22.17 mmol) of triphenylphosphine dissolved in 50 ml tetrahydrofuran and cooled in ice bath. The mixture was treated with first 3.49 ml (22.17 mmol) of diethylazodicarboxylate via syringe followed by 2.207 g (22.17 mmol) of benzoic acid. The mixture was stirred at room temperature for one hour and then quenched by adding 20 mmol of methanol and stirring for 15 minutes. The mixture was concentrated and the residue purified (200 g silica gel column using first hexane followed by 1:40 ethyl acetate:hexane as the eluting solvent) to provide 3.319 g (74.1%) of intermediate 11.

$^{13}$C NMR (CDCl3): 36.858, 65.821, 76.576, 119.463, 126.922, 128.451, 128.659, 129.112, 129.785, 132.982, 133.182, 136.963, 165.207.

Intermediate 12:

In a 200 ml R.B. Flask was placed 3.319 g (10.94 mmol) of intermediate 11 dissolved in 50 ml of methanol. The mixture was treated with 1.75 ml of 0.5N sodium methoxide in methanol via syringe and the pH checked to be sure it was at least 10. The mixture was stirred at room temperature for 18 hours and then treated with 2 g of AG50W-X8 for 15 minutes. The pH was checked to be sure it was acidic, and the mixture was filtered and the resin washed with more methanol. The filtrate and the washings were concentrated and the residue purified(130 g silica gel column using 1:20 to 1:10 and finally 1:7 ethyl acetate:hexane as the eluting solvent) to provide 1.762 g (79.3%) of intermediate 12.

$^1$H NMR (CDCl3): 2.841(dd, 1H, J$_{AB}$=13.7 Hz, J$_{AX}$=9.0 Hz), 3.03 (dd, 1H, J$_{AB}$=13.75 Hz, J$_{BX}$=5.43 Hz), 3.55(m, 1H), 4.10 (bs, 1H), 5.349 (m, 2H), 5.95(ddd, 1H), 7.3(m, 5H).

Intermediate 13:

A solution of 1.664 g (8.19 mmol) of intermediate 12 and 958 mg (3.40 mmol) diisopropyl-D-tartarate in 75 ml dichloromethane was stirred with 1.5 g molecular sieves 4A in a −5° C. dry ice-acetone bath. The mixture was then treated with 1.01 ml (3.40 mmol) of titanium(IV) isopropoxide via syringe and the mixture stirred for 5 minutes at −5° C. 5.46 ml (16.38 mmol) of 3.0M (in 2,2,4-trimethylpentane) t-butylhydroperoxide was added via syringe and the mixture stirred for 10 minutes in the −5° C. bath and then transferred to a −5° C. freezer for 18 hours. The contents were filtered and the filtrate concentrated. The residue was purified (130 g silica gel column using 1:5 followed by 1:3 EtOAc:Hexane as the eluting solvent) to provide 1.614 g of intermediate 13.

$^1$H NMR (CDCl3): 2.011 (d, 1H, J=4.35 Hz), 2.865 (m, 2H), 3.065 (m, 3H), 3.672 (m, 2H), 7.247–7.365 (m, 5H).

Intermediate 14:

A solution of 1.615 g (7.38 mmol) of intermediate 13, 1.602 g (6.70 mmol) of (3R,3S)-decahydroisoquinolinecarboxylic t-butylamide in 20 ml ethanol was heated in an 80° C. oil bath for one hour. The solvent was evaporated off and the residue purified (1:3 EtOAc:Hexane to remove excess compound 13 followed by 1:2 EtOAc:Hexane) to provide 797 mg (23.5% yield) of intermediate 15 (a diastereoisomer of intermediate 14) as a white solid. The polarity of the mixture was increased to 1:2 EtOAc:Hexane to elute 1.912 g (35% yield) of the desired intermediate 14.

$^{13}$C NMR (CDCL3): 20.311, 25.449, 26.284, 28.606, 30.731, 30.815, 33.435, 35.883, 36.057, 51.244, 59.807, 61.608, 62.400, 65.143, 71.605, 126.622, 128.581, 129.162, 137.800, 172.481.

Intermediate 16:

A solution of 462 mg (1.01 mmol) of intermediate 14 in 7.5 ml ethanol was stirred with a suspension of 50 mg of 10% palladium on carbon under 1 atmosphere hydrogen pressure at room temperature for 18 hours. The mixture was filtered through a celite pad and the residue washed with ethanol. The filtrate and the washings were concentrated to provide 438 mg (91.6%) of intermediate 16 as a white solid which was converted to intermediate 17 without further purification.

Compound 17:

The compound of formula (I) having the above structure was prepared as follows: A solution of 315 mg (1.01 mmol) of intermediate 16 in 3 ml dimethylformamide was stirred with 542 mg (1.4 mmol) Z-L-asparagine nitrophenylester at room temperature for 18 hours. The mixture was made completely free of dimethylformamide and the residue purified (55 g silica gel column using 1%, 1.5%, 2%, 2.5%, followed by 3% MeOH in CHCl₃ to elute p-nitrophenol (a side product) and unreacted Z-asparagine nitrophenyl ester, then increasing the MeOH to 5–7% which began elution of desired compound to provide 395 mg (57% yield) of compound 17 as a white solid.

$^{13}$C NMR (CDCl3): 20.225, 25.341, 26.222, 28.481, 30.552, 30.622, 33.233, 35.821, 36.290, 37.893, 51.037, 51.401, 52.109, 59.367, 61.261, 64.009, 67.211, 71.306, 78.329, 126.212, 128.001, 128.275, 128.400, 128.509, 129.097, 135.638, 138.034, 156.033, 172.020, 172.188, 172.313.

EXAMPLE 6

This example details the synthesis of a compound of formula (I) having the structure:

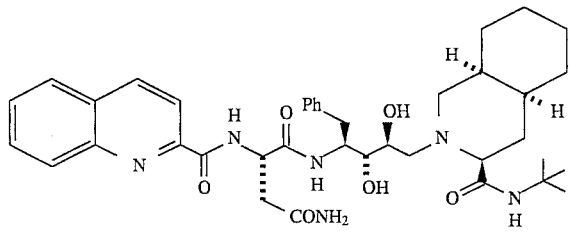

The synthetic pathway for the preparation of this compound is shown in Scheme I.

Intermediate 18:

A solution of 202 mg (0.30 mmol) of intermediate 17 in 7.5 ml ethanol was stirred with a suspension of 50 mg of 10% palladium on carbon under 1 atmosphere hydrogen pressure at room temperature for 18 hours. The mixture was filtered through a celite pad and the residue washed with ethanol. The filtrate and the washings were concentrated to provide 169 mg of compound 18 as a white solid (TLC in 1:8 CH₃OH:CHCl₃; Rf=0.1) which was converted to compound 19 without further purification.

Compound 19:

The compound of formula (I) having the above structure was prepared as follows: A solution of 159 mg (0.3 mmol) of intermediate 18 in 1 ml dimethylformamide was stirred with 110 mg (0.375 mmol) of quinaldic acid nitrophenylester at room temperature for 18 hours. The mixture was made completely free of dimethylformamide and the residue purified (33 g silica gel column) using 1%, 2%, 3%, 4%, followed by 5% MeOH in CHCl₃ to provide 62.5 mg (29.7%) of compound 19 as a white solid.

$^{13}$C NMR (CDCl3): 20.309, 25.202, 26.212, 28.576, 30.698, 30.749, 33.352, 35.947, 36.562, 37.032, 50.874, 51.108, 51.367, 59.435, 61.384, 64.023, 71.511, 76.784, 78.538, 118.674, 126.186, 127.611, 128.350, 128.390, 129.137, 129.415, 130.155, 130.327, 137.334, 138.113, 146.588, 148.604, 165.069, 172.186, 172.346, 172.362.

EXAMPLE 7

This example details the synthesis of a compound of formula (I) having the structure:

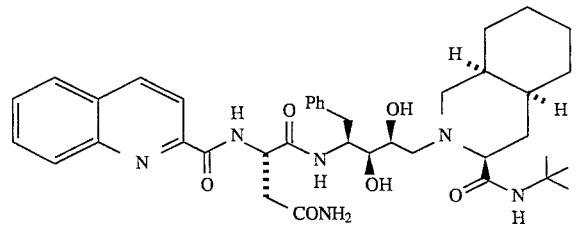

The synthetic pathway for the preparation of this compound is shown in Scheme III. This example also exemplifies the process provide by the invention: the preparation of compounds of formulae (II) or (III) comprising reacting an a-pinene derived borane reagent of formula (IV) with an aldehyde of formula (V). This process is exemplified in the preparation of Intermediate 20.

Intermediate 20:

In a 1-L round bottom flask was placed 6.5 ml (49.5 mmol) of allyl methoxymethyl ether dissolved in 50 ml of tetrahydrofuran and cooled in a −78° C. dry ice-acetone bath. The mixture was then treated with 33.6 ml (49.5 mmol) of 1.47M sec-butyllithium in cyclohexane which was added slowly via syringe and stirred for 15 minutes in the −78° C. bath. 15.66 g (49.5 mmol) of (+)-B-methoxydiisopinocampheylborane in 50 ml tetrahydrofuran was then added via double-ended needle and the mixture stirred for 30 minutes at −78° C. bath. The mixture was then treated with 8.12 ml (66.0 mmol) of boron trifluoride etherate via syringe and stirred for 30 minutes in the −78° C. bath. 12.26 g (43.3 mmol) of Z-L-phenylalaninal in 50 ml tetrahydrofuran was then added via double-ended needle and the mixture allowed to warm to room temperature in the same bath and stirred for 18 hours. The mixture was then cooled in an ice bath and 25 ml of 3N sodium acetate solution was added slowly followed by 40 ml of 30% hydrogen peroxide solution dropwise. After stirring at room temperature for 2 hours the mixture was diluted with 500 ml water and extracted with 3×100 ml ether. The organic extracts were combined, dried over magnesium sulfate, filtered, concentrated, and the residue purified (500 g silica gel column using 1:5 followed by 1:4 to elute the by-product isopinocampheol, followed by 1:3 ethyl acetate:hexane to elute 13.024 g (78% yield) of intermediate 20.

$^{13}$C NMR (CDCl3): 35.693, 35.724, 53.847, 55.966, 66.595, 75.183, 78.792, 94.497, 120.042, 126.397, 127.862, 127.914, 128.370, 128.395, 129.500, 134.408, 137.972, 155.827.

Intermediate 21:

A solution of 2.5 g (6.49 mmol) of intermediate 20 in 25 ml methanol was cooled in a 0° C. ice bath. 1.25 ml of concentrated sulfuric acid was added slowly via syringe and the mixture allowed to warm to room temperature and stirred for 18 hours. A white precipitate appeared after 30 minutes and increased to appreciable amount after 18 hours. The mixture was poured slowly with stirring into an ice-cold stirred solution of 45 ml 1N solution of sodium hydroxide. The mixture was transferred to a separatory funnel and extracted 3×50 ml with chloroform. The chloroform extracts were combined, dried over anhydrous magnesium sulfate, filtered, and concentrated. The residue was crystallized from ethyl acetate to provide 1.01 g of pure intermediate 21 and 878 mg of slightly impure 21 (overall yield 85%).

$^1$H NMR (CDCl3): 2.47(d, 1H, J=7.5 Hz), 2.92 (dd, 1H, $J_{AB}$=14.2 Hz, $J_{AX}$=7.9 Hz), 3.12 (dd, 1H, $J_{AB}$= 14.3 Hz, $J_{BX}$=4.2 Hz), 3.40(ddd, 1H, $J_1$=2 Hz, $J_2$=9.3 Hz, $J_3$ =6.4 Hz ), 3.51(d, 1H, J=4.2), 3.94(m, 1H) 4.21 (bm, 1H), 4.85 (d, 1H, J=8.7 Hz), 5.05 (q, 2H, $J_{AB}$=12 Hz, $J_{BA}$= 3.6 Hz), 5.33 (m, 2H), 5.88 (ddd, 1H, $J_1$=5 Hz, $J_2$=10.6 Hz, $J_3$=10.4 Hz, 7.28(m, 10H).

Intermediate 22:

To a stirred solution of 950 mg (2.78 mmol) of intermediate 21 in 10 ml of anhydrous pyridine was at 0° C. was added 50 mg of dimethylaminopyridine and 2.62 mL (27.8 mmol) of acetic anhydride and then allowed to stir at room temperature for 4 hours. The mixture was then treated with 5 ml of ice-cold water at 0° C. stirred for 15 minutes, further diluted with water, extracted with 3×50 mL dichloromethane. The organic extract was washed with 1N HCl, followed by saturated sodium bicarbonate and brine. The residue after removal of solvent was purified (25 g silica gel column using 1:3 ethyl acetate:hexane as the eluting solvent) to provide 1.17 g (98.8% yield) of intermediate 22.

Intermediate 23:

To a solution of 1.14 g (2.68 mmol) of intermediate 22 in 60 mL dry methanol at −78° C. was passed dry ozone until the blue color persisted. The ozonide was treated with 378 mg (10 mmol) of sodium borohydride at −78° C. and the contents were warmed up to room temperature. The residue was chromatographed to provide diacetate and possibly monoacetate which were separately treated with 0.5N sodium methoxide in methanol to provide 510 mg (55% combined yield) of intermediate 23.

Intermediate 24:

To a stirred solution of 537 mg (1.55 mmol) of intermediate 23 in 5 mL of pyridine at −20° C. was added 326 mg (1.71 mmol) p-tolune sulfonyl chloride. The contents were stirred for 20 minutes each at −20° C., 0° C., and 25° C. The mixture was diluted with water and extracted with 3×30 mL dichloromethane. The organic extract was washed with ice-cold 1N HCl, followed by saturated sodium bicarbonate and brine. The residue was purified (55 g silica gel column using 2:3 ethyl acetate:hexane as the eluting solvent) to provide 448 mg (57.7% yield) of intermediate 24.

Intermediate 25:

A solution 448 mg (0.896 mmol) of intermediate 24 in 5 mL methanol was treated at 0° C. with 248 mg (1.79 mmol) of potassium carbonate. After stirring the contents at room temperature for 15 minutes TLC (2:3 ethyl acetate:Hexane, Rf=0.21) indicated a complete reaction. The mixture was diluted with water and extracted with 3×30 mL dichloromethane. The organic extract was washed with water and brine. The residue was purified (55 g silica gel column using 2:3 acetate:hexane as the eluting solvent) to provide 151 mg (51.5% yield) of intermediate 25.

Intermediate 26:

A solution 175 mg (0.53 mmol) of 25 in 5 mL ethanol was heated at 80° C. with 209 mg (0.878 mmol) of (3S)-decahydroisoquinolinecarboxylic t-butylamide. After heating the contents at 80° C. for 1 hour TLC (1:1 ethyl acetate:Hexane, Rf=0.20) indicated a complete reaction. The residue after removal of solvent was purified (33 g silica gel column using 1:1 acetate:hexane as the eluting solvent) to provide 287 mg (95.7% yield) of intermediate 26.

Intermediate 27:

A solution 282 mg (0.5 mmol) of intermediate 26 in 7.5 mL ethanol was stirred at 23° C. with 30 mg of 10% palladium on carbon under 1 atmosphere pressure of hydrogen for 18 hours. TLC (1:8 methanol:chloroform, Rf= 0.09) indicated complete reaction. The mixture was filtered through celite pad and the filtrate was concentrated to provide 196 mg (91% yield) of intermediate 27.

Intermediate 28:

A solution of 195 mg (0.45 mmol) of intermediate 27 in 1 ml dimethylformamide was stirred with 193 mg (0.5 mmol) L-Z-asparagine nitrophenylester at room temperature for 2 hours. TLC (1:8 methanol:chloroform, Rf= 0.30) indicated incomplete reaction. 96 mg of Z-L-asparagine nitrophenylester and the contents stirred for additional 1 hour. TLC indicated a complete reaction. The mixture was made completely free of dimethylformamide and the residue purified (55 g silica gel column using 2% MeOH in CHCl$_3$ and 2.5% to elute p-nitrophenol(a side product) and unreacted Z-asparagine nitrophenyl ester, then increasing the MeOH content to 3% to elute an impurity and finally to 5–7% to elute the desired compound) to provide 191 mg (62% yield) of intermediate 28 as a white solid.

Intermediate 29:

A solution of 170 mg (0.25 mmol) of intermediate 28 in 5 ml ethanol was stirred with a suspension of 30 mg of 10% palladium on carbon under 1 atmospheric hydrogen pressure at room temperature for 18 hours. TLC (1:8 methanol:chloroform) indicated a complete reaction. The mixture was filtered through a celite pad and the residue washed with ethanol. The filtrate and the washings were concentrated to provide 149 mg of 29 as a white solid which was converted to compound 30 without further purification.

Compound 30:

The compound of formula (I) having the above structure was prepared as follows: A solution of 147 mg (0.27 mmol) of compound 29 in 1 ml dimethylformamide was stirred with 87 mg (0.296 mmol) of quinaldic acid nitrophenylester at room temperature for 18 hours. TLC (1:8 methanol:chloroform, Rf=0.29) indicated a complete reaction. The mixture was made completely free of dimethylformamide and the residue purified (33 g silica gel column using 2% followed by 4% MeOH in CHCl$_3$ to remove excess quinaldic acid nitrophenylester and the by-product p-nitrophenol, then increasing the methanol content to 6% to start the elution and then 7% followed by 8% to to finish the elution) to provide 111 mg (59% yield) of compound 30 as a white solid.

EXAMPLE 8

This example details the synthesis of a compound of formula (I) having the structure:

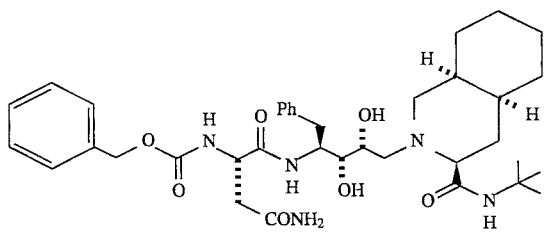

The synthetic pathway for the preparation of this compound is shown in Scheme IV. This example also exemplifies the process provide by the invention: the preparation of compounds of formulae (II) or (III) comprising reacting an a-pinene derived borane reagent of formula (IV) with an aldehyde of formula (V). This process is exemplified in the preparation of Intermediate 31.

Intermediate 31:

In a 1-L round bottom flask was placed 13.0 ml (108.8 mmol) of allyl methoxymethyl ether dissolved in 100 ml of tetrahydrofuran and cooled in a −78° C. dry ice-acetone bath. The mixture was then treated with 67 ml (99 mmol) of 1.47M sec-butyllithium in cyclohexane which was added slowly via syringe and stirred for 15 minutes in the −78° C. bath. 31.5 g (99.6 mmol) of (–)-B-methoxydiisopinocampheylborane in 100 ml tetrahydrofuran was then added via double-ended needle and the mixture stirred for 30 minutes in the −78° C. bath. The mixture was then treated with 16.3 ml (132.5 mmol) of boron trifluoride etherate via syringe and stirred for 30 minutes in the −78° C. bath. 23.6 g (83.3 mmol) of Z-L-phenylalaninal in 100 ml tetrahydrofuran was then added via double-ended needle and the mixture allowed to warm to room temperature in the same bath and stirred for 18 hours. The mixture was then cooled in an ice bath and 80 ml of 3N sodium acetate solution was added slowly followed by 80 ml of 30% hydrogen peroxide solution dropwise. After stirring at room temperature for 18 hours the mixture was diluted with 500 ml water and extracted with 3×100 ml ether. The organic extracts were combined, dried over magnesium sulfate, filtered, concentrated, and the residue purified (500 g silica gel column using 1:5 followed by 1:4 to elute the by-product isopinocampheol, followed by 1:4 ethyl acetate:hexane to elute 3.95 g (12% yield) of intermediate 31.

$^{13}$C NMR (CDCl3): 39.344, 55.825, 66.686, 80.269, 94.844, 120.845, 126.353, 127.939, 127.971, 128.064, 128.378, 128.441,129.411, 133.670, 138.018, 155.896. 1:3 Ethyl acetate:hexane to eluted intermediate 20 (16.6 g, 50%, yield).

Intermediate 32:

To a solution of 4.46 g (11.6 mmol) of intermediate 31 in 275 mL dry methanol at −78° C. was passed dry ozone until the blue color persisted. The ozonide was treated with 1.755 mg (46.37 mmol) of sodium borohydride at −78° C. and the contents were warmed up to room temperature and stirred until the solution showed any detectable level of peroxide. The reaction mixture was concentrated to a small volume, diluted with 200 mL dichloromethane which was washed with water and brine. The residue was purified (200 g silica gel column using 1:1 ethyl acetate:hexane followed by 20:1:20 of ethyl acetate:ethyl alcohol:hexane to elute 2.478 g (54.9% yield) of intermediate 32.

Intermediate 33:

To a stirred solution of 2.37 g (6.09 mmol) of intermediate 32 in 20 mL methanol at 0° C. was added 20 mL of 8% solution of anhydrous hydrogen chloride in methanol. The contents were stirred at room temperature for 30 minutes. The solution was concentrated under vaccum to provide 1.998 g (95% yield) of intermediate 33 as white solid, M. P. 144°– 146° C.

Intermediate 34:

To a stirred solution of 1.998 g (5.78 mmol) of 33 in 20 mL of pyridine at −20° C. was added 1.213 g (6.36 mmol) p-toluene sulfonyl chloride. The contents were stirred for 20 minutes each at −20° C., 0° C., and 25° C. The mixture was diluted with water and extracted with 3×30 mL dichloromethane. The organic extract was washed with ice-cold 1N HCl, followed by saturated sodium bicarbonate and brine. The residue was purified (130 g silica gel column using 2:3 ethyl acetate:hexane, followed by 1:1 EtOAc:Hexane as the eluting solvents) to provide 1.525 g (52.8% yield) of intermediate 34.

Intermediate 35:

A solution 1.492 g (2.98 mmol) of intermediate 34 in 15 mL methanol was treated at 0° C. with 823 mg (5.96 mmol) of potassium carbonate. After stirring the contents at room temperature for 15 minutes TLC (2:3 ethyl acetate:Hexane, Rf=0.21) indicated a complete reaction. The mixture was concentrated, then diluted with water and extracted with 3×30 mL dichloromethane. The organic extract was washed with water and brine. The residue was purified (130 g silica gel column using 2:3 ethyl acetate:hexane as the eluting solvent) to provide intermediate 35 as a white solid, M. P. 81°–82.5° C., 529 mg (54.2% yield).

Intermediate 36:

A solution 479 mg (1.46 mmol) of intermediate 37 in 10 mL ethanol was heated at 80° C. with 383 mg (1.61 mmol) of (3S)-decahydroisoquinolinecarboxylic t-butylamide. After heating the contents at 80° C. for 1 hour TLC (1:1 ethyl acetate:Hexane, Rf=0.20) indicated >50% completion of reaction. 191 mg (0.8 mmol) of (3S)-decahydroisoquinolinecarboxylic t-butylamide was added and the contents heated at 80° C. for 2 hours. TLC (1:1 ethyl acetate:Hexane, Rf=0.20) indicated >80% completion of reaction. The reaction was concentrated and the residue purified (130 g silica gel column using first 2:3 to recover 92 mg (19.2%) of unreacted Compound 35 and then 1:1 EtOAc:Hexane) to provide 608 mg (73.6% yield) of Compound 36.

$^{13}$C NMR (CDCl3): 20.54, 25.47, 26.22, 28.78, 30.97, 31.19, 33.65, 36.07, 39.37, 51.38, 55.19, 57.79, 59.62, 67.71, 69.52, 70.23, 70.55, 126.30, 127.86, 127.92, 128.39, 128.42, 129.51, 138.29, 156.55, 174.06.

Intermediate 37:

A solution 558 mg (1.01 mmol) of intermediate 36 in 10 mL ethanol was stirred at 23° C. with 56 mg of 10% palladium on carbon under 1 atmospheric pressure of hydrogen for 18 hours. TLC (1:8 methanol:chloroform, Rf= 0.09) indicated a complete reaction. The mixture was filtered through celite pad and the filtrate was concentrated to provide 416 mg (95.4% yield) of intermediate 37.

Compound 38:

A solution of 386 mg (0.9 mmol) of intermediate 37 in 3 ml dimethylformamide was stirred with 381 mg (0.98 mmol) Z-L-asparagine nitrophenylester at room temperature for 1 hour. TLC (1:8 methanol:chloroform, Rf=0.30) indicated an incomplete reaction. Additional 170 mg of Z-L-asparagine nitrophenylester was added to the mixture and the contents stirred for 1 more hour. TLC indicated a complete reaction. The mixture was made completely free of dimethylformamide and the residue purified [55 g silica gel column using 4% MeOH in $CHCl_3$ to elute p-nitrophenol (a side product) and unreacted Z-asparagine nitrophenyl ester, then increasing the MeOH content initially to 6%, followed by 7% to elute the desired product] to provide 435 mg (71.6% yield) of compound 38 as a white solid.

$^{13}C$ NMR (CDCl3): 20.58, 25.55, 26.19, 28.75, 30.91, 31.07, 33.58, 35.85, 37.60, 38.95, 51.18, 52.26, 54.40, 58.11, 58.96, 67.20, 68.81, 70.05, 70.39, 126.28, 128.07, 128.16, 128.35, 128.45, 128.51, 129.52, 136.31, 138.24, 156.07, 170.45, 173.09, 174.15. [a] D at 25° C.–74.0° (C 1.03 g/ml).

EXAMPLE 9

This example details the synthesis of a compound of formula (I) having the structure:

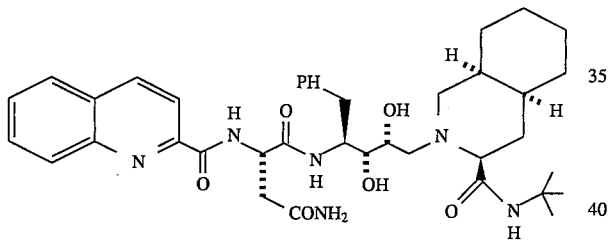

The synthetic pathway for the preparation of this compound is shown in Scheme IV.

Intermediate 39:

A solution of 335 mg (0.49 mmol) of 38 in 5 ml ethanol and 2.5 mL of dioxane was stirred with a suspension of 50 mg of 10% palladium on carbon under 1 atmospheric hydrogen pressure at room temperature for 18 hours. TLC (1:8 methanol:chloroform) indicated a incomplete reaction. 50 mg of 10% palladium on carbon was added and stirred at room temperature for 4 hours by which time the reaction was incomplete. Additional 50 mg of 10% palladium on carbon was added and the mixture stirred for 18 hours. The mixture was filtered through a celite pad and the residue washed with ethanol. The filtrate and the washings were concentrated to provide 276 mg of 39 as a white solid which was converted to compound 40 without further purification.

Compound 40:

The compound of formula (I) having the above structure was prepared as follows: A solution of 200 mg (0.366 mmol) of intermediate 39 in 2 ml dimethylformamide was stirred with 119 mg (0.403 mmol) of quinaldic acid nitrophenylester at room temperature for 1.5 hours. TLC (1:8 methanol:chloroform, Rf= 0.29) indicated a complete reaction. The mixture was made completely free of dimethylformamide and the residue purified (33 g silica gel column using 2% followed by 2.5% MeOH in $CHCl_3$ to remove excess quinaldic acid nitrophenylester and the by-product p-nitrophenol, then increasing the methanol content to 3–6% to finish the elution) to provide 173 mg (67.4% yield) of compound 40 as a white solid.

$^{13}C$ NMR (CDCl3): 20.61, 25.58, 26.17, 28.72, 30.87, 31.00, 33.53, 35.78, 37.67, 38.99, 50.76, 51.08, 54.56, 58.21, 58.83, 68.95, 70.00, 70.22,118.79, 126.14, 127.57, 128.07, 128.27, 129.46, 130.09, 130.15, 137.31, 138.19, 146.70, 149.13, 164.83, 170.29, 173.17, 174.11. [a] D at 25° C.–39° (C 0.98 g/ml).

UTILITY

The compounds of Formula (I) possess retroviral protease inhibitory activity and are therefore useful as antiviral agents for the treatment of viral diseases. More particularly, the compounds of Formula (I) are bioavailable, possess HIV protease inhibitory activity and are effective as inhibitors of HIV growth. The protease inhibitory activity of the compounds of the present invention is demonstrated using standard assays of protease activity, for example, the cell free HIV protease inhibition assay as described below. The ability of compounds of present invention to inhibit viral growth or infectivity is demonstrated in standard assays of viral growth or infectivity, for example using the HIV yield reduction cell assay and HIV low multiplicity assay both described below.

As will be readily apparent to those skilled in the art upon review of the present specification, the compounds of the present invention are also useful for the inhibition of HIV in an ex vivo sample containing, or suspected of containing, HIV. The compounds according to the invention can be used to treat body fluid samples. Thus, the compounds of the present invention can be used to inhibit HIV present in, for example, a serum or semen sample which contains, or is suspected of containing, HIV. The samples can be treated, for example, in a method similar to those described below for the "HIV Yield Reduction Cell Assay" and the "HIV Low Multiplicity Assay".

As will also be readily apparent to those skilled in the art, the compounds according to the invention can also be utilized as standard or reference compounds for use in tests screening for agents which inhibit viral replication and/or HIV protease in vivo or in vitro. Thus, the compounds according to the present invention can be used as positive controls of inhibitory activity in such assays and as a quality control standard. The assays can be performed, for example, as described below in the "Cell Free HIV Protease Inhibition Assay". The compounds of the present invention can be provided in a commercial kit or container for use as such standard or reference compounds.

Since the Compounds of the present invention exhibit specificity for HIV protease, the compounds of the present invention can also be used as diagnostic reagents in diagnostic assays for the detection of HIV protease. Thus, inhibition of the protease activity in an assay (such as the assays described herein) by a compound of the present invention would be indicative of the presence of HIV protease and, consequently, HIV virus.

Standard procedures were used for detecting and comparing the activity of the compounds of this invention. A compound is considered to be active if it has as $IC_{50}$ or Ki value of less than about 1 mM for the inhibition of HIV protease or HIV viral growth or infectivity. The results are summarized in Table I.

Procedure III: Cell Free Protease Inhibition Assay Materials:

HIV gag polyprotein corresponding to all of p17 and 78 amino acids of p24, produced by in vitro translation using rabbit reticulocyte lysate and mRNA prepared in vitro from plasmid encoding full length gag polyprotein linerized with the restriction enzyme Pst 1. (see S. Erickson-Viitanen et al., AIDS Research and Human Retroviruses, 5 (6), 577 (1989) for plasmid construction, and basis for assay).

Source of protease: Either (A) crude *E. coli* lysate of bacteria harboring a plasmid containing HIV protease under the control of the lac promotor, used at a final concentration of 0.5 mg/ml, or (B) inclusion bodies of *E. coli* harboring plasmid containing HIV protease under the control of the T7 promotor (Cheng et al., Gene, in press (1990)). Such inclusion bodies were solubilized in 8M urea, 50 mM Tris pH 8.0. Protease activity was recovered by dilution of the inclusion bodies 20-fold in buffer containing 50 mM Sodium Acetate, pH 5.5, 1 mM EDTA, 10% glycerol and 5% ethylene glycol. This protease source was used at a final concentration of 0.00875 mg/ml.

Inhibitory compounds were dissolved in sufficient DMSO to make a 2.5 mM stock concentration. All further dilutions were done in DMSO.

Set Up

Into sterile test tubes were placed the following:

1 μL inhibitor dilutions 14 ul HIV protease in Phosphate Buffered Saline (20 mM Sodium Phosphate, 0.15M NaCl, pH 6.5).

5 μl of in vitro translation products.

Reactions were incubated at 30° C., then quenched by the addition of Sample buffer. See U. K. Laemmli, Nature, 1970, 227:680–685.

One fourth of each sample was analyzed on an 8–16% gradient denaturing acrylamide gel (Novex, Inc), according to Laemmli. Following electrophoresis, gels were fixed, impregnated with Enhance (Du Pont NEN, Boston, Mass.) and dried according to manufacturers instructions (NEN). Dried fluorographs were exposed to film and/or quantitated using an Ambis radioanalytic scanner.

Each group of test compounds was compared to the values obtained for pepstatin, a well known inhibitor of acid proteases. Inhibitory concentration for 50% inhibition ($IC_{50}$) is determined from plots of log concentration inhibitor versus % inhibition of protease activity.

Biological Activity: $IC_{50}$ is the concentration necessary for reducing the activity of the enzyme by 50%. A compound is considered active if the $IC_{50}$ for that compound is less than about $1 \times 10^{-2}$ grams/ml.

HIV Yield Reduction Cell Assay

Materials:

MT-2, a human T-cell line, was cultured in RPMI medium supplemented with 5% (v/v) heat inactivated fetal calf serum (FCS), L-glutamine and gentamycin. Human immunodeficiency virus strains, HIV(3B) and HIV(Rf) were propagated in H-9 cells in RPMI with 5% FCS. Poly-L-lysine (Sigma) coated cell culture plates were prepared according to the method of Harada et al. (Science 1985 229:563–566). MTT, 3-(4,5-dimethylthiazol- 2yl) -2,5-diphenyltetrazolium bromide, was obtained from Sigma.

Method:

Test compounds were dissolved in dimethylsulfoxide to 5 mg/ml and serially diluted into RPMI medium to ten times the desired final concentration. MT-2 cells ($5 \times 10^5$/ml) in 2.3 ml were mixed with 0.3 ml of the appropriate test compound solution and allowed to sit for 30 minutes at room temperature. HIV(3B) or HIV(RF) (~$5 \times 10^5$ plaque forming units/ml) in 0.375 ml was added to the cell and compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 ml of each dilution was added to 9 ml of MT-2 cells in RPMI. Cells and virus were incubated for 3 hours at 36° C. to allow for efficient attachment of the virus to cells. Each virus and cell mixture was aliquoted equally to two wells of a six well poly-L-lysine coated culture plate and incubated overnight at 36° C., 4% $CO_2$. Liquid and unattached cells were removed prior to the addition of 1.5 ml of RPMI with 0.75% (w/v) Seaplaque agarose (FMC Corp) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/ml was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of any inhibitors.

HIV Low Multiplicity Assby

Materials:

MT-2, a human T-cell line, was cultured in RPMI medium supplemented with 5% (v/v) heat inactivated fetal calf serum (FCS), L-glutamine and gentamycin (GIBCO). Human immunodeficiency virus strains HIV(3B) and HIV(Rf) were propagated in H-9 cells in RPMI with 5% FCS. XTT, benzene-sulfonic acid, 3,3'-[1-[(phenylamino)carbonyl]-3, 4-tetrazolium]bis(4-methoxy-6-nitro)-, sodium salt, was obtained from Starks Associates, Inc.

Method:

Test compounds were dissolved in dimethyl-sulfoxide to 5 mg/ml and serially diluted into RPMI medium to ten times the desired final concentration. MT-2 cells ($5 \times 10^4$/0.1 ml) were added to each well of a 96 well culture plate and 0.02 ml of the appropriate test compound solution was added to the cells such that each compound concentration was present in two wells. The cells and compounds were allowed to sit for 30 minutes at room temperature. HIV(3B) or HIV(RF) (~$5 \times 10^5$ plaque forming units/ml) was diluted in medium and added to the cell and compound mixtures to give a multiplicity of infection of 0.01 plaque forming unit/cell. The mixtures were incubated for 7 days at 36° C., during which time the virus replicated and caused the death of unprotected cells. The percentage of cells protected from virus induced cell death was determined by the degree of metabolism of the tetrazolium dye, XTT. In living cells, XTT was metabolized to a colored formazan product which was quantitated spectrophotometrically at 450 nm. The amount of colored formazan was proportional to the number of cells protected from virus by the test compound. The concentration of compound protecting either 50% ($IC_{50}$) or 90% ($IC_{90}$) with respect to an uninfected cell culture was determined. A compound is considered active if the $IC_{90}$ for that compound is less than about $1 \times 10^{-2}$ grams/ml.

Tables I–VII set forth various dihydroxypropylamine containing retroviral protease inhibitors of the present invention.

TABLE I

| Ex. No. | STRUCTURE | [α]$_D$ at 25° C. (g/100 ml) [M$^+$ + H] | IC$_{50}$ (gag) μg/ml | IC$_{90}$ Cells μg/ml |
|---|---|---|---|---|
| 1 | 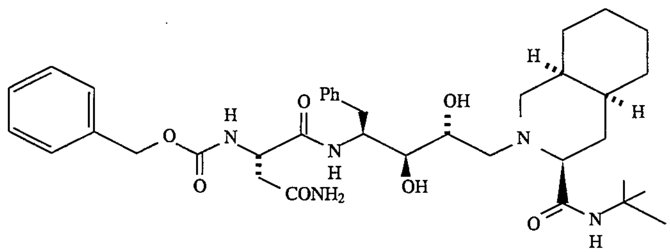 | [680.45] | 2.05 | 2.0 |
| 2 | 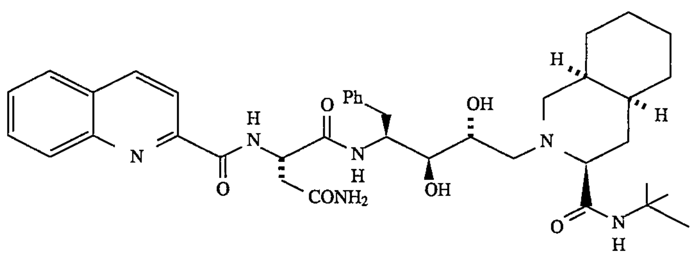 | −56.6 (0.35) [701.47] | 0.38 | 0.3 |
| 3 | 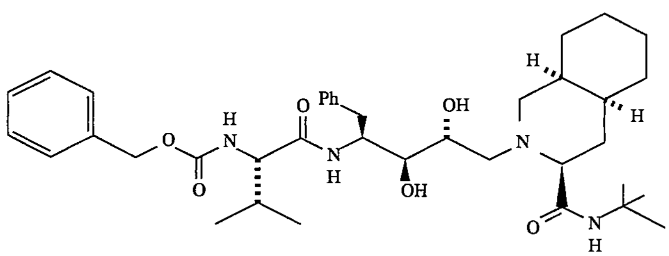 | −78.2 (1.01) [665.36] | 1.4 | 1.7 |
| 4 | 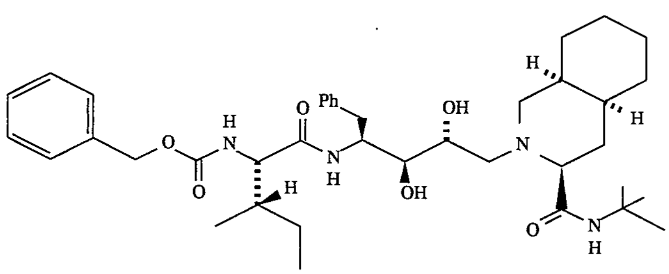 | −75.9 (0.94) [679.44] | 1.99 | 1.0 |
| 5 | 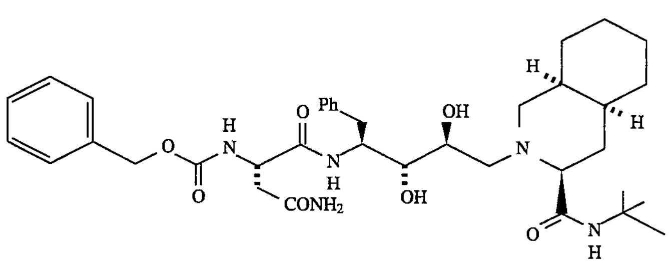 | +27.5 (0.27) [680.68] | >12.5 | >30 |

TABLE I-continued

| Ex. No. | STRUCTURE | $[\alpha]_D$ at 25° C. (g/100 ml) $[M^+ + H]$ | $IC_{50}$ (gag) μg/ml | $IC_{90}$ Cells μg/ml |
|---|---|---|---|---|
| 6 | (structure) | +74.0 (0.65) [701.48] | >12.5 | 10 |
| 7 | (structure) | −36.8 (0.97) [701.33] | 1.99 | 2.2 |
| 8 | (structure) | −74.0 (1.03) [680] | >12.5 | >30 |
| 9 | (structure) | −39.9 (0.98) [701] | >12.5 | 3.0 |

TABLE II

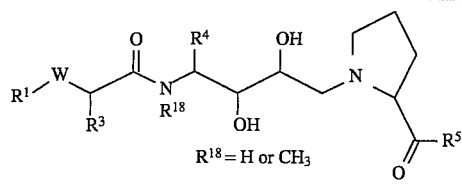

$R^{18}$ = H or $CH_3$

| Example Number | $R^1$ | W | $R^3$ | $R^4$ | $R^5$ |
| --- | --- | --- | --- | --- | --- |
| 10 | 2-pyridylmethyl | C(=O) | 2-propyl | benzyl | O-t-butyl |
| 11 | 2-pyridylmethyl | C(=O) | 2-butyl | 4-imidazolylmethyl | NH-t-butyl |
| 12 | benzyl | C(=O) | 2-butyl | cyclohexylmethyl | O-isopropyl |
| 13 | benzyl | C(=O) | 2-propyl | benzyl | NH-isopropyl |
| 14 | benzyl | C(=O) | 2-propyl | benzyl | O-cyclopropyl |
| 15 | benzyl | C(=O) | benzyl | benzyl | NH-cyclopropyl |
| 16 | n-propyl | C(=O) | 2-propyl | benzyl | O-t-butyl |
| 17 | naphthyl | C(=O) | 2-propyl | benzyl | NH-t-butyl |
| 18 | phenyl | C(=O) | 2-propyl | benzyl | O-isopropyl |
| 19 | thiophenyl | C(=O) | 2-propyl | benzyl | NH-isopropyl |
| 20 | trifluoromethyl | C(=O) | 2-propyl | benzyl | O-cyclopropyl |
| 21 | benzyl | C(=O)CH2 | 2-propyl | benzyl | NH-cyclopropyl |
| 22 | 2-pyridylmethyl | C(=O)NH | 2-butyl | benzyl | O-t-butyl |
| 23 | 2-quinaldyl | C(=O)NH | 2-butyl | benzyl | NH-t-butyl |
| 24 | 2-benzthiozyl | C(=O)NH | 2-butyl | benzyl | O-isopropyl |
| 25 | 2-thiophenylbutyl | C(=O)NH | 2-butyl | 4'-trifluoromethylbenzyl | NH-isopropyl |
| 26 | 2-benzimidazolyl | C(=O)NH | cyclobutyl | benzyl | O-cyclopropyl |
| 27 | benzyl | C(=O)NH | cyclobutylmethyl | benzyl | NH-cyclopropyl |
| 28 | methyl | C(=O)NH | 2-butyl | benzyl | O-t-butyl |
| 29 | phenylethyl | C(=O)NH | 2-butyl | benzyl | NH-t-butyl |
| 30 | benzyl | C(=O)NHNH | 2-propyl | benzyl | O-isopropyl |
| 31 | benzyl | C(=O)O | 2-propyl | benzyl | NH-isopropyl |
| 32 | benzyl | C(=S) | 2-propyl | benzyl | O-cyclopropyl |
| 33 | benzyl | C(=S)NH | 2-propyl | benzyl | NH-cyclopropyl |
| 34 | benzyl | C(Cl)=N | 2-propyl | benzyl | O-t-butyl |
| 35 | 2-pyridylmethyl | C(NHMe)=N | 2-propyl | benzyl | NH-t-butyl |
| 36 | 3-methylpropyl | C(NHMe)=N | 2-propyl | benzyl | O-isopropyl |
| 37 | benzyl | C(NHMe)=N | 2-propyl | benzyl | NH-isopropyl |
| 38 | benzyl | C(NHMe)=N | 2-propyl | benzyl | O-cyclopropyl |
| 39 | 2-pyridylethyl | C(OCH2CH3)=N | 2-propyl | benzyl | NH-cyclopropyl |
| | 3-naphthylmethyl | C(OCH2CH3)=N | 2-propyl | benzyl | O-t-butyl |
| | 4'-t-butylbenzyl | C(OCH2CH3)=N | 2-propyl | benzyl | NH-t-butyl |
| | benzyl | C(OCH2CH3)=N | 2-propyl | benzyl | O-isopropyl |
| | benzyl | C(OCH2CH3)=N | 2-propyl | 4'-ytrifluoromethylbenzyl | NH-isopropyl |
| | benzyl | C(OCH2CH3)=N | 2-propyl | 4'-chlorobenzyl | O-cyclopropyl |
| | benzyl | C(OCH2CH3)=N | 2-propyl | cyclohexylmethyl | NH-cyclopropyl |
| | benzyl | C(OCH2CH3)=N | cyclobutyl | benzyl | O-t-butyl |
| | benzyl | C(OCH2CH3)=N | cyclobutylmethyl | benzyl | NH-t-butyl |
| | benzyl | C(OCH2CH3)=N | cyclopropyl | benzyl | O-isopropyl |
| | benzyl | C(OCH3)=N | 2-propyl | benzyl | NH-isopropyl |
| | benzyl | CH2OCH2 | 2-propyl | benzyl | O-cyclopropyl |
| | benzyl | CH2CH2 | 2-propyl | benzyl | NH-cyclopropyl |
| | benzyl | CH2CHOH | 2-propyl | benzyl | O-t-butyl |
| | benzyl | CH2O | 2-propyl | benzyl | NH-t-butyl |
| | benzyl | CH2OH | 2-propyl | benzyl | O-isopropyl |
| | benzyl | CH=CH | 2-propyl | benzyl | NH-isopropyl |
| | benzyl | CHOHCH2 | 2-propyl | benzyl | O-cyclopropyl |
| | benzyl | CHOHCHOH | 2-propyl | benzyl | NH-cyclopropyl |
| | benzyl | HNC(=S)NH | 2-propyl | benzyl | O-t-butyl |
| | benzyl | HNSO2 | 2-butyl | benzyl | NH-t-butyl |
| | benzyl | HNSO2NH | 2-butyl | benzyl | O-isopropyl |
| | benzyl | N=N | 2-propyl | benzyl | NH-isopropyl |
| | benzyl | NH—NH | 2-propyl | benzyl | O-cyclopropyl |
| | (—CH2CH2CH2CH2—) | NHC(=O)NH | 2-butyl | benzyl | NH-cyclopropyl |
| | (—CH2CH2OCH2CH2—) | NHC(=O)NH | 2-butyl | benzyl | O-t-butyl |
| | 2-hydroxy-3,3-dimethylpropyl | NHC(=O)NH | 2-butyl | benzyl | NH-t-butyl |
| | 2-hydroxy-3,3-dimenthylpropyl | NHC(=O)NH | 2-butyl | benzyl | O-isopropyl |
| | 2-hydroxyindanylmethyl | NHC(=O)NH | 2-butyl | benzyl | NH-isopropyl |
| | 3,5-dimethoxyphenyl | NHC(=O)NHY | 2-butyl | benzyl | O-cyclopropyl |
| | 3-hydroxy-n-propyl | NHC(=O)NH | 2-butyl | benzyl | NH-cyclopropyl |
| | 4'-nitrobenzyl | NHC(=O)NH | 2-butyl | benzyl | O-t-butyl |

TABLE II-continued

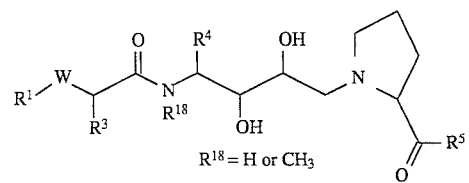

$R^{18}$ = H or $CH_3$

| Example Number | $R^1$ | W | $R^3$ | $R^4$ | $R^5$ |
| --- | --- | --- | --- | --- | --- |
| | 4-benzyloxyphenyl methyl | NHC(=O)NH | 2-butyl | benzyl | NH-t-butyl |
| | 4-cyano-n-butyl | NHC(=O)NH | 2-butyl | benzyl | O-isopropyl |
| | 4-phenoxyphenyl methyl | NHC(=O)NH | 2-butyl | benzyl | NH-isopropyl |
| | 4-t-butylphenylmethyl | NHC(=O)NH | 2-butyl | benzyl | O-cyclopropyl |
| | adamantyl | NHC(=O)NH | 2-butyl | benzyl | NH-cyclopropyl |
| | benzyl | NHC(=O)NH | 2-butyl | benzyl | O-t-butyl |
| | benzyl | NHC(=O)NH | 2-butyl | benzyl | NH-t-butyl |
| | benzyl | NHC(=O)NH | 2-propyl | benzyl | O-isopropyl |
| | benzyl | NHC(=O)NH | 2-propyl | 2-naphthylmethyl | NH-isopropyl |
| | benzyl | NHC(=O)NH | 2-propyl | 3-naphthylmethyl | O-cyclopropyl |
| | benzyl | NHC(=O)NH | 2-propyl | 1-adamantylmethyl | NH-cyclopropyl |
| | benzyl | NHC(=O)NH | 2-propyl | 4'-hydroxybenzyl | O-t-butyl |
| | benzyl | NHC(=O)NH | 2-propyl | 2-imidazolylethyl | NH-t-butyl |
| | 2-quinaldyl | NHC(=O)NH | 2-propyl | 4-pyridinylmethyl | O-isopropyl |
| | 2-benzthiozyl | NHC(=O)NH | 2-propyl | 4-bromophenyl | NH-isopropyl |
| | 2-thiophenylbutyl | NHC(=O)NH | 2-propyl | cycloheptylmethyl | O-cyclopropyl |
| | 2-benzimidazolyl | NHC(=O)NH | 2-propyl | 2-thiophenylmethyl | NH-cyclopropyl |
| | benzyl | NHC(=O)NH | 2-propyl | 3-pyrrazolylmethyl | O-t-butyl |
| | benzyl | NHC(=O)NH | 2-propyl | 3-(trifluoromethane-sulfonyl)propyl | NH-t-butyl |
| | benzyl | NHC(=O)NH | 2-propyl | 4-(1-methyl)piperidinyl-methyl | O-isopropyl |
| | benzyl | NHC(=O)NH | 2-thiazolylmethyl | benzyl | NH-isopropyl |
| | benzyl | NHC(=O)NH | benzyl | benzyl | O-cyclopropyl |
| | benzyl | NHC(=O)NH | CH2CF3 | benzyl | NH-cyclopropyl |
| | benzyl | NHC(=O)NH | CH2CH2C(=O)NH2 | benzyl | O-t-butyl |
| | benzyl | NHC(=O)NH | CH2CH2OH | benzyl | NH-t-butyl |
| | 2-quinaldyl | NHC(=O)NH | CH2CHOHCH3 | benzyl | O-isopropyl |
| | 2-benzthiozyl | NHC(=O)NH | cyclobutyl | benzyl | NH-isopropyl |
| | 2-thiophenylbutyl | NHC(=O)NH | cyclobutyl | benzyl | O-cyclopropyl |
| | 2-benzimidazolyl | NHC(=O)NH | cyclobutylmethyl | benzyl | NH-cyclopropyl |
| | benzyl | NHC(=O)NH | cyclopentylmethyl | benzyl | O-t-butyl |
| | benzyl | NHC(=O)NH | cyclopropyl | benzyl | NH-t-butyl |
| | benzyl | NHC(=O)NH | cyclopropylmethyl | benzyl | O-isopropyl |
| | cis-2-decahydronaphthyl-methyl | NHC(=O)NH | 2-butyl | benzyl | NH-isopropyl |
| | cis-2-decahydronaphthyl-methyl | NHC(=O)NH | 2-butyl | benzyl | O-cyclopropyl |
| | benzyl | O | 2-propyl | benzyl | NH-cyclopropyl |
| | (CH2CH2CH)CH2CH2 | OC(=O)NH | 2-butyl | benzyl | O-t-butyl |
| | 1-piperidylethyl | OC(=O)NH | 2-butyl | benzyl | NH-t-butyl |
| | 2-benzimidazolylmethyl | OC(=O)NH | 2-butyl | benzyl | O-isopropyl |
| | 2-naphthylmethyl | OC(=O)NH | 2-butyl | benzyl | NH-isopropyl |
| | 2-pyridylmethyl | OC(=O)NH | 2-butyl | benzyl | O-cyclopropyl |
| | 2-quinazolinylmethyl | OC(=O)NH | 2-butyl | benzyl | NH-cyclopropyl |
| | 3,4-methylenedioxy-phenylmethyl | OC(=O)NH | 2-butyl | benzyl | O-t-butyl |
| | 3-chlorobenzyl | OC(=O)NH | 2-butyl | benzyl | NH-t-butyl |
| | 3-phenylpropyl | OC(=O)NH | 2-butyl | benzyl | O-isopropyl |
| | 4'-acetamidobenzyl | OC(=O)NH | 2-butyl | benzyl | NH-isopropyl |
| | 4-imidazolylmethyl | OC(=O)NH | 2-butyl | benzyl | O-cyclopropyl |
| | 4-methanesulfonyl-benzyl | OC(=O)NH | 2-butyl | benzyl | NH-cyclopropyl |
| | 4-methoxybenzyl | OC(=O)NH | 2-butyl | benzyl | O-t-butyl |
| | 4-pyridylmethyl | OC(=O)NH | 2-butyl | benzyl | NH-t-butyl |
| | 4-trifluoro-methylbenzyl | OC(=O)NH | 2-butyl | benzyl | O-isopropyl |
| | 9-fluorenylmethyl | OC(=O)NH | 2-butyl | benzyl | NH-isopropyl |
| | adamantylmethyl | OC(=O)NH | 2-butyl | benzyl | O-cyclopropyl |
| | benzyl | OC(=O)NH | 1-methoxy-2-propyl | benzyl | NH-cyclopropyl |
| | benzyl | OC(=O)NH | 2'- | benzyl | O-t-butyl |

TABLE II-continued

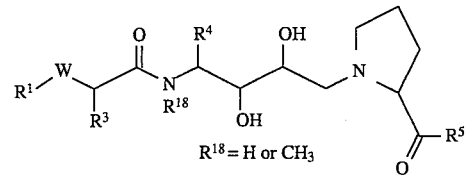

$R^{18}$ = H or CH3

| Example Number | $R^1$ | W | $R^3$ | $R^4$ | $R^5$ |
|---|---|---|---|---|---|
| | | | hydroxycyclopentyl methyl | | |
| | benzyl | OC(=O)NH | 2,2,2-trichloroethyl | benzyl | NH-t-butyl |
| | benzyl | OC(=O)NH | 2,2,2-trifluoroethyl | benzyl | O-isopropyl |
| | benzyl | OC(=O)NH | 2-butyl | benzyl | NH-isopropyl |
| | 2-quinaldyl | OC(=O)NH | 2-propyl | benzyl | O-cyclopropyl |
| | 2-benzthiozyl | OC(=O)NH | 2-propyl | benzyl | NH-cyclopropyl |
| | 2-thiophemylbutyl | OC(=O)NH | 2-propyl | 3-naphthylmethyl | O-t-butyl |
| | 2-benzimidazolyl | OC(=O)NH | 2-propyl | 4'-phenoxybenzyl | NH-t-butyl |
| | benzyl | OC(=O)NH | 2-propyl | 4'-benzyloxybenzyl | O-isopropyl |
| | benzyl | OC(=O)NH | 2-propyl | 4'-(5-tetrazolyl)benzyl | NH-isopropyl |
| | benzyl | OC(=O)NH | 2-propyl | 3',5'-bis(trifluoromethyl)benzyl | O-cyclopropyl |
| | benzyl | OC(=O)NH | 2-propyl | 4'-trifluoromethylbenzyl | NH-cyclopropyl |
| | benzyl | OC(=O)NH | 2-propyl | 2-phenylethyl | O-t-butyl |
| | benzyl | OC(=O)NH | 2-propyl | 2-benzimidazolylmethyl | NH-t-butyl |
| | benzyl | OC(=O)NH | 2-propyl | 2-(4-chlorophenyl)ethyl | O-isopropyl |
| | benzyl | OC(=O)NH | 2-propyl | 2-decahydronaphthylmethyl | NH-isopropyl |
| | benzyl | OC(=O)NH | 2-propyl | 2-(3,4-methylenedioxyphenyl)ethyl | O-cyclopropyl |
| | benzyl | OC(=O)NH | 3-(dimethylamino)-1-propyl | benzyl | NH-cyclopropyl |
| | benzyl | OC(=O)NH | benzyl | benzyl | O-t-butyl |
| | benzyl | OC(=O)NH | CH2NHC(=O)NHCH3 | 4-pyridylmethyl | NH-t-butyl |
| | benzyl | OC(=O)NH | CH2NHSO2CH3 | benzyl | O-isopropyl |
| | 2-quinaldyl | OC(=O)NH | cyclobutyl | benzyl | NH-isopropyl |
| | 2-benthiozyl | OC(=O)NH | cyclobutylmethyl | benzyl | O-cyclopropyl |
| | 2-thiophenylbutyl | OC(=O)NH | cyclopropyl | 2-pyridylmethyl | NH-cyclopropyl |
| | 2-benzimidazolyl | OC(=O)NH | cyclopropylmethyl | benzyl | O-t-butyl |
| | benzyl | OC(=O)NH | methyl | benzyl | NH-t-butyl |
| | CH3SO2CH2CH2 | OC(=O)NH | 2-butyl | benzyl | O-isopropyl |
| | cyclopentylethyl | OC(=O)NH | 2-butyl | 2-pyridylmethyl | NH-isopropyl |
| | F2HCOC6H4CH2 | OC(=O)NH | 2-butyl | 3-pyridylmethyl | O-cyclopropyl |
| | N,N-dimethylamino-3-propyl | OC(=O)NH | 2-butyl | benzyl | NH-cyclopropyl |
| | benzyl | OCH2 | 2-propyl | benzyl | O-t-butyl |
| | benzyl | OP(=O)(OMe)O | 2-propyl | 2-pyridylmethyl | NH-t-butyl |
| | benzyl | SO2 | 2-propyl | benzyl | O-isopropyl |
| | 2,4-difluorophenyl | SO2NH | 2-butyl | 2-pyridylmethyl | NH-isopropyl |
| | 4'-methylphenyl | SO2NH | 2-butyl | benzyl | O-cyclopropyl |
| | benzyl | SO2NH | 2-(methylamino)ethyl | benzyl | NH-cyclopropyl |
| | benzyl | SO2NH | 2-furanylmethyl | benzyl | O-t-butyl |
| | benzyl | SO2NH | 2-propyl | benzyl | NH-t-butyl |
| | benzyl | SO2NH | 2-propyl | benayl | O-isopropyl |
| | benzyl | SO2NH | 2-propyl | 3'-trifluoro-methylbenzyl | NH-isopropyl |
| | benayl | SO2NH | 2-propyl | 2',4'-difluorobenzyl | O-cyclopropyl |
| | benzyl | SO2NH | 2-propyl | 3-phenylpropyl | NH-cyclopropyl |
| | benzyl | SO2NH | 2-propyl | 1-pyrrolylethyl | O-t-butyl |
| | benzyl | SO2NH | 2-propyl | 2-(4-chlorophenyl)ethyl | NH-t-butyl |
| | benzyl | SO2NH | 2-propyl | 1-phenylethyl | O-isopropyl |
| | 2-quinaldyl | SO2NH | 3-hydroxy-1-propyl | 1-phenylethyl | NH-isopropyl |
| | 2-benzthiozyl | SO2NH | cyclobutyl | benzyl | O-cyclopropyl |
| | 2-thiophenylbutyl | SO2NH | cyclopropyl | benzyl | NH-cyclopropyl |
| | 2-benzimidazolyl | SO2NH | methylthiomethyl | 1-phenylethyl | O-t-butyl |
| | cyclohexylethyl | SO2NH | 2-butyl | 2-pyridylmethyl | NH-t-butyl |
| | nonafluorobutyl | SO2NH | 2-butyl | benzyl | O-isopropyl |
| | phenyl | SO2NH | 2-butyl | 2-pyridylmethyl | NH-isopropyl |
| | trifluoromethyl | SO2NH | 2-butyl | benzyl | O-cyclopropyl |
| | 2,4-difluorophenyl | SO2NHC(=O)NH | 2-butyl | benzyl | NH-cyclopropyl |
| | 4'-methylphenyl | SO2NHC(=O)NH | 2-(dimethylamino)ethyl | 3-pyridylmethyl | O-t-butyl |

TABLE II-continued

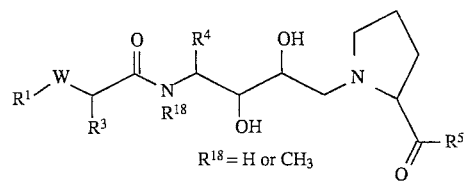

R¹⁸ = H or CH₃

| Example Number | R¹ | W | R³ | R⁴ | R⁵ |
|---|---|---|---|---|---|
| | 4'-methylphenyl | SO2NHC(=O)NH | 2-butyl | benzyl | NH-t-butyl |
| | 4'-methylphenyl | SO2NHC(=O)NH | 2-butyl | 4-pyridylmethyl | O-isopropyl |
| | 4'-methylphenyl | SO2NHC(=O)NH | benzyl | benzyl | NH-isopropyl |
| | 4'-methylphenyl | SO2NHC(=O)NH | CH2CH2OH | benzyl | O-cyclopropyl |
| | 4'-methylphenyl | SO2NHC(=O)NH | cyclobutyl | benzyl | NH-cyclopropyl |
| | 4'-methylphenyl | SO2NHC(=O)NH | cyclohexylmethyl | 4-pyridylmethyl | O-t-butyl |
| | 4'-methylphenyl | SO2NHC(=O)NH | cyclopropyl | benzyl | NH-t-butyl |
| | benzyl | SO2NHC(=O)NH | 2-butyl | benzyl | O-isopropyl |
| | cyclohexylethyl | SO2NHC(=O)NH | 2-butyl | 2-pyridylmethyl | NH-isopropyl |
| | methyl | SO2NHC(=O)NH | 2-butyl | benzyl | O-cyclopropyl |
| | nonafluorobutyl | SO2NHC(=O)NH | 2-butyl | benzyl | NH-cyclopropyl |
| | phenyl | SO2NHC(=O)NH | 2-butyl | 3-pyridylmethyl | O-t-butyl |
| | phenyl | SO2NHC(=O)NH | 2-butyl | benzyl | NH-t-butyl |
| | phenyl | SO2NHC(=O)NH | 2-butyl | 2'-chlorobenzyl | O-isopropyl |
| | phenyl | SO2NHC(=O)NH | 2-butyl | 3-naphthylmethyl | NH-isopropyl |
| | phenyl | SO2NHC(=O)NH | 2-butyl | 2-(4-fluorophenyl)ethyl | O-cyclopropyl |
| | 2-quinaldyl | SO2NHC(=O)NH | 2-butyl | 2-phenylethyl | NH-cyclopropyl |
| | 2-benzthiozyl | SO2NHC(=O)NH | 2-butyl | 3'-carbomethoxybenzyl | O-t-butyl |
| | 2-thiophenylbutyl | SO2NHC(=O)NH | 2-butyl | 2-pyridylmethyl | NH-t-butyl |
| | 2-benzimidazolyl | SO2NHC(=O)NH | cyclopropyl | benzyl | O-isopropyl |
| | trifluoromethyl | SO2NHC(=O)NH | 2-butyl | benzyl | NH-isopropyl |
| | trifluoromethyl | SO2NHC(=O)NH | 2-butyl | benzyl | O-cyclopropyl |
| | trifluoromethyl | SO2NHC(=O)NH | cyclobutyl | 3-pyridylmethyl | NH-cyclopropyl |
| | trifluoromethyl | SO2NHC(=O)NH | cyclopropyl | 4-pyridylmethyl | NH-t-butyl |

TABLE III

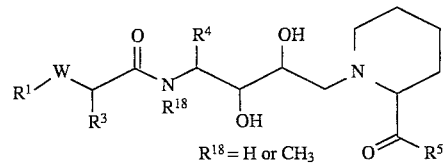

R¹⁸ = H or CH₃

| R¹ | W | R³ | R⁴ | R⁵ |
|---|---|---|---|---|
| 2-pyridylmethyl | C(=O) | 2-propyl | benzyl | O-t-butyl |
| 2-pyridylmethyl | C(=O) | 2-butyl | 4-imidazolylmethyl | NH-t-butyl |
| benzyl | C(=O) | 2-butyl | cyclohexylmethyl | O-isopropyl |
| benzyl | C(=O) | 2-propyl | benzyl | NH-isopropyl |
| benzyl | C(=O) | 2-propyl | benzyl | O-cyclopropyl |
| benzyl | C(=O) | benzyl | benzyl | NH-cyclopropyl |
| n-propyl | C(=O) | 2-propyl | benzyl | O-t-butyl |
| naphthyl | C(=O) | 2-propyl | benzyl | NH-t-butyl |
| phenyl | C(=O) | 2-propyl | benzyl | O-isopropyl |
| thiophenyl | C(=O) | 2-propyl | benzyl | NH-isopropyl |
| trifluoromethyl | C(=O) | 2-propyl | benzyl | O-cyclopropyl |
| benzyl | C(=O)CH2 | 2-propyl | benzyl | NH-cyclopropyl |
| 2-pyridylmethyl | C(=O)NH | 2-butyl | benzyl | O-t-butyl |
| 2-quinaldyl | C(=O)NH | 2-butyl | benzyl | NH-t-butyl |
| 2-benzthiozyl | C(=O)NH | 2-butyl | benzyl | O-isopropyl |
| 2-thiophenylbutyl | C(=O)NH | 2-butyl | 4'-trifluoromethylbenzyl | NH-isopropyl |
| 2-benzimidazolyl | C(=O)NH | cyclopropyl | benzyl | O-cyclopropyl |
| benzyl | C(=O)NH | cyclobutylmethyl | benzyl | NH-cyclopropyl |
| methyl | C(=O)NH | 2-butyl | benzyl | O-t-butyl |
| phenylmethyl | C(=O)NH | 2-butyl | benzyl | NH-t-butyl |
| benzyl | C(=O)NHNH | 2-propyl | benzyl | O-isopropyl |
| benzyl | C(=O)O | 2-propyl | benzyl | NH-isopropyl |
| benzyl | C(=S) | 2-propyl | benzyl | O-cyclopropyl |
| benzyl | C(=S)NH | 2-propyl | benzyl | NH-cyclopropyl |
| benzyl | C(Cl)=N | 2-propyl | benzyl | O-t-butyl |
| 2-pyridylmethyl | C(NHMe)=N | 2-propyl | benzyl | NH-t-butyl |
| 3-methylpropyl | C(NHMe)=N | 2-propyl | benzyl | O-isopropyl |

TABLE III-continued

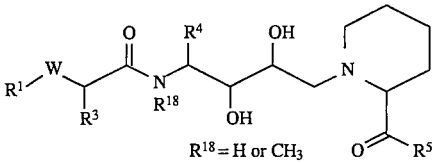

$R^{18} = H$ or $CH_3$

| R¹ | W | R³ | R⁴ | R⁵ |
|---|---|---|---|---|
| benzyl | C(NHMe)=N | 2-propyl | benzyl | NH-isopropyl |
| benzyl | C(NHMe)=N | 2-propyl | benzyl | O-cyclopropyl |
| 2-pyridylethyl | C(OCH2CH3)=N | 2-propyl | benzyl | NH-cyclopropyl |
| 3-naphthylmethyl | C(OCH2CH3)=N | 2-propyl | benzyl | O-t-butyl |
| 4'-t-butylbenzyl | C(OCH2CH3)=N | 2-propyl | benzyl | NH-t-butyl |
| benzyl | C(OCH2CH3)=N | 2-propyl | benzyl | O-isopropyl |
| benzyl | C(OCH2CH3)=N | 2-propyl | 4'-ytrifluoromethylbenzyl | NH-isopropyl |
| benzyl | C(OCH2CH3)=N | 2-propyl | 4'-chlorobenzyl | O-cyclopropyl |
| benzyl | C(OCH2CH3)=N | 2-propyl | cyclohexylmethyl | NH-cyclopropyl |
| benzyl | C(OCH2CH3)=N | cyclobutyl | benzyl | O-t-butyl |
| benzyl | C(OCH2CH3)=N | cyclobutylmethyl | benzyl | NH-t-butyl |
| benzyl | C(OCH2CH3)=N | cyclopropyl | benzyl | O-isopropyl |
| benzyl | C(OCH3)=N | 2-propyl | benzyl | NH-isopropyl |
| benzyl | CH2OCH2 | 2-propyl | benzyl | O-cyclopropyl |
| benzyl | CH2CH2 | 2-propyl | benzyl | NH-cyclopropyl |
| benzyl | CH2CHOH | 2-propyl | benzyl | O-t-butyl |
| benzyl | CH2O | 2-propyl | benzyl | NH-t-butyl |
| benzyl | CH2OH | 2-propyl | benzyl | O-isopropyl |
| benzyl | CH=CH | 2-propyl | benzyl | NH-isopropyl |
| benzyl | CHOHCH2 | 2-propyl | benzyl | O-cyclopropyl |
| benzyl | CHOHCHOH | 2-propyl | benzyl | NH-cyclopropyl |
| benzyl | HNC(=S)NH | 2-propyl | benzyl | O-t-butyl |
| benzyl | HNSO2 | 2-butyl | benzyl | NH-t-butyl |
| benzyl | HNSO2NH | 2-butyl | benzyl | O-isopropyl |
| benzyl | N=N | 2-propyl | benzyl | NH-isopropyl |
| benzyl | NH—NH | 2-propyl | benzyl | O-cyclopropyl |
| (—CH2CH2CH2CH2CH2—) | NHC(=O)NH | 2-butyl | benzyl | NH-cyclopropyl |
| (—CH2CH2OCH2CH2—) | NHC(=O)NH | 2-butyl | benzyl | O-t-butyl |
| 2-hydroxy-3,3-dimethylpropyl | NHC(=O)NH | 2-butyl | benzyl | NH-t-butyl |
| 2-hydroxy-3,3-dimethylpropyl | NHC(=O)NH | 2-butyl | benzyl | O-isopropyl |
| 2-hydroxyindanylmethyl | NHC(=O)NH | 2-butyl | benzyl | NH-isopropyl |
| 3,5-dimethoxyphenyl | NHC(=O)NH | 2-butyl | benzyl | O-cyclopropyl |
| 3-hydroxy-n-propyl | NHC(=O)NH | 2-butyl | benzyl | NH-cyclopropyl |
| 4'-nitrobenzyl | NHC(=O)NH | 2-butyl | benzyl | O-t-butyl |
| 4-benzyloxyphenylmethyl | NHC(=O)NH | 2-butyl | benzyl | NH-t-butyl |
| 4-cyano-n-butyl | NHC(=O)NH | 2-butyl | benzyl | O-isopropyl |
| 4-phenoxyphenylmethyl | NHC(=O)NH | 2-butyl | benzyl | NH-isopropyl |
| 4-t-butylphenylmethyl | NHC(=O)NH | 2-butyl | benzyl | O-cyclopropyl |
| adamantyl | NHC(=O)NH | 2-butyl | benzyl | NH-cyclopropyl |
| benzyl | NHC(=O)NH | 2-butyl | benzyl | O-t-butyl |
| benzyl | NHC(=O)NH | 2-butyl | benzyl | NH-t-butyl |
| benzyl | NHC(=O)NH | 2-propyl | benzyl | O-isopropyl |
| benzyl | NHC(=O)NH | 2-propyl | 2-naphthylmethyl | NH-isopropyl |
| benzyl | NHC(=O)NH | 2-propyl | 3-naphthylmethyl | O-cyclopropyl |
| benzyl | NHC(=O)NH | 2-propyl | 1-adamantylmethyl | NH-cyclopropyl |
| benzyl | NHC(=O)NH | 2-propyl | 4'-hydroxybenzyl | O-t-butyl |
| benzyl | NHC(=O)NH | 2-propyl | 2-imidazolylethyl | NH-t-butyl |
| 2-quinaldyl | NHC(=O)NH | 2-propyl | 4-pyridinylmethyl | O-isopropyl |
| 2-benzthiozyl | NHC(=O)NH | 2-propyl | 4-bromophenyl | NH-isopropyl |
| 2-thiophenylbutyl | NHC(=O)NH | 2-propyl | cycloheptylmethyl | O-cyclopropyl |
| 2-benzimidazolyl | NHC(=O)NH | 2-propyl | 2-thiophenylmethyl | NH-cyclopropyl |
| benzyl | NHC(=O)NH | 2-propyl | 3-pyrrazolylmethyl | O-t-butyl |
| benzyl | NHC(=O)NH | 2-propyl | 3-(trifluoromethanesulfonyl)propyl | NH-t-butyl |
| benzyl | NHC(=O)NH | 2-propyl | 4-(1-methyl)piperidinylmethyl | O-isopropyl |
| benzyl | NHC(=O)NH | 2-thiazolylmethyl | benzyl | NH-isopropyl |
| benzyl | NHC(=O)NH | benzyl | benzyl | O-cyclopropyl |
| benzyl | NHC(=O)NH | CH2CF3 | benzyl | NH-cyclopropyl |

TABLE III-continued

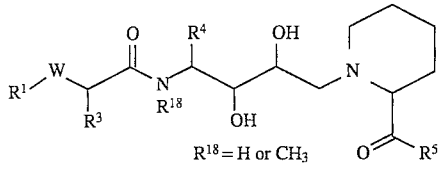

$R^{18}$ = H or CH₃

| R¹ | W | R³ | R⁴ | R⁵ |
|---|---|---|---|---|
| benzyl | NHC(=O)NH | CH2CH2C(=O)NH2 | benzyl | O-t-butyl |
| benzyl | NHC(=O)NH | CH2CH2OH | benzyl | NH-t-butyl |
| 2-quinaldyl | NHC(=O)NH | CH2CHOHCH3 | benzyl | O-isopropyl |
| 2-benzthiozyl | NHC(=O)NH | cyclobutyl | benzyl | NH-isopropyl |
| 2-thiophenylbutyl | NHC(=O)NH | cyclobutyl | benzyl | O-cyclopropyl |
| 2-benzimidazolyl | NHC(=O)NH | cyclobutylmethyl | benzyl | NH-cyclopropyl |
| benzyl | NHC(=O)NH | cyclopentylmethyl | benzyl | O-t-butyl |
| benzyl | NHC(=O)NH | cyclopropyl | benzyl | NH-t-butyl |
| benzyl | NHC(=O)NH | cyclopropylmethyl | benzyl | O-isopropyl |
| cis-2-decahydro-naphthylmethyl | NHC(=O)NH | 2-butyl | benzyl | NH-isopropyl |
| cis-2-decahydro-naphthylmethyl | NHC(=O)NH | 2-butyl | benzyl | O-cyclopropyl |
| benzyl | O | 2-propyl | benzyl | NH-cyclopropyl |
| (CH2CH2CH)CH2CH2 | OC(=O)NH | 2-butyl | benzyl | O-t-butyl |
| 1-piperidylethyl | OC(=O)NH | 2-butyl | benzyl | NH-t-butyl |
| 2-benzimidazolyl-methyl | OC(=O)NH | 2-butyl | benzyl | O-isopropyl |
| 2-naphthylmethyl | OC(=O)NH | 2-butyl | benzyl | NH-isopropyl |
| 2-pyridylmethyl | OC(=O)NH | 2-butyl | benzyl | O-cyclopropyl |
| 2-quinazolinyl-methyl | OC(=O)NH | 2-butyl | benzyl | NH-cyclopropyl |
| 3,4-methylene-dioxyphenylmethyl | OC(=O)NH | 2-butyl | benzyl | O-t-butyl |
| 3-chlorobenzyl | OC(=O)NH | 2-butyl | benzyl | NH-t-butyl |
| 3-phenylpropyl | OC(=O)NH | 2-butyl | benzyl | O-isopropyl |
| 4'-acetamidobenzyl | OC(=O)NH | 2-butyl | benzyl | NH-isopropyl |
| 4-imidazolylmethyl | OC(=O)NH | 2-butyl | benzyl | O-cyclopropyl |
| 4-methanesulfonylbenzyl | OC(=O)NH | 2-butyl | benzyl | NH-cyclopropyl |
| 4-methoxybenzyl | OC(=O)NH | 2-butyl | benzyl | O-t-butyl |
| 4-pyridylmethyl | OC(=O)NH | 2-butyl | benzyl | NH-t-butyl |
| 4-trifluoro-methylbenzyl | OC(=O)NH | 2-butyl | benzyl | O-isopropyl |
| 9-fluorenylmethyl | OC(=O)NH | 2-butyl | benzyl | NH-isopropyl |
| adamantylmethyl | OC(=O)NH | 2-butyl | benzyl | O-cyclopropyl |
| benzyl | OC(=O)NH | 1-methoxy-2-propyl | benzyl | NH-cyclopropyl |
| benzyl | OC(=O)NH | 2'-hydroxycyclopentylmethyl | benzyl | O-t-butyl |
| benzyl | OC(=O)NH | 2,2,2-trichloroethyl | benzyl | NH-t-butyl |
| benzyl | OC(=O)NH | 2,2,2-trifluoroethyl | benzyl | O-isopropyl |
| benzyl | OC(=O)NH | 2-butyl | benzyl | NH-isopropyl |
| 2-quinaldyl | OC(=O)NH | 2-propyl | benzyl | O-cyclopropyl |
| 2-benzthiozyl | OC(=O)NH | 2-propyl | benzyl | NH-cyclopropyl |
| 2-thiophenylbutyl | OC(=O)NH | 2-propyl | 3-naphthylmethyl | O-t-butyl |
| 2-benzimidazolyl | OC(=O)NH | 2-propyl | 4'-phenoxybenzyl | NH-t-butyl |
| benzyl | OC(=O)NH | 2-propyl | 4'-benzyloxybenzyl | O-isopropyl |
| benzyl | OC(=O)NH | 2-propyl | 4'-(5-tetrazolyl)benzyl | NH-isopropyl |
| benzyl | OC(=O)NH | 2-propyl | 3',5'-bis(trifluoromethyl)benzyl | O-cyclopropyl |
| benzyl | OC(=O)NH | 2-propyl | 4'-trifluoromethylbenzyl | NH-cyclopropyl |
| benzyl | OC(=O)NH | 2-propyl | 2-phenylethyl | O-t-butyl |
| benzyl | OC(=O)NH | 2-propyl | 2-benzimidazolylmethyl | NH-t-butyl |
| benzyl | OC(=O)NH | 2-propyl | 2-(4-chlorophenyl)ethyl | O-isopropyl |
| benzyl | OC(=O)NH | 2-propyl | 2-decahydronaphthyl-methyl | NH-isopropyl |
| benzyl | OC(=O)NH | 2-propyl | 2-(3,4-methylene-dioxyphenyl)ethyl | O-cyclopropyl |
| benzyl | OC(=O)NH | 3-(dimethylamino)-1-propyl | benzyl | NH-cyclopropyl |
| benzyl | OC(=O)NH | benzyl | benzyl | O-t-butyl |
| benzyl | OC(=O)NH | CH2NHC(=O)NHCH3 | 4-pyridylmethyl | NH-t-butyl |
| benzyl | OC(=O)NH | CH2NHSO2CH3 | benzyl | O-isopropyl |
| 2-quinaldyl | OC(=O)NH | cyclobutyl | benzyl | NH-isopropyl |
| 2-benzthiozyl | OC(=O)NH | cyclobutylmethyl | benzyl | O-cyclopropyl |
| 2-thiophenylbutyl | OC(=O)NH | cyclopropyl | 2-pyridylmethyl | NH-cyclopropyl |
| 2-benzimidazolyl | OC(=O)NH | cyclopropylmethyl | benzyl | O-t-butyl |

TABLE III-continued $$R^1-W-\underset{R^3}{CH}-\underset{O}{C(=O)}-\underset{R^{18}}{N}-\underset{OH}{CH}-\underset{R^4}{CH}-\underset{OH}{CH}-CH_2-N(\text{piperidine})-C(=O)-R^5$$

$R^{18} = H \text{ or } CH_3$

| R¹ | W | R³ | R⁴ | R⁵ |
|---|---|---|---|---|
| benzyl | OC(=O)NH | methyl | benzyl | NH-t-butyl |
| CH3SO2CH2CH2 | OC(=O)NH | 2-butyl | benzyl | O-isopropyl |
| cyclopentylethyl | OC(=O)NH | 2-butyl | 2-pyridylmethyl | NH-isopropyl |
| F2HCOC6H4CH2 | OC(=O)NH | 2-butyl | 3-pyridylmethyl | O-cyclopropyl |
| N,N-dimethylamino-3-propyl | OC(=O)NH | 2-butyl | benzyl | NH-cyclopropyl |
| benzyl | OCH2 | 2-propyl | benzyl | O-t-butyl |
| benzyl | OP(=O)(OMe)O | 2-propyl | 2-pyridylmethyl | NH-t-butyl |
| benzyl | SO2 | 2-propyl | benzyl | O-isopropyl |
| 2,4-difluorophenyl | SO2NH | 2-butyl | 2-pyridylmethyl | NH-isopropyl |
| 4'-methylphenyl | SO2NH | 2-butyl | benzyl | O-cyclopropyl |
| benzyl | SO2NH | 2-(methylamino)ethyl | benzyl | NH-cyclopropyl |
| benzyl | SO2NH | 2-furanylmethyl | benzyl | O-t-butyl |
| benzyl | SO2NH | 2-propyl | benzyl | NH-t-butyl |
| benzyl | SO2NH | 2-propyl | benzyl | O-isopropyl |
| benzyl | SO2NH | 2-propyl | 3'-trifluoromethyl-benzyl | NH-isopropyl |
| benzyl | SO2NH | 2-propyl | 2',4'-difluorobenzyl | O-cyclopropyl |
| benzyl | SO2NH | 2-propyl | 3-phenylpropyl | NH-cyclopropyl |
| benzyl | SO2NH | 2-propyl | 1-pyrrolylethyl | O-t-butyl |
| benzyl | SO2NH | 2-propyl | 2-(4-chlorophenyl)ethyl | NH-t-butyl |
| benzyl | SO2NH | 2-propyl | 1-phenylethyl | O-isopropyl |
| 2-quinaldyl | SO2NH | 3-hydroxy-1-propyl | 1-phenylethyl | NH-isopropyl |
| 2-benzthiozyl | SO2NH | cyclobutyl | benzyl | O-cyclopropyl |
| 2-thiophenylbutyl | SO2NH | cyclopropyl | benzyl | NH-cyclopropyl |
| 2-benzimidazolyl | SO2NH | methylthiomethyl | 1-phenylethyl | O-t-butyl |
| cyclohexylethyl | SO2NH | 2-butyl | 2-pyridylmethyl | NH-t-butyl |
| nonafluorobutyl | SO2NH | 2-butyl | benzyl | O-isopropyl |
| phenyl | SO2NH | 2-butyl | 2-pyridylmethyl | NH-isopropyl |
| trifluoromethyl | SO2NH | 2-butyl | benzyl | O-cyclopropyl |
| 2,4-difluorophenyl | SO2NHC(=O)NH | 2-butyl | benzyl | NH-cyclopropyl |
| 4'-methylphenyl | SO2NHC(=O)NH | 2-(dimethylamino)ethyl | 3-pyridylmethyl | O-t-butyl |
| 4'-methylphenyl | SO2NHC(=O)NH | 2-butyl | benzyl | NH-t-butyl |
| 4'-methylphenyl | SO2NHC(=O)NH | 2-butyl | 4-pyridylmethyl | O-isopropyl |
| 4'-methylphenyl | SO2NHC(=O)NH | benzyl | benzyl | NH-isopropyl |
| 4'-methylphenyl | SO2NHC(=O)NH | CH2CH2OH | benzyl | O-cyclopropyl |
| 4'-methylphenyl | SO2NHC(=O)NH | cyclobutyl | benzyl | NH-cyclopropyl |
| 4'-methylphenyl | SO2NHC(=O)NH | cyclohexylmethyl | 4-pyridylmethyl | O-t-butyl |
| 4'-methylphenyl | SO2NHC(=O)NH | cyclopropyl | benzyl | NH-t-butyl |
| benzyl | SO2NHC(=O)NH | 2-butyl | benzyl | O-isopropyl |
| cyclohexylethyl | SO2NHC(=O)NH | 2-butyl | 2-pyridylmethyl | NH-isopropyl |
| methyl | SO2NHC(=O)NH | 2-butyl | benzyl | O-cyclopropyl |
| nonafluorobutyl | SO2NHC(=O)NH | 2-butyl | benzyl | NH-cyclopropyl |
| phenyl | SO2NHC(=O)NH | 2-butyl | 3-pyridylmethyl | O-t-butyl |
| phenyl | SO2NHC(=O)NH | 2-butyl | benzyl | NH-t-butyl |
| phenyl | SO2NHC(=O)NH | 2-butyl | 2'-chlorobenzyl | O-isopropyl |
| phenyl | SO2NHC(=O)NH | 2-butyl | 3-naphthylmethyl | NH-isopropyl |
| phenyl | SO2NHC(=O)NH | 2-butyl | 2-(4-fluorophenyl)ethyl | O-cyclopropyl |
| 2-quinaldyl | SO2NHC(=O)NH | 2-butyl | 2-phenylethyl | NH-cyclopropyl |
| 2-benzthiozyl | SO2NHC(=O)NH | 2-butyl | 3'-carbomethoxybenzyl | O-t-butyl |
| 2-thiophenylbutyl | SO2NHC(=O)NH | 2-butyl | 2-pyridylmethyl | NH-t-butyl |
| 2-benzimidazolyl | SO2NHC(=O)NH | cyclopropyl | benzyl | O-isopropyl |
| trifluoromethyl | SO2NHC(=O)NH | 2-butyl | benzyl | NH-isopropyl |
| trifluoromethyl | SO2NHC(=O)NH | 2-butyl | benzyl | O-cyclopropyl |
| trifluoromethyl | SO2NHC(=O)NH | cyclobutyl | 3-pyridylmethyl | NH-cyclopropyl |
| trifluoromethyl | SO2NHC(=O)NH | cyclopropyl | 4-pyridylmethyl | NH-t-butyl |

TABLE IV

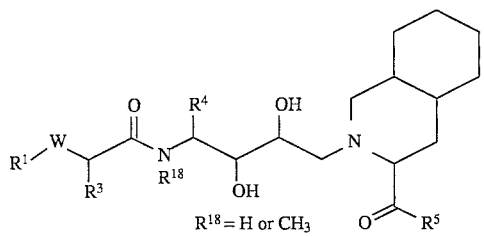

R<sup>18</sup> = H or CH3

| R¹ | W | R³ | R⁴ | R⁵ |
|---|---|---|---|---|
| 2-pyridylmethyl | C(=O) | 2-propyl | benzyl | O-t-butyl |
| 2-pyridylmethyl | C(=O) | 2-butyl | 4-imidazolylmethyl | NH-t-butyl |
| benzyl | C(=O) | 2-butyl | cyclohexylmethyl | O-isopropyl |
| benzyl | C(=O) | 2-propyl | benzyl | NH-isopropyl |
| benzyl | C(=O) | 2-propyl | benzyl | O-cyclopropyl |
| benzyl | C(=O) | benzyl | benzyl | NH-cyclopropyl |
| n-propyl | C(=O) | 2-propyl | benzyl | O-t-butyl |
| naphthyl | C(=O) | 2-propyl | benzyl | NH-t-butyl |
| phenyl | C(=O) | 2-propyl | benzyl | O-isopropyl |
| thiophenyl | C(=O) | 2-propyl | benzyl | NH-isopropyl |
| trifluoromethyl | C(=O) | 2-propyl | benzyl | O-cyclopropyl |
| benzyl | C(=O)CH2 | 2-propyl | benzyl | NH-cyclopropyl |
| 2-pyridylmethyl | C(=O)NH | 2-butyl | benzyl | O-t-butyl |
| 2-quinaldyl | C(=O)NH | 2-butyl | benzyl | NH-t-butyl |
| 2-benzthiozyl | C(=O)NH | 2-butyl | benzyl | O-isopropyl |
| 2-thiophenylbutyl | C(=O)NH | 2-butyl | 4'-trifluoromethylbenyl | NH-isopropyl |
| 2-benzimidazolyl | C(=O)NH | cyclobutyl | benzyl | O-cyclopropyl |
| benzyl | C(=O)NH | cyclobutylmethyl | benzyl | NH-cyclopropyl |
| methyl | C(=O)NH | 2-butyl | benzyl | O-t-butyl |
| phenylethyl | C(=O)NH | 2-butyl | benzyl | NH-t-butyl |
| benzyl | C(=O)NHNH | 2-propyl | benzyl | O-isopropyl |
| benzyl | C(=O)O | 2-propyl | benzyl | NH-isopropyl |
| benzyl | C(=S) | 2-propyl | benzyl | O-cyclopropyl |
| benzyl | C(=S)NH | 2-propyl | benzyl | NH-cyclopropyl |
| benzyl | C(Cl)=N | 2-propyl | benzyl | O-t-butyl |
| 2-pyridylmethyl | C(NHMe)=N | 2-propyl | benzyl | NH-t-butyl |
| 3-methylpropyl | C(NHMe)=N | 2-propyl | benzyl | O-isopropyl |
| benzyl | C(NHMe)=N | 2-propyl | benzyl | NH-isopropyl |
| benzyl | C(NHMe)=N | 2-propyl | benzyl | O-cyclopropyl |
| 2-pyridylethyl | C(OCH2CH3)=N | 2-propyl | benzyl | NH-cyclopropyl |
| 3-naphthylmethyl | C(OCH2CH3)=N | 2-propyl | benzyl | O-t-butyl |
| 4'-t-butylbenzyl | C(OCH2CH3)=N | 2-propyl | benzyl | NH-t-butyl |
| benzyl | C(OCH2CH3)=N | 2-propyl | benzyl | O-isopropyl |
| benzyl | C(OCH2CH3)=N | 2-propyl | 4'-ytrifluoromethylbenzyl | NH-isopropyl |
| benzyl | C(OCH2CH3)=N | 2-propyl | 4'-chlorobenzyl | O-cyclopropyl |
| benzyl | C(OCH2CH3)=N | 2-propyl | cyclohexylmethyl | NH-cyclopropyl |
| benzyl | C(OCH2CH3)=N | cyclobutyl | benzyl | O-t-butyl |
| benzyl | C(OCH2CH3)=N | cyclobutylmethyl | benzyl | NH-t-butyl |
| benzyl | C(OCH2CH3)=N | cyclopropyl | benzyl | O-isopropyl |
| benzyl | C(OCH3)=N | 2-propyl | benzyl | NH-isopropyl |
| benzyl | CH2OCH2 | 2-propyl | benzyl | O-cyclopropyl |
| benzyl | CH2CH2 | 2-propyl | benzyl | NH-cyclopropyl |
| benzyl | CH2CHOH | 2-propyl | benzyl | O-t-butyl |
| benzyl | CH2O | 2-propyl | benzyl | NH-t-butyl |
| benzyl | CH2OH | 2-propyl | benzyl | O-isopropyl |
| benzyl | CH=CH | 2-propyl | benzyl | NH-isopropyl |
| benzyl | CHOHCH2 | 2-propyl | benzyl | O-cyclopropyl |
| benzyl | CHOHCHOH | 2-propyl | benzyl | NH-cyclopropyl |
| benzyl | HNC(=S)NH | 2-propyl | benzyl | O-t-butyl |
| benzyl | HNSO2 | 2-butyl | benzyl | NH-t-butyl |
| benzyl | HNSO2NH | 2-butyl | benzyl | O-isopropyl |
| benzyl | N=N | 2-propyl | benzyl | NH-isopropyl |
| benzyl | NH—NH | 2-propyl | benzyl | O-cyclopropyl |
| (—CH2CH2CH2CH2CH2—) | NHC(=O)NH | 2-butyl | benzyl | NH-cyclopropyl |
| (—CH2CH2OCH2CH2—) | NHC(=O)NH | 2-butyl | benzyl | O-t-butyl |
| 2-hydroxy-3,3-dimethylpropyl | NHC(=O)NH | 2-butyl | benzyl | NH-t-butyl |
| 2-hydroxy-3,3-dimethylpropyl | NHC(=O)NH | 2-butyl | benzyl | O-isopropyl |
| 2-hydroxyindanylmethyl | NHC(=O)NH | 2-butyl | benzyl | NH-isopropyl |

TABLE IV-continued

R¹⁸ = H or CH₃

| R¹ | W | R³ | R⁴ | R⁵ |
|---|---|---|---|---|
| 3,5-dimethoxyphenyl | NHC(=O)NH | 2-butyl | benzyl | O-cyclopropyl |
| 3-hydroxy-n-propyl | NHC(=O)NH | 2-butyl | benzyl | NH-cyclopropyl |
| 4'-nitrobenzyl | NHC(=O)NH | 2-butyl | benzyl | O-t-butyl |
| 4-benzyloxyphenylmethyl | NHC(=O)NH | 2-butyl | benzyl | NH-t-butyl |
| 4-cyano-n-butyl | NHC(=O)NH | 2-butyl | benzyl | O-isopropyl |
| 4-phenoxyphenylmethyl | NHC(=O)NH | 2-butyl | benzyl | NH-isopropyl |
| 4-t-butylphenylmethyl | NHC(=O)NH | 2-butyl | benzyl | O-cyclopropyl |
| adamantyl | NHC(=O)NH | 2-butyl | benzyl | NH-cyclopropyl |
| benzyl | NHC(=O)NH | 2-butyl | benzyl | O-t-butyl |
| benzyl | NHC(=O)NH | 2-butyl | benzyl | NH-t-butyl |
| benzyl | NHC(=O)NH | 2-propyl | benzyl | O-isopropyl |
| benzyl | NHC(=O)NH | 2-propyl | 2-naphthylmethyl | NH-isopropyl |
| benzyl | NHC(=O)NH | 2-propyl | 3-naphthylmethyl | O-cyclopropyl |
| benzyl | NHC(=O)NH | 2-propyl | 1-adamantylmethyl | NH-cyclopropyl |
| benzyl | NHC(=O)NH | 2-propyl | 4'-hydroxybenzyl | O-t-butyl |
| benzyl | NHC(=O)NH | 2-propyl | 2-imidazolylethyl | NH-t-butyl |
| 2-quinaldyl | NHC(=O)NH | 2-propyl | 4-pyridinylmethyl | O-isopropyl |
| 2-benzthiozyl | NHC(=O)NH | 2-propyl | 4-bromophenyl | NH-isopropyl |
| 2-thiophenylbutyl | NHC(=O)NH | 2-propyl | cycloheptylmethyl | O-cyclopropyl |
| 2-benzimidazolyl | NHC(=O)NH | 2-propyl | 2-thiophenylmethyl | NH-cyclopropyl |
| benzyl | NHC(=O)NH | 2-propyl | 3-pyrrazolylmethyl | O-t-butyl |
| benzyl | NHC(=O)NH | 2-propyl | 3-(trifluoromethanesulfonyl)propyl | NH-t-butyl |
| benzyl | NHC(=O)NH | 2-propyl | 4-(1-methyl)piperidinylmethyl | O-isopropyl |
| benzyl | NHC(=O)NH | 2-thiazolylmethyl | benzyl | NH-isopropyl |
| benzyl | NHC(=O)NH | benzyl | benzyl | O-cyclopropyl |
| benzyl | NHC(=O)NH | CH2CF3 | benzyl | NH-cyclopropyl |
| benzyl | NHC(=O)NH | CH2CH2C(=O)NH2 | benzyl | O-t-butyl |
| benzyl | NHC(=O)NH | CH2CH2OH | benzyl | NH-t-butyl |
| 2-quinaldyl | NHC(=O)NH | CH2CHOHCH3 | benzyl | O-isopropyl |
| 2-benzthiozyl | NHC(=O)NH | cyclobutyl | benzyl | NH-isopropyl |
| 2-thiophenylbutyl | NHC(=O)NH | cyclobutyl | benzyl | O-cyclopropyl |
| 2-benzimidazolyl | NHC(=O)NH | cyclobutylmethyl | benzyl | NH-cyclopropyl |
| benzyl | NHC(=O)NH | cyclopentylmethyl | benzyl | O-t-butyl |
| benzyl | NHC(=O)NH | cyclopropyl | benzyl | NH-t-butyl |
| benzyl | NHC(=O)NH | cyclopropylmethyl | benzyl | O-isopropyl |
| cis-2-decahydronaphthylmethyl | NHC(=O)NH | 2-butyl | benzyl | NH-isopropyl |
| cis-2-decahydronaphthylmethyl | NHC(=O)NH | 2-butyl | benzyl | O-cyclopropyl |
| benzyl | O | 2-propyl | benzyl | NH-cyclopropyl |
| (CH2CH2CH)CH2CH2 | OC(=O)NH | 2-butyl | benzyl | O-t-butyl |
| 1-piperidylethyl | OC(=O)NH | 2-butyl | benzyl | NH-t-butyl |
| 2-benzimidazolylmethyl | OC(=O)NH | 2-butyl | benzyl | O-isopropyl |
| 2-naphthylmethyl | OC(=O)NH | 2-butyl | benzyl | NH-isopropyl |
| 2-pyridylmethyl | OC(=O)NH | 2-butyl | benzyl | O-cyclopropyl |
| 2-quinazolinylmethyl | OC(=O)NH | 2-butyl | benzyl | NH-cyclopropyl |
| 3,4-methylenedioxyphenylmethyl | OC(=O)NH | 2-butyl | benzyl | O-t-butyl |
| 3-chlorobenzyl | OC(=O)NH | 2-butyl | benzyl | NH-t-butyl |
| 3-phenylpropyl | OC(=O)NH | 2-butyl | benzyl | O-isopropyl |
| 4'-acetamidobenzyl | OC(=O)NH | 2-butyl | benzyl | NH-isopropyl |
| 4-imidazolylmethyl | OC(=O)NH | 2-butyl | benzyl | O-cyclopropyl |
| 4-methanesulfonylbenzyl | OC(=O)NH | 2-butyl | benzyl | NH-cyclopropyl |
| 4-methoxybenzyl | OC(=O)NH | 2-butyl | benzyl | O-t-butyl |
| 4-pyridylmethyl | OC(=O)NH | 2-butyl | benzyl | NH-t-butyl |
| 4-trilfuoromethylbenzyl | OC(=O)NH | 2-butyl | benzyl | O-isopropyl |
| 9-fluorenylmethyl | OC(=O)NH | 2-butyl | benzyl | NH-isopropyl |

TABLE IV-continued $R^{18}$ = H or CH3

| R¹ | W | R³ | R⁴ | R⁵ |
|---|---|---|---|---|
| adamantylmethyl | OC(=O)NH | 2-butyl | benzyl | O-cyclopropyl |
| benzyl | OC(=O)NH | 1-methoxy-2-propyl | benzyl | NH-cyclopropyl |
| benzyl | OC(=O)NH | 2'-hydroxycyclopentylmethyl | benzyl | O-t-butyl |
| benzyl | OC(=O)NH | 2,2,2-trichloroethyl | benzyl | NH-t-butyl |
| benzyl | OC(=O)NH | 2,2,2-trifluoroethyl | benzyl | O-isopropyl |
| benzyl | OC(=O)NH | 2-butyl | benzyl | NH-isopropyl |
| 2-quinaldyl | OC(=O)NH | 2-propyl | benzyl | O-cyclopropyl |
| 2-benzthiozyl | OC(=O)NH | 2-propyl | benzyl | NH-cyclopropyl |
| 2-thiophenylbutyl | OC(=O)NH | 2-propyl | 3-naphthylmethyl | O-t-butyl |
| 2-benzimidazolyl | OC(=O)NH | 2-propyl | 4'-phenoxybenzyl | NH-t-butyl |
| benzyl | OC(=O)NH | 2-propyl | 4'-benzyloxybenzyl | O-isopropyl |
| benzyl | OC(=O)NH | 2-propyl | 4'-(5-tetrazolyl)benzyl | NH-isopropyl |
| benzyl | OC(=O)NH | 2-propyl | 3',5'-bis(trifluoromethyl)benzyl | O-cyclopropyl |
| benzyl | OC(=O)NH | 2-propyl | 4'-trifluoromethylbenzyl | NH-cyclopropyl |
| benzyl | OC(=O)NH | 2-propyl | 2-phenylethyl | O-t-butyl |
| benzyl | OC(=O)NH | 2-propyl | 2-benzimidazolylmethyl | NH-t-butyl |
| benzyl | OC(=O)NH | 2-propyl | 2-(4-chlorophenyl)ethyl | O-isopropyl |
| benzyl | OC(=O)NH | 2-propyl | 2-decahydronaphthylmethyl | NH-isopropyl |
| benzyl | OC(=O)NH | 2-propyl | 2-(3,4-methylenedioxyphenyl)ethyl | O-cyclopropyl |
| benzyl | OC(=O)NH | 3-(dimethylamino)-1-propyl | benzyl | NH-cyclopropyl |
| benzyl | OC(=O)NH | benzyl | benzyl | O-t-butyl |
| benzyl | OC(=O)NH | CH2NHC(=O)NHCH3 | 4-pyridylmethyl | NH-t-butyl |
| benzyl | OC(=O)NH | CH2NHSO2CH3 | benzyl | O-isopropyl |
| 2-quinaldyl | OC(=O)NH | cyclobutyl | benzyl | NH-isopropyl |
| 2-benzthiozyl | OC(=O)NH | cyclobutylmethyl | benzyl | O-cyclopropyl |
| 2-thiophenylbutyl | OC(=O)NH | cyclopropyl | 2-pyridylmethyl | NH-cyclopropyl |
| 2-benzimidazolyl | OC(=O)NH | cyclopropylmethyl | benzyl | O-t-butyl |
| benzyl | OC(=O)NH | methyl | benzyl | NH-t-butyl |
| CH3SO2CH2CH2 | OC(=O)NH | 2-butyl | benzyl | O-isopropyl |
| cyclopentylethyl | OC(=O)NH | 2-butyl | 2-pyridylmethyl | NH-isopropyl |
| F2HCOC6H4CH2 | OC(=O)NH | 2-butyl | 3-pyridylmethyl | O-cyclopropyl |
| N,N-dimethylamino-3-propyl | OC(=O)NH | 2-butyl | benzyl | NH-cyclopropyl |
| benzyl | OCH2 | 2-propyl | benzyl | O-t-butyl |
| benzyl | OP(=O)(OMe)O | 2-propyl | 2-pyridylmethyl | NH-t-butyl |
| benzyl | SO2 | 2-propyl | benzyl | O-isopropyl |
| 2,4-difluorophenyl | SO2NH | 2-butyl | 2-pyridylmethyl | NH-isopropyl |
| 4'-methylphenyl | SO2NH | 2-butyl | benzyl | O-cyclopropyl |
| benzyl | SO2NH | 2-(methylamino)ethyl | benzyl | NH-cyclopropyl |
| benzyl | SO2NH | 2-furanylmethyl | benzyl | O-t-butyl |
| benzyl | SO2NH | 2-propyl | benzyl | NH-t-butyl |
| benzyl | SO2NH | 2-propyl | benzyl | O-isopropyl |
| benzyl | SO2NH | 2-propyl | 3'-trifluoromethylbenyl | NH-isopropyl |
| benzyl | SO2NH | 2-propyl | 2',4'-difluorobenzyl | O-cyclopropyl |
| benzyl | SO2NH | 2-propyl | 3-phenylpropyl | NH-cyclopropyl |
| benzyl | SO2NH | 2-propyl | 1-pyrrolylethyl | O-t-butyl |
| benzyl | SO2NH | 2-propyl | 2-(4-chlorophenyl)ethyl | NH-t-butyl |
| benzyl | SO2NH | 2-propyl | 1-phenylethyl | O-isopropyl |
| 2-quinaldyl | SO2NH | 3-hydroxy-1-propyl | 1-phenylethyl | NH-isopropyl |
| 2-benzthiozyl | SO2NH | cyclobutyl | benzyl | O-cyclopropyl |
| 2-thiophenylbutyl | SO2NH | cyclopropyl | benzyl | NH-cyclopropyl |
| 2-benzimidazolyl | SO2NH | methylthiomethyl | 1-phenylethyl | O-t-butyl |
| cyclohexylethyl | SO2NH | 2-butyl | 2-pyridylmethyl | NH-t-butyl |
| nonafluorobutyl | SO2NH | 2-butyl | benzyl | O-isopropyl |
| phenyl | SO2NH | 2-butyl | 2-pyridylmethyl | NH-isopropyl |
| trifluoromethyl | SO2NH | 2-butyl | benzyl | O-cyclopropyl |
| 2,4-difluorophenyl | SO2NHC(=O)NH | 2-butyl | benzyl | NH-cyclopropyl |
| 4'-methylphenyl | SO2NHC(=O)NH | 2-(dimethylamino) | 3-pyridylmethyl | O-t-butyl |

TABLE IV-continued

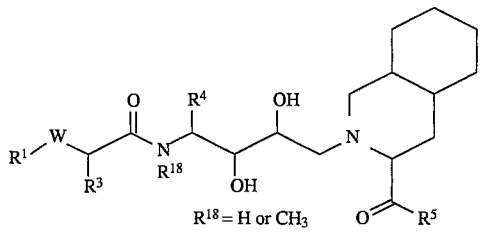

R18 = H or CH3

| R¹ | W | R³ | R⁴ | R⁵ |
|---|---|---|---|---|
| | | ethyl | | |
| 4'-methylphenyl | SO2NHC(=O)NH | 2-butyl | benzyl | NH-t-butyl |
| 4'-methylphenyl | SO2NHC(=O)NH | 2-butyl | 4-pyridylmethyl | O-isopropyl |
| 4'-methylphenyl | SO2NHC(=O)NH | benzyl | benzyl | NH-isopropyl |
| 4'-methylphenyl | SO2NHC(=O)NH | CH2CH2OH | benzyl | O-cyclopropyl |
| 4'-methylphenyl | SO2NHC(=O)NH | cyclobutyl | benzyl | NH-cyclopropyl |
| 4'-methylphenyl | SO2NHC(=O)NH | cyclohexylmethyl | 4-pyridylmethyl | O-t-butyl |
| 4'-methylphenyl | SO2NHC(=O)NH | cyclopropyl | benzyl | NH-t-butyl |
| benzyl | SO2NHC(=O)NH | 2-butyl | benzyl | O-isopropyl |
| cyclohexylethyl | SO2NHC(=O)NH | 2-butyl | 2-pyridylmethyl | NH-isopropyl |
| methyl | SO2NHC(=O)NH | 2-butyl | benzyl | O-cyclopropyl |
| nonafluorobutyl | SO2NHC(=O)NH | 2-butyl | benzyl | NH-cyclopropyl |
| phenyl | SO2NHC(=O)NH | 2-butyl | 3-pyridylmethyl | O-t-butyl |
| phenyl | SO2NHC(=O)NH | 2-butyl | benzyl | NH-t-butyl |
| phenyl | SO2NHC(=O)NH | 2-butyl | 2'-chlorobenzyl | O-isopropyl |
| phenyl | SO2NHC(=O)NH | 2-butyl | 3-naphthylmethyl | NH-isopropyl |
| phenyl | SO2NHC(=O)NH | 2-butyl | 2-(4-fluorophenyl)ethyl | O-cyclopropyl |
| 2-quinaldyl | SO2NHC(=O)NH | 2-butyl | 2-phenylethyl | NH-cyclopropyl |
| 2-benzthiozyl | SO2NHC(=O)NH | 2-butyl | 3'-carbomethoxybenzyl | O-t-butyl |
| 2-thiophenylbutyl | SO2NHC(=O)NH | 2-butyl | 2-pyridylmethyl | NH-t-butyl |
| 2-benzimidazolyl | SO2NHC(=O)NH | cyclopropyl | benzyl | O-isopropyl |
| trifluoromethyl | SO2NHC(=O)NH | 2-butyl | benzyl | NH-isopropyl |
| trifluoromethyl | SO2NHC(=O)NH | 2-butyl | benzyl | O-cyclopropyl |
| trifluoromethyl | SO2NHC(=O)NH | cyclobutyl | 3-pyridylmethyl | NH-cyclopropyl |
| trifluoromethyl | SO2NHC(=O)NH | cyclopropyl | 4-pyridylmethyl | NH-t-butyl |

TABLE V

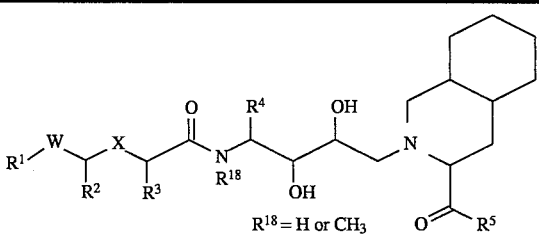

R18 = H or CH3

| R¹ | W | X | R² | R³ | R⁴ | R⁵ |
|---|---|---|---|---|---|---|
| benzyl | C(=O)NH | C(=O)NH | benzyl | 2-butyl | benzyl | O-t-butyl |
| benzyl | C(=O)NH | C(=O)O | benzyl | 2-butyl | benzyl | NH-t-butyl |
| benzyl | C(=O)NH | C(=O) | benzyl | 2-butyl | 2-pyridyl-methyl | O-isopropyl |
| benzyl | C(=O)NH | CH2C(=O) | benzyl | 2-butyl | benzyl | NH-isopropyl |
| benzyl | C(=O)NH | CH2C(=O)CH2 | benzyl | 2-butyl | 3-pyridyl-methyl | O-cyclopropyl |
| benzyl | C(=O)NH | C(=O)CH2 | benzyl | 2-butyl | benzyl | NH-cyclopropyl |
| benzyl | C(=O)NH | SO2NH | benzyl | 2-butyl | benzyl | O-t-butyl |
| benzyl | C(=O)NH | SO2 | benzyl | 2-butyl | 4-pyridyl-methyl | NH-t-butyl |
| benzyl | C(=O)NH | CH2OCH2 | benzyl | 2-butyl | benzyl | O-isopropyl |
| benzyl | C(=O)NH | CH2O | benzyl | 2-butyl | benzyl | NH-isopropyl |
| benzyl | C(=O)NH | CH2NCH3 | benzyl | 2-butyl | 2-pyridyl-methyl | O-cyclopropyl |
| benzyl | C(=O)NH | CH2NH | benzyl | 2-butyl | benzyl | NH-cyclopropyl |
| benzyl | C(=O)NH | CH2CH2 | benzyl | 2-butyl | benzyl | O-t-butyl |
| benzyl | C(=O)NH | CH=CH | benzyl | 2-butyl | 3-pyridyl-methyl | NH-t-butyl |
| benzyl | C(=O)NH | CH(OH)CH(OH) | benzyl | 2-butyl | benzyl | O-isopropyl |
| benzyl | C(=O)NH | CH(OH)CH2 | benzyl | 2-butyl | benzyl | NH-isopropyl |
| benzyl | C(=O)NH | CH2CH(OH) | benzyl | 2-butyl | benzyl | O-cyclopropyl |
| benzyl | C(=O)NH | CH(OH) | benzyl | 2-butyl | benzyl | NH-cyclopropyl |
| benzyl | C(=O)NH | C(−N[Me]2)=N | benzyl | 2-butyl | benzyl | O-t-butyl |
| benzyl | C(=O)NH | C(−OEt)=N | benzyl | 2-butyl | benzyl | NH-t-butyl |
| benzyl | C(=O)NH | C(Cl−)=N | benzyl | 2-butyl | 2-pyridyl-methyl | O-isopropyl |
| benzyl | C(=O)NH | SO2NH | benzyl | 2-butyl | benzyl | NH-isopropyl |

TABLE V-continued

Structure: $R^1-W-CHR^2-X-C(=O)-N(R^{18})-CHR^4-CH(OH)-CH(OH)-CH_2-N$(decahydroisoquinoline-C(=O)-$R^5$), with $R^{18}$ = H or CH₃, and $R^3$ on the carbon bearing $R^2$.

| R¹ | W | X | R² | R³ | R⁴ | R⁵ |
|---|---|---|---|---|---|---|
| benzyl | NHC(=O)NH | C(=O)NH | benzyl | 2-butyl | benzyl | O-cyclopropyl |
| 2-pyridylmethyl | NHC(=O)NH | C(=O)NH | benzyl | 2-butyl | 3-pyridyl-methyl | NH-cyclopropyl |
| 2-pyrimidinyl | NHC(=O)NH | C(=O)NH | benzyl | 2-butyl | benzyl | O-t-butyl |
| benzyl | NHC(=O)NH | C(=O)NH | 3-(methylamino)propyl | 2-butyl | benzyl | NH-t-butyl |
| naphthyl | NHC(=O)NH | C(=O)NH | benzyl | cyclopropyl | benzyl | O-isopropyl |
| benzyl | NHC(=O)NH | C(=O)NH | benzyl | cyclopropyl | 4-chlorobenzyl | NH-isopropyl |
| benzyl | NHC(=O)NH | C(=O)NH | benzyl | 2-butyl | 4-pyridyl | O-cyclopropyl |
| benzyl | NHC(=O)NH | C(=O)NH | 2-acetamido | 2-butyl | benzyl | NH-cyclopropyl |
| benzyl | NHC(=O)NH | C(=O)NH | 2-(dimethyl-aminoethyl) | 2-propyl | benzyl | NH-t-butyl |
| benzyl | NHC(=O)NH | C(=O)NH | benzyl | 2-butyl | benzyl | O-t-butyl |
| benzyl | NHC(=O)NH | SO2NH | benzyl | 2-butyl | benzyl | NH-t-butyl |
| benzyl | NHC(=O)NH | SO2NH | 3-(methylamino)propyl | n-propyl | benzyl | O-isopropyl |
| benzyl | NHC(=O)NH | SO2NH | isobutyl | 2-propyl | benzyl | NH-isopropyl |
| naphthyl | NHC(=O)NH | SO2NH | benzyl | 2-butyl | benzyl | O-cyclopropyl |
| benzyl | NHC(=O)NH | SO2NH | benzyl | 2-butyl | benzyl | NH-cyclopropyl |
| benzyl | OC(=O)NH | C(=O)NH | benzyl | 2-butyl | 2-pyridyl-methyl | O-t-butyl |
| 2-pyridylmethyl | OC(=O)NH | C(=O)O | benzyl | 2-butyl | benzyl | NH-t-butyl |
| benzyl | OC(=O)NH | C(=O) | benzyl | 2-butyl | benzyl | O-isopropyl |
| benzyl | OC(=O)NH | CH2C(=O) | benzyl | 2-butyl | benzyl | NH-isopropyl |
| benzyl | OC(=O)NH | CH2C(=O)CH2 | benzyl | 2-butyl | benzyl | O-cyclopropyl |
| benzyl | OC(=O)NH | C(=O)CH2 | benzyl | 2-butyl | benzyl | NH-cyclopropyl |
| benzyl | OC(=O)NH | SO2NH | benzyl | 2-butyl | benzyl | O-t-butyl |

TABLE VI

Structure: $R^1-W-CHR^3-SO_2-N(R^{18})-CHR^4-CH(OH)-CH(OH)-CH_2-N$(decahydroisoquinoline-C(=O)-$R^5$), $R^{18}$ = H or CH₃.

| R¹ | W | R³ | R⁴ | R⁵ |
|---|---|---|---|---|
| benzyl | SO2NH | 2-propyl | 1-phenylethyl | O-t-butyl |
| benzyl | SO2NH | 3-hydroxy-1-propyl | 1-phenylethyl | NH-t-butyl |
| benzyl | SO2NH | methylthiomethyl | 1-phenylethyl | O-isopropyl |
| phenyl | SO2NHC(=O)NH | 2-butyl | 2-phenylethyl | NH-isopropyl |
| phenyl | SO2NHC(=O)NH | 2-butyl | 3'-carbomethoxybenzyl | O-cyclopropyl |
| benzyl | OC(=O)NH | 2-propyl | 3-naphthylmethyl | NH-cyclopropyl |
| benzyl | OC(=O)NH | 2-propyl | 4'-(5-tetrazolyl)benzyl | NH-t-butyl |
| benzyl | OC(=O)NH | 2-propyl | 4'-benzyloxybenzyl | O-t-butyl |
| benzyl | OC(=O)NH | 2-propyl | 4'-phenoxybenzyl | NH-isopropyl |
| benzyl | C(=O)NH | 2-butyl | 4'-trifluoromethylbenzyl | O-isopropyl |
| 2-pyridylmethyl | C(=O)NH | 2-butyl | benzyl | NH-isopropyl |
| benzyl | C(=O)NH | 2-butyl | benzyl | O-cyclopropyl |
| benzyl | C(=O)NH | 2-butyl | 2-pyridylmethyl | NH-cyclopropyl |
| benzyl | C(=O)NH | cyclobutyl | benzyl | O-t-butyl |
| benzyl | C(=O)NH | cyclobutylmethyl | benzyl | NH-t-butyl |
| methyl | C(=O)NH | 2-butyl | benzyl | O-isopropyl |
| phenylethyl | C(=O)NH | 2-butyl | 3-pyridylmethyl | NH-isopropyl |
| benzyl | C(=O)NHNH | 2-propyl | benzyl | O-cyclopropyl |
| benzyl | C(=O)O | 2-propyl | benzyl | NH-cyclopropyl |
| benzyl | CH2OCH2 | 2-propyl | benzyl | O-t-butyl |
| benzyl | CH2CH2 | 2-propyl | 4-pyridylmethyl | NH-t-butyl |
| benzyl | CH2O | 2-propyl | benzyl | O-isopropyl |

TABLE VI-continued

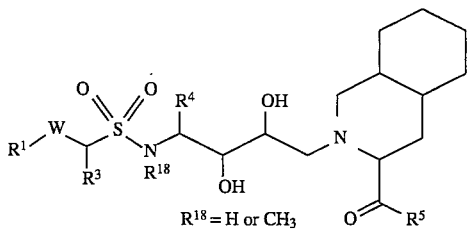

$R^{18}$ = H or CH$_3$

| R$^1$ | W | R$^3$ | R$^4$ | R$^5$ |
|---|---|---|---|---|
| benzyl | CH=CH | 2-propyl | benzyl | NH-isopropyl |
| benzyl | HNSO2NH | 2-butyl | benzyl | O-cyclopropyl |
| benzyl | N=N | 2-propyl | benzyl | NH-cyclopropyl |
| benzyl | NH—NH | 2-propyl | benzyl | NH-t-butyl |
| adamantyl | NHC(=O)NH | 2-butyl | 2-pyridylmethyl | O-t-butyl |
| benzyl | NHC(=O)NH | 2-butyl | benzyl | NH-t-butyl |
| benzyl | NHC(=O)NH | 2-butyl | benzyl | O-isopropyl |
| benzyl | NHC(=O)NH | 2-propyl | benzyl | NH-isopropyl |
| benzyl | NHC(=O)NH | benzyl | 3-pyridylmethyl | O-cyclopropyl |
| benzyl | NHC(=O)NH | CH2CF3 | benzyl | NH-cyclopropyl |
| benzyl | NHC(=O)NH | CH2CH2C(=O)NH2 | benzyl | O-t-butyl |
| benzyl | NHC(=O)NH | cyclobutyl | benzyl | NH-t-butyl |
| benzyl | NHC(=O)NH | cyclobutyl | benzyl | O-isopropyl |
| benzyl | NHC(=O)NH | cyclobutylmethyl | 4-pyridylmethyl | NH-isopropyl |
| benzyl | NHC(=O)NH | cyclopentylmethyl | benzyl | O-cyclopropyl |
| benzyl | NHC(=O)NH | cyclopropyl | benzyl | NH-cyclopropyl |
| benzyl | NHC(=O)NH | cycopropylmethyl | benzyl | O-t-butyl |
| cis-2-decahydronaphthyl methyl | NHC(=O)NH | 2-butyl | benzyl | NH-t-butyl |
| cis-2-decahydronaphthyl methyl | NHC(=O)NH | 2-butyl | benzyl | O-isopropyl |
| 2-hydroxy-3,3-dimethylpropyl | NHC(=O)NH | 2-butyl | benzyl | NH-isopropyl |
| 2-hydroxy-3,3-dimethylpropyl | NHC(=O)NH | 2-butyl | benzyl | O-cyclopropyl |
| 2-hydroxyindanyl methyl | NHC(=O)NH | 2-butyl | 2-pyridylmethyl | NH-cyclopropyl |
| benzyl | OC(=O)NH | 1-methoxy-2-propyl | benzyl | NH-t-butyl |
| benzyl | OC(=O)NH | 2'-hydroxycyclopentyl methyl | benzyl | O-t-butyl |
| benzyl | OC(=O)NH | 2,2,2-trichloroethyl | 3-pyridylmethyl | NH-t-butyl |
| benzyl | OC(=O)NH | 2,2,2-trifluoroethyl | benzyl | I-isopropyl |
| benzyl | OC(=O)NH | 2-butyl | benzyl | NH-isopropyl |
| benzyl | OC(=O)NH | 2-propyl | benzyl | O-cyclopropyl |
| benzyl | OC(=O)NH | 2-propyl | benzyl | NH-cyclopropyl |
| 2-benzimidazolylmethyl | OC(=O)NH | 2-butyl | benzyl | O-t-butyl |
| 2-naphthylmethyl | OC(=O)NH | 2-butyl | 4-pyridylmethyl | NH-t-butyl |
| 2-pyridylmethyl | OC(=O)NH | 2-butyl | benzyl | O-isopropyl |
| CH3SO2CH2CH2 | OC(=O)NH | 2-butyl | benzyl | NH-isopropyl |
| cyclopentylethyl | OC(=O)NH | 2-butyl | benzyl | O-cyclopropyl |
| F2HCOC6H4CH2 | OC(=O)NH | 2-butyl | benzyl | NH-cyclopropyl |
| 2,4-difluorophenyl | SO2NH | 2-butyl | benzyl | O-t-butyl |
| 4'-methylphenyl | SO2NH | 2-butyl | benzyl | NH-t-butyl |
| benzyl | SO2NH | 2-(methylamino)ethyl | benzyl | O-isopropyl |
| benzyl | SO2NH | 2-furanylmethyl | 2-pyridylmethyl | NH-isopropyl |
| benzyl | SO2NH | 2-propyl | benzyl | O-cyclopropyl |
| benzyl | SO2NH | cyclobutyl | benzyl | NH-cyclopropyl |
| benzyl | SO2NH | cyclopropyl | benzyl | O-t-butyl |
| 4'-methylphenyl | SO2NHC(=O)NH | 2-(dimethylamino)ethyl | benzyl | NH-t-butyl |
| 4'-methylphenyl | SO2NHC(=O)NH | 2-butyl | benzyl | O-isopropyl |
| 4'-methylphenyl | SO2NHC(=O)NH | 2-butyl | benzyl | NH-isopropyl |
| 4'-methylphenyl | SO2NHC(=O)NH | benzyl | benzyl | O-cyclopropyl |
| 4'-methylphenyl | SO2NHC(=O)NH | CH2CH2OH | 3-pyridylmethyl | NH-cyclopropyl |
| 4'-methylphenyl | SO2NHC(=O)NH | cyclobutyl | benzyl | O-t-butyl |
| phenyl | SO2NHC(=O)NH | 2-butyl | 4-pyridylmethyl | NH-t-butyl |
| phenyl | SO2NHC(=O)NH | cyclopropyl | benzyl | O-isopropyl |
| trifluoromethyl | SO2NHC(=O)NH | 2-butyl | benzyl | NH-isopropyl |
| trifluoromethyl | SO2NHC(=O)NH | 2-butyl | benzyl | O-cyclopropyl |
| trifluoromethyl | SO2NHC(=O)NH | cyclobutyl | benzyl | NH-cyclopropyl |
| trifluoromethyl | SO2NHC(=O)NH | cyclopropyl | benzyl | O-t-butyl |

TABLE VII

[Structure with R¹, R², R³, R⁴, R⁵, R¹⁸, W, X substituents; R¹⁸ = H or CH₃]

| R1 | W | X | R2 | R3 | R4 | R5 |
|---|---|---|---|---|---|---|
| benzyl | C(=O)NH | C(=O)NH | benzyl | 2-butyl | benzyl | O-t-butyl |
| benzyl | C(=O)NH | C(=O)O | benzyl | 2-propyl | benzyl | NH-t-butyl |
| benzyl | C(=O)NH | CH2C(=O)CH2 | 4-chlorophenyl | cyclopropyl | benzyl | O-isopropyl |
| benzyl | C(=O)NH | C(=O)CH2 | benzyl | ethyl | benzyl | NH-isopropyl |
| benzyl | C(=O)NH | SO2NH | benzyl | cyclobutyl | benzyl | O-cyclopropyl |
| benzyl | C(=O)NH | CH2NCH3 | 2-(dimethylamino-ethyl) | 2-butyl | benzyl | NH-cyclopropyl |
| benzyl | C(=O)NH | CH2NH | benzyl | 2-butyl | benzyl | O-t-butyl |
| benzyl | C(=O)NH | CH2CH2 | naphthyl | 2-butyl | 4-fluorophenyl | NH-t-butyl |
| benzyl | C(=O)NH | CH=CH | benzyl | 2-butyl | benzyl | O-isopropyl |
| benzyl | C(=O)NH | CH(OH)CH(OH) | 2-acetamido | 2-butyl | naphthyl | NH-isopropyl |
| 3-trifluoromethyl benzyl | C(=O)NH | CH(OH)CH2 | benzyl | 2-butyl | benzyl | O-cyclopropyl |
| benzyl | C(=O)NH | CH2CH(OH) | benzyl | 2-butyl | 4-methoxyphenyl | NH-cyclopropyl |
| benzyl | C(=O)NH | CH(OH) | 4-methanesulfonyl | 2-butyl | benzyl | O-t-butyl |
| benzyl | C(=O)NH | SO2NH | benzyl | 2-butyl | 2,4-dichlorophenyl | NH-t-butyl |
| benzyl | NHC(=O)NH | C(=O)NH | benzyl | 2-butyl | benzyl | O-isopropyl |
| 2-pyridylmethyl | NHC(=O)NH | C(=O)NH | benzyl | 2-butyl | benzyl | NH-isopropyl |
| 2,4-dimethoxybenzyl | NHC(=O)NH | C(=O)NH | benzyl | 2-butyl | benzyl | O-cyclopropyl |
| benzyl | NHC(=O)NH | C(=O)NH | 3-(methylamino)propyl | 2-butyl | benzyl | NH-cyclopropyl |
| naphthyl | NHC(=O)NH | C(=O)NH | benzyl | cyclopropyl | benzyl | O-t-butyl |
| benzyl | NHC(=O)NH | C(=O)NH | 2-imidazolyl-methyl | cyclopropyl | 4-chlorobenyl | NH-t-butyl |
| benzyl | NHC(=O)NH | C(=O)NH | benzyl | 2-butyl | 4-pyridyl | O-isopropyl |
| benzyl | NHC(=O)NH | C(=O)NH | 2-acetamido | 2-butyl | benzyl | NH-isopropyl |
| benzyl | NHC(=O)NH | C(=O)NH | 2-(dimethylamino ethyl) | 2-propyl | benzyl | O-cyclopropyl |
| benzyl | NHC(=O)NH | C(=O)NH | benzyl | 2-butyl | benzyl | NH-cyclopropyl |
| benzyl | NHC(=O)NH | SO2NH | benzyl | 2-butyl | benzyl | O-t-butyl |
| benzyl | NHC(=O)NH | SO2NH | 3-(methylamino)propyl | n-propyl | benzyl | NH-t-butyl |
| benzyl | NHC(=O)NH | SO2NH | isobutyl | 2-propyl | benzyl | O-isopropyl |
| naphthyl | NHC(=O)NH | SO2NH | benzyl | 2-butyl | benzyl | NH-isopropyl |
| benzyl | NHC(=O)NH | SO2NH | 3-indolylmethyl | 2-butyl | benzyl | O-cyclopropyl |
| benzyl | OC(=O)NH | C(=O)NH | benzyl | 2-butyl | benzyl | NH-cyclopropyl |
| benzyl | OC(=O)NH | C(=O)O | benzyl | 2-propyl | benzyl | NH-cyclopropyl |
| benzyl | OC(=O)NH | CH2C(=O)CH2 | 4-chlorophenyl | cyclopropyl | benzyl | O-t-butyl |
| adamantyl | OC(=O)NH | C(=O)CH2 | benzyl | ethyl | benzyl | NH-t-butyl |
| benzyl | OC(=O)NH | SO2NH | benzyl | cyclobutyl | benzyl | O-isopropyl |
| benzyl | OC(=O)NH | CH2NCH3 | 2-(dimethylamino-ethyl) | 2-butyl | benzyl | NH-isopropyl |
| cyclohexylmethyl | OC(=O)NH | CH2NH | benzyl | 2-butyl | benzyl | O-cyclopropyl |
| benzyl | OC(=O)NH | CH2CH2 | naphthyl | 2-butyl | 4-fluorophenyl | NH-cyclopropyl |

SCHEME I

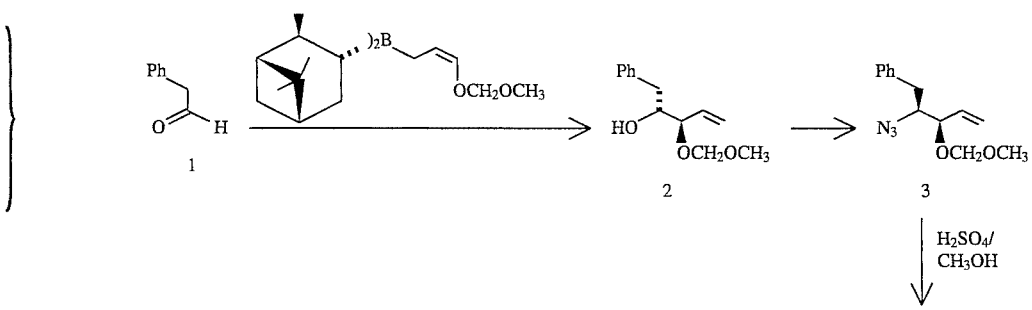

5,491,149
-continued
SCHEME I
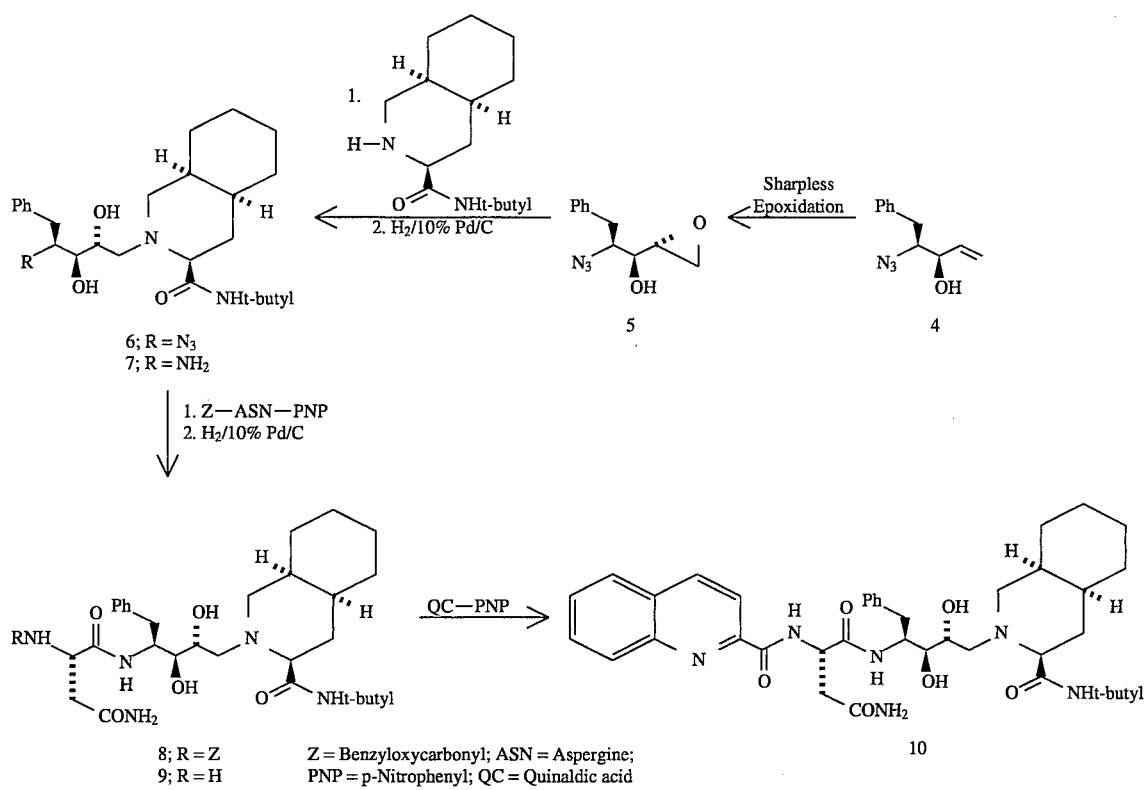
8; R = Z  
9; R = H
Z = Benzyloxycarbonyl; ASN = Aspergine;  
PNP = p-Nitrophenyl; QC = Quinaldic acid
SCHEME II
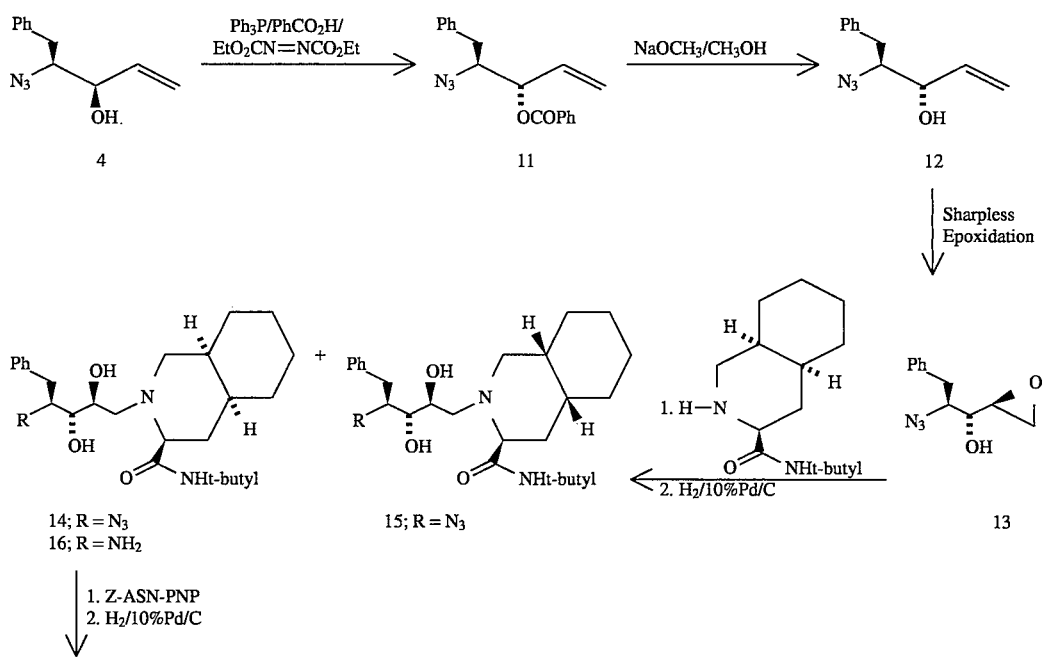

-continued
SCHEME II
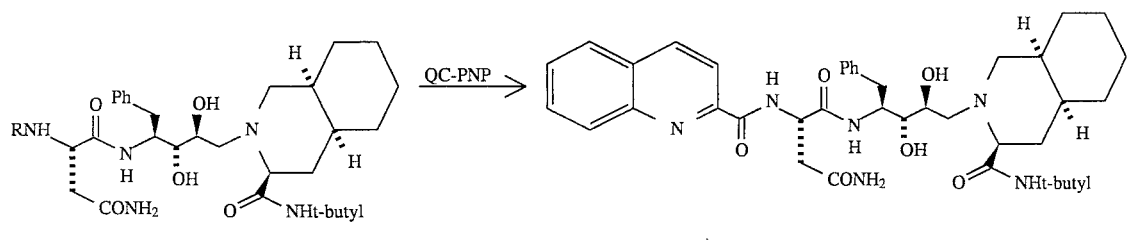
17; R = Z
18; R = H
Z = Benzyloxycarbonyl; ASN = Aspergine;
PNP = p-Nitrophenyl; QC = Quinaldic acid
19
SCHEME III
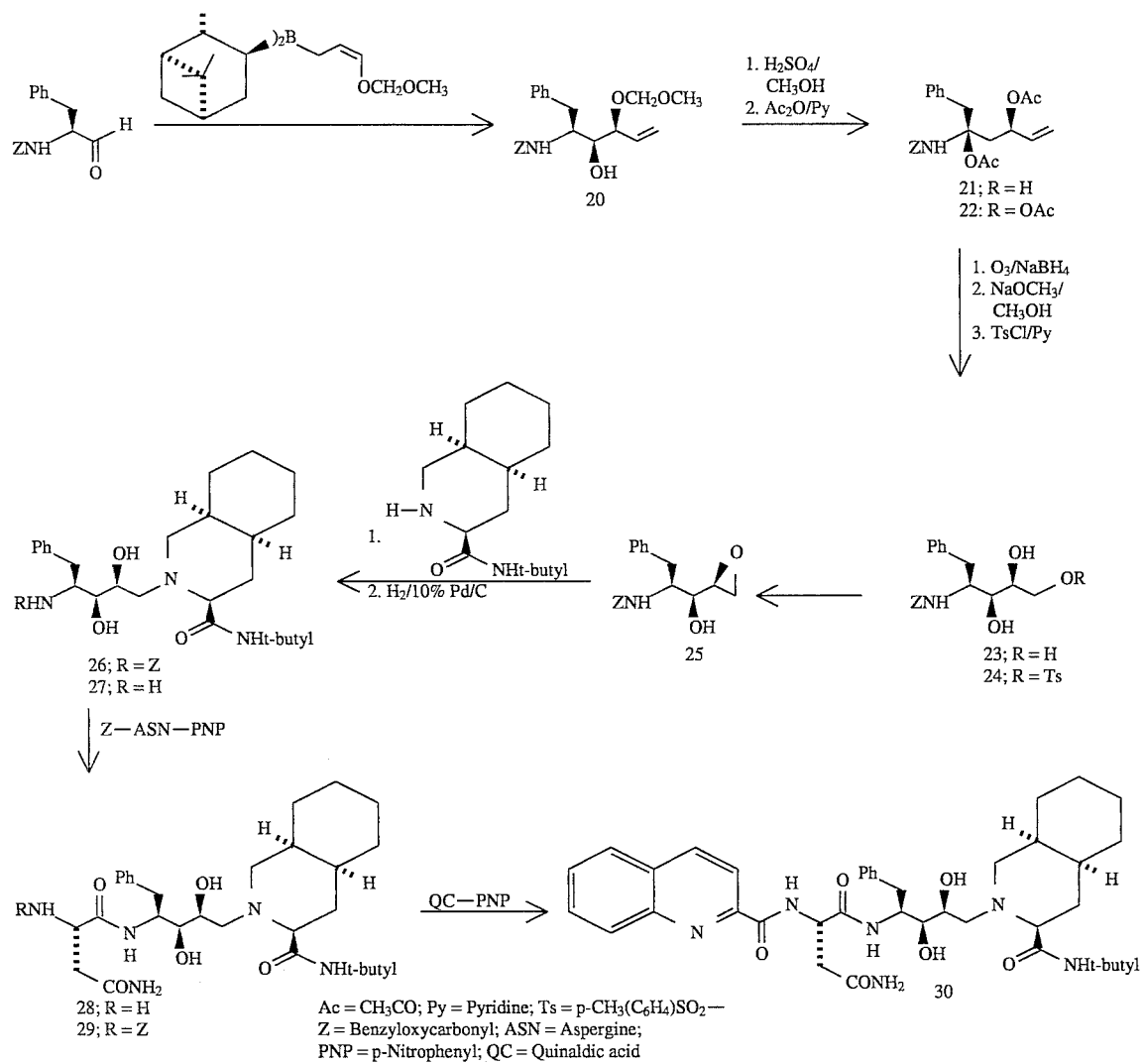
Ac = CH₃CO; Py = Pyridine; Ts = p-CH₃(C₆H₄)SO₂—
Z = Benzyloxycarbonyl; ASN = Aspergine;
PNP = p-Nitrophenyl; QC = Quinaldic acid

SCHEME IV

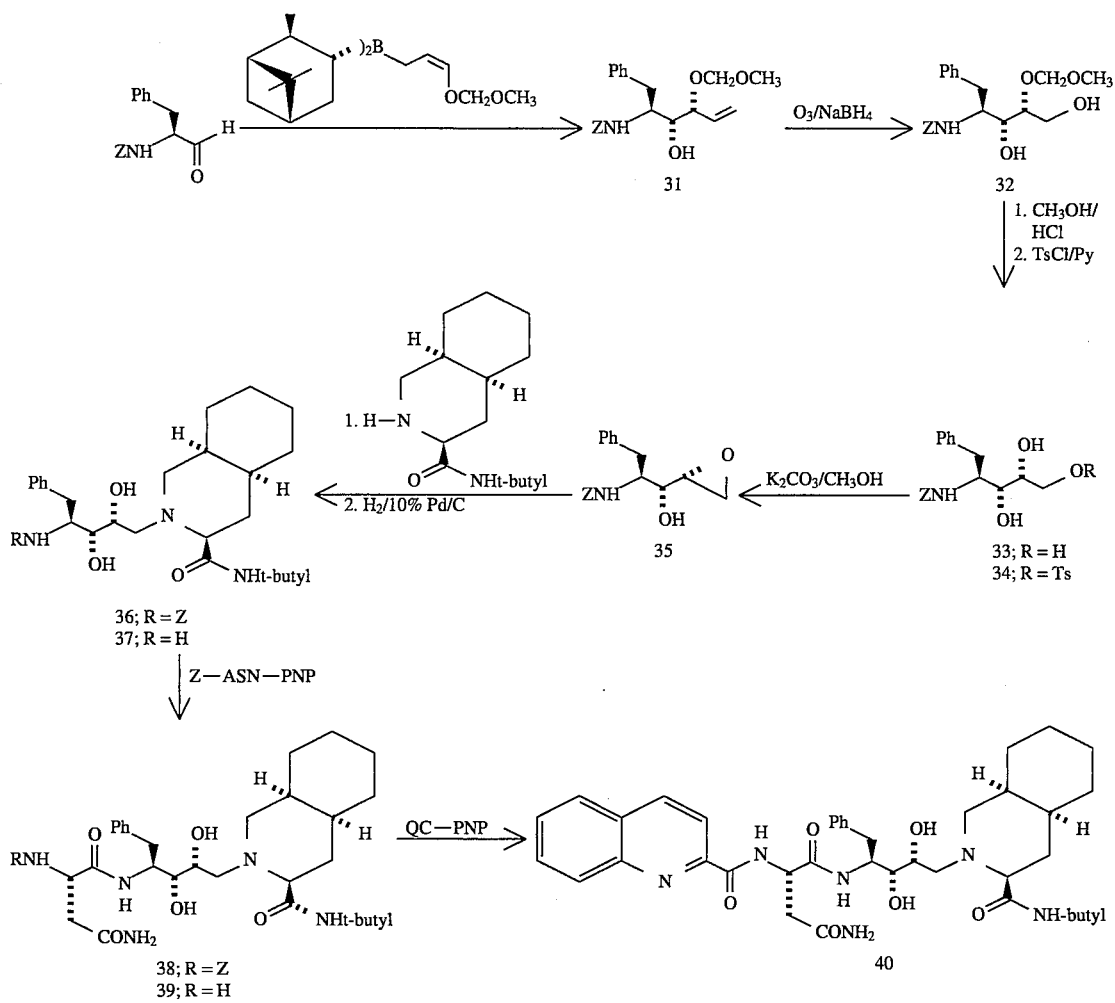

Ac = CH₃CO; Py = Pyridine; Ts = p-CH₃(C₆H₄)SO₂—
Z = Benzyloxycarbonyl; ASN = Aspergine;
PNP = p-Nitrophenyl; QC = Quinaldic acid

What is claimed is:

1. A compound of the formula (I):

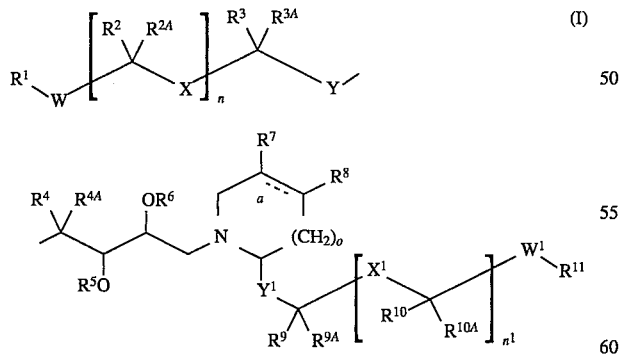

or a pharmaceutically acceptable salt, chiral, diastereomeric or racemic form thereof wherein:

$R^1, R^2, R^3, R^4, R^7, R^8, R^9, R^{10}$, and $R^{11}$ are independently selected from the following groups:
hydrogen;
$C_1$–$C_8$ alkyl substituted with 0–3 $R^{12}$;
$C_2$–$C_8$ alkenyl substituted with 0–3 $R^{12}$;
$C_3$–$C_8$ alkynyl substituted with 0–3 $R^{12}$;
$C_3$–$C_8$ cycloalkyl substituted with 0–3 $R^{12}$;
$C_6$–$C_{10}$ bicycloalkyl substituted with 0–3 $R^{12}$;
aryl substituted with 0–3 $R^{13}$;
a $C_6$–$C_{14}$ carbocyclic ring substituted with 0–3 $R^{13}$;
a heterocyclic ring substituted with 0–2 $R^{13}$, composed of 5 to 10 atoms including from 1 to 3 nitrogen, oxygen or sulfur atoms, with the remaining atoms being carbon;
additionally, $R^7$ and $R^8$ may join together to form a saturated or unsaturated $C_5$–$C_{14}$ carbocyclic ring substituted with 0–3 $R^{12}$, or a heterocyclic ring substituted with 0–2 $R^{13}$, said heterocyclic ring being composed of 5 to 10 atoms including 1 to 3 nitrogen, oxygen, or sulfur atom with the remaining atoms being carbon;

$R^{2A}$, $R^{3A}$, $R^{4A}$, $R^{9A}$, and $R^{10A}$ are independently selected from the following groups:
hydrogen;
$C_1$–$C_4$ alkyl substituted with halogen or $C_1$–$C_2$ alkoxy;
benzyl substituted with halogen or $C_1$–$C_2$ alkoxy;

$R^5$ and $R^6$ are independently selected from the following groups:
hydrogen;
$C_1$–$C_6$ alkoxycarbonyl;
$C_1$–$C_6$ alkylcarbonyl;
benzoyl;
phenoxycarbonyl; or
phenylaminocarbonyl; wherein said alkyl groups are substituted with 0–3 $R^{12}$, and said aryl groups are substituted with 0–3 $R^{13}$; or a hydrolyzable group that, when administered to a mammalian subject, is metabolically cleaved to form the diol in which $R^5$ and $R^6$ are hydrogen;

$R^{12}$ is selected from one or more of the following:
keto, halogen, cyano, —$NR^{14}R^{15}$, —$CO_2R^{14}$, —$OC(=O)R^{15}$, —$OR^{14}$, $C_2$–$C_6$ alkoxyalkyl, —$S(O)_mR^{14}$, —$NHC(=NH)NHR^{14}$, —$C(=NH)NHR^{14}$, —$C(=O)NR^{14}R^{15}$, —$NR^{15}C(=O)R^{15}$, —$NR^{15}C(=O)OR^{15}$, —$OC(=O)NR^{14}R^{15}$, —$NR^{14}C(=O)NR^{14}R^{15}$, —$NR^{15}SO_2NR^{14}R^{15}$, —$NR^{15}SO_2R^{14}$, —$SO_2NR^{14}R^{15}$, $C_1$–$C_4$ alkyl, $C_2$–$C_4$ alkenyl, $C_3$–$C_6$ cycloalkyl, $C_3$–$C_6$ cycloalkylmethyl;
a $C_5$–$C_{14}$ carbocyclic ring substituted with 0–3 $R^{13}$;
aryl substituted with 0–3 $R^{13}$;
or a heterocyclic ring substituted with 0–2 $R^{13}$, said heterocyclic ring being composed of 5 to 10 atoms including 1 to 3 nitrogen, oxygen, or sulfur atom with the remaining atoms being carbon;

$R^{13}$, when a substituent on carbon, is selected from one to 3 of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, alkoxy, —$NR^{14}R^{15}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{14}$, —$SO_2NR^{14}R^{15}$, —$NHSO_2R^{15}$;
or $R^{13}$ may be a 3- or 4-carbon chain attached to adjacent carbons on the ring to form a fused 5- or 6-membered ring, said 5- or 6-membered ring being substituted on the aliphatic carbons with from 1 to 3 halogen, $C_1$–$C_4$ alkyl, $C_1$–$C_4$ alkoxy, hydroxy, or $NR^{14}R^{15}$; or, when $R^{13}$ is attached to a saturated carbon atom it may be carbonyl or thiocarbonyl;

and $R^{13}$, when a substituent on nitrogen, is independently selected from the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$NR^{14}R^{15}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl;

$R^{14}$ is H, phenyl, benzyl or $C_1$–$C_6$ alkyl;
$R^{15}$ is H or $C_1$–$C_4$ alkyl;
or $R^{14}$ and $R^{15}$ can join to form $(CH_2)_4$, $(CH_2)_5$, $(CH_2CH_2N(R^{16})CH_2CH_2)$, or $(CH_2CH_2OCH_2CH_2)$;
$R^{16}$ is H or $CH_3$;
a is a double or single bond;
m is 0, 1 or 2;
n and $n^1$ are independently 0 or 1;
o is 0, 1, 2 or 3;
W and $W^1$ are independently selected from the following:
—$NR^{16}C(=Q)NR^{16}$—; —$C(=Q)NR^{16}$—; —$C(=Q)O$—; —$NR^{16}C(=Q)O$—; —$OC(=Q)NR^{16}$—; —$NR^{16}C(=Q)$—; —$C(=Q)$—; —$C(=Q)CH_2$—; —$NR^{16}SO_2NR^{16}$— —$NR^{16}SO_2$—; —$SO_2NR^{16}$— —$SO_2$—; —$QCH_2$—; —$Q$—; —$(CH_2)_pNR^{16}$—; —$CH_2CH_2$—; —$CH=CH$—; —$CH(OH)CH(OH)$—; —$CH(OH)CH_2$—; —$CH_2CH(OH)$—; —$CH(OH)$—; —$NH$—$NH$—; —$C(=O)NH$—$NH$—; —$C(Cl)=N$—; —$C(—OR^{16})=N$—; —$C(—NR^{16}R^{17})=N$—; —$OP(=O)(Q^1R^{16})O$—; —$P(=O)(Q^1R^{16})O$—; —$SO_2NHC(=O)NH$—; or a direct bond;

X and $X^1$ are independently selected from the following:
—$C(=Q)NR^{16}$—; —$C(=Q)O$—; —$C(=Q)$—; —$CH_2C(=Q)$—; —$CH_2C(=Q)CH_2$—; —$C(=Q)CH_2$—; —$SO_2NR^{16}$—; —$SO_2$—; —$CH_2QCH_2$—; —$CH_2Q$—; —$CH_2NR^{16}$—; —$CH_2CH_2$—; —$CH=CH$—; —$CH(OH)CH(OH)$—; —$CH(OH)CH_2$—; —$CH_2CH(OH)$—; —$CH(OH)$—; —$C(=Q)NH$—$NH$—; —$C(—OR^{16})=N$—; —$C(—NR^{16}R^{17})=N$—; —$C(L)=N$—;

Y and $Y^1$ are independently selected from the following:
—$C(=Q)NR^{16}$—; —$(CH_2)_pC(=Q)NR^{16}$—; —$SO_2NR^{16}$—; —$CH_2NR^{16}$—; —$C(L)=N$—; —$C(—OR^{16})=N$—; —$C(—NR^{16}R^{17})=N$—; —$NR12C(=O)NR^{16}$—; —$(CH_2)_pNR12C(=O)NR^{16}$—; —$OC(=O)NR^{16}$—; —$(CH_2)_pOC(=O)NR^{16}$—;

$R^{17}$ is H, benzyl or $C_1$–$C_4$ alkyl;
$R^{18}$ is H or $C_1$–$C_4$ alkyl;
L is Cl or Br;
p is 1 or 2;
Q is selected from oxygen or sulfur; and
$Q^1$ is selected from oxygen, sulfur, $NR^{14}$ or a direct bond.

2. A compound of claim 1 of the formula:

wherein:
$R^1$ and $R^{11}$ are independently selected from the following:
hydrogen;
$C_1$–$C_6$ alkyl substituted with 0–2 $R^{12}$;
$C_2$–$C_4$ alkenyl substituted with 0–2 $R^{12}$;
$C_3$–$C_6$ cycloalkyl substituted with 0–2 $R^{12}$;
$C_6$–$C_{10}$ bicycloalkyl substituted with 0–2 $R^{12}$;
aryl substituted with 0–3 $R^{13}$;
a $C_6$–$C_{14}$ carbocyclic ring substituted with 0–3 $R^{13}$;
a heterocyclic ring substituted with 0–2 $R^{13}$, composed of 5 to 10 atoms including 1 to 3 nitrogen, oxygen or sulfur atom, with the remaining atoms being carbon;

$R^3$ and $R^9$ are independently selected from the following groups:
hydrogen;
$C_1$–$C_5$ alkyl substituted with 0–2 $R^{12}$;
$C_2$–$C_4$ alkenyl substituted with 0–2 $R^{12}$;
$C_3$–$C_6$ cycloalkyl substituted with 0–2 $R^{12}$;
with the proviso that the total number of non-hydrogen atoms comprising $R^3$ is less than or equal to 6, and the total number of non-hydrogen atoms comprising $R^9$ is less than or equal to 6;

83

$R^4$ is selected from the following groups:
hydrogen;
$C_1$–$C_5$ alkyl substituted with 0–3 $R^{12}$;
$C_2$–$C_4$ alkenyl substituted with 0–2 $R^{12}$;
$C_3$–$C_6$ cycloalkyl substituted with 0–2 $R^{12}$;
$C_6$–$C_{10}$ bicycloalkyl substituted with 0–3 $R^{12}$;
a $C_6$–$C_{14}$ carbocyclic ring substituted with 0–3 $R^{13}$;
a heterocyclic ring substituted with 0–2 $R^{13}$, composed of 5 to 10 atoms including from 1 to 3 nitrogen, oxygen or sulfur atoms, with the remaining atoms being carbon;

$R^{3A}$ and $R^{4A}$ are independently selected from the following groups:
hydrogen;
$C_1$–$C_2$ alkyl;

$R^5$ and $R^6$ are independently selected from the following groups:
hydrogen; or a hydrolyzable group that, when administered to a mammalian subject, is metabolically cleaved to form the diol in which $R^5$ and $R^6$ are hydrogen;

$R^7$ and $R^8$ may join together to form a saturated or unsaturated $C_5$–$C_{14}$ carbocyclic ring; or a heterocycle, or are independently selected from the following groups:
hydrogen;
$C_1$–$C_2$ alkyl substituted with halogen or $C_1$–$C_2$ alkoxy;

$R^{12}$ is selected from one or more of the following: keto, halogen, cyano, —$NR^{14}R^{15}$, —$CO_2R^{14}$, —$OC(=O)R^{15}$, —$OR^{14}$, $C_2$–$C_6$ alkoxyalkyl, —$S(O)_mR^{14}$, —$NHC(=NH)NHR^{14}$, —$C(=NH)NHR^{14}$, —$C(=O)NR^{14}R^{15}$, —$NR^{15}C(=O)R^{15}$, —$NR^{15}C(=O)OR^{15}$, —$OC(=O)NR^{14}R^{15}$, $NR^{14}C(=O)NR^{14}R^{15}$, —$NR^{15}SO_2NR^{14}R^{15}$, —$NR^{15}SO_2R^{14}$, —$SO_2NR^{14}R^{15}$, $C_1$–$C_4$ alkyl, $C_2$–$C_4$ alkenyl, $C_3$–$C_6$ cycloalkyl, $C_3$–$C_6$ cycloalkylmethyl;
a $C_5$–$C_{14}$ carbocyclic ring substituted with 0–3 $R^{13}$;
aryl substituted with 0–3 $R^{13}$;
or a heterocyclic ring substituted with 0–2 $R^{13}$, composed of 5 to 10 atoms including from 1 to 3 nitrogen, oxygen or sulfur atoms, with the remaining atoms being carbon;

$R^{13}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, alkoxy, —$NR^{14}R^{15}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{14}$, —$SO_2NR^{14}R^{15}$, —$NHSO_2R^{15}$;
or $R^{13}$ may be a 3- or 4-carbon chain attached to adjacent carbons on the ring to form a fused 5- or 6-membered ring, said 5- or 6-membered ring being substituted on the aliphatic carbons with from 1 to 3 halogen, $C_1$–$C_4$ alkyl, $C_1$–$C_4$ alkoxy, hydroxy, or $NR^{14}R^{15}$; or, when $R^{13}$ is attached to a saturated carbon atom it may be carbonyl or thiocarbonyl;

and $R^{13}$, when a substituent on nitrogen, is independently selected from the following:
benzyl, hydroxy, $C_1$–$C_4$ alkoxy, $C_1$–$C_5$ hydroxyalkyl, $C_1$–$C_4$ alkyl, $C_3$–$C_6$ cycloalkyl, $C_3$–$C_6$ cycloalkylmethyl, $C_1$–$C_4$ alkoxycarbonyl, $C_1$–$C_4$ alkylcarbonyloxy, $C_1$–$C_4$ alkylcarbonyl;

84

$R^{14}$ is H, benzyl or $C_1$–$C_4$ alkyl;
$R^{15}$ is H or $C_1$–$C_4$ alkyl;
or $R^{13}$ and $R^{14}$ can join to form $(CH_2)_4$, $(CH_2)_5$, $(CH_2CH_2N(R^{16})CH_2CH_2)$, or $(CH_2CH_2OCH_2CH_2)$;
$R^{16}$ is H or $CH_3$;
a is a double or single bond;
m is 0, 1 or 2;
o is 0, or 2;

W and $W^1$ are independently selected from the following:
—$NR^{16}C(=Q)NR^{16}$—; —$C(=Q)NR^{16}$—;
—$OC(=Q)NR^{16}$—; —$NR^{16}SO_2NR^{16}$—;
—$SO_2NR^{16}$—; —$(CH_2)_pNR^{16}$—;
—$P(=O)(Q^1R^{16})O$—; —$SO_2NHC(=O)NH$—; or
a direct bond;

Y and $Y^1$ are independently selected from the following:
—$C(=Q)NR^{16}$—; —$NR12C(=O)NR^{16}$—; and
—$OC(=O)NR^{16}$—;

$R^{17}$ is H or $C_1$–$C_2$ alkyl;
Q is selected from oxygen or sulfur; and
$Q^1$ is selected from oxygen, sulfur, $NR^{14}$ or a bond.

3. A compound of claim 1 of the formula:

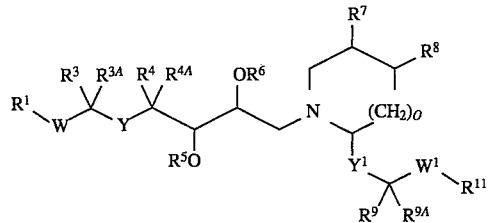

wherein:
$R^1$ and $R^{11}$ are independently selected from the following:
hydrogen;
$C_1$–$C_6$ alkyl substituted with 0–1 $R^{18}$;
$C_2$–$C_4$ alkenyl substituted with 0–1 $R^{18}$;
aryl substituted with 0–1 $R^{20}$;
a heterocyclic ring, substituted with 0–1 $R^{20}$, selected from pyridyl, pyrimidinyl, furanyl, thienyl, pyrrolyl, pyrazolyl,
imidazolyl, tetrazolyl, benzofuranyl, benzothiophenyl, indolyl,
indolenyl, quinolinyl, isoquinolinyl, benzimidazolyl, piperidinyl,
pyrrolidinyl, tetrahydrofuranyl, tetrahydroquinolinyl, tetrahydroisoquinolinyl, or decahydroisoquinolinyl;
wherein $R^{18}$ is selected from the following group:
keto, halogen, cyano, —$NR^{14}R^{15}$, —$CO_2R^{14}$, —$OC(=O)R^{15}$, —$OR^{14}$, $C_2$–$C_6$ alkoxyalkyl, —$S(O)_mR^{14}$, —$NHC(=NH)NHR^{14}$, —$C(=O)NR^{14}R^{15}$, —$NR^{15}C(=O)R^{15}$, —$NR^{15}C(=O)OR^{15}$, —$OC(=O)NR^{14}R^{15}$, $NR^{14}C(=O)NR^{14}R^{15}$, —$NR^{15}SO_2NR^{14}R^{15}$, —$NR^{15}SO_2R^{14}$, —$SO_2NR^{14}R^{15}$, $C_1$–$C_4$ alkyl, $C_2$–$C_4$ alkenyl, or $C_3$–$C_6$ cycloalkyl;
a $C_5$–$C_{14}$ carbocyclic ring substituted with 0–3 $R^{20}$;
aryl substituted with 0–2 $R^{20}$;
or a heterocyclic ring substituted with 0–2 $R^{20}$, selected from selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, pyrrolidinyl, tetrahydrofuranyl, tetrahydroquinolinyl, tetrahydroisoquinolinyl, or decahydroisoquinolinyl;

wherein $R^{20}$, when a substituent on carbon, is selected from the following:
halogen, hydroxy, nitro, cyano, methyl, methoxy, —$NR^{13}R^{14}$, $C_1$–$C_4$ haloalkyl, $C_1$–$C_2$ alkoxycarbonyl, $C_1$–$C_2$ alkylcarbonyloxy, $C_1$–$C_2$ alkylcarbonylamino, —$SO_2NR^{13}R^{14}$, or —$NHSO_2R^{14}$;
and $R^{20}$, when a substituent on nitrogen, is $C_1$–$C_4$ alkyl;

$R^3$ and $R^9$ are independently selected from the following groups:
hydrogen;
$C_1$–$C_5$ alkyl substituted with 0–3 halogen or 0–1 $R^{23}$;
$C_2$–$C_4$ alkenyl substituted with 0–3 halogen or 0–1 $R^{23}$;
$C_3$–$C_6$ cycloalkyl substituted with 0–3 halogen or 0–1 $R^{23}$;
wherein $R^{23}$ is selected from the following groups:
keto, amino, methylamino, dimethylamino, —C(=O)$NH_2$, C(=O)$NMe_2$, C(=O)NHMe, or $C_3$–$C_5$ cycloalkyl;
with the proviso that the total number of non-hydrogen atoms comprising $R^3$ is less than or equal to 6, and the total number of non-hydrogen atoms comprising $R^9$ is less than or equal to 6;

$R^4$ is selected from the following groups:
hydrogen;
$C_1$–$C_4$ alkyl substituted with 0–3 halogen or 0–3 $R^{26}$;
aryl substituted with 0–1 $R^{26}$;
a heterocyclic ring selected from pyridyl, thienyl, indolyl, pyrolyl, piperazyl, N-methylpiperazyl, or imidazolyl, substituted with 0–2 $R^{27}$;
wherein $R^{26}$ is selected from one or more of the following:
keto, halogen, cyano, —$NR^{14}R^{15}$, —$CO_2R^{14}$, —OC(=O)$R^{15}$, —$OR^{14}$, $C_2$–$C_6$ alkoxyalkyl, —$S(O)_mR^{14}$, $C_3$–$C_6$ cycloalkyl, $C_3$–$C_6$ cycloalkylmethyl;
aryl substituted with 0–3 $R^{13}$;
or a heterocyclic ring selected from pyridyl, thienyl, pyrolyl, indolyl, piperazyl, N-methylpiperazyl, or imidazolyl, substituted with 0–2 $R^{27}$;
wherein $R^{27}$, when a substituent on carbon, is independently selected from the following:
phenyl, benzyl, benzyloxy, halogen, hydroxy, nitro, $C_1$–$C_4$ alkyl, $C_1$–$C_4$ alkoxy, amino, methylamino, dimethylamino, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino;
and $R^{27}$, when a substituent on nitrogen, is $C_1$–$C_4$ alkyl;

$R^{3A}$ and $R^{4A}$ are hydrogen;

$R^5$ and $R^6$ are independently selected from the following groups:
hydrogen, or a hydrolyzable group that, when administered to a mammalian subject, is metabolically cleaved to form the diol in which $R^5$ and $R^6$ are hydrogen;

$R^7$ and $R^8$ join together to form a saturated or unsaturated $C_6$–$C_{14}$ carbocyclic ring;

$R^{14}$ and $R^{15}$ are independently selected from H or $C_1$–$C_2$ alkyl;

m is 0, 1 or 2;

n and $n^1$ are 0;

o is 1;

W and W1 are independently selected from the following:
—$NR^{16}C(=Q)NR^{16}$—; —C(=O)$NR^{16}$—; —OC(=O)$NR^{16}$—; —$(CH_2)_pNR^{16}$—; or a direct bond;

Y and $Y^1$ are independently selected from the following:
—C(=O)$NR^{16}$—; —NR12C(=O)$NR^{16}$—; or —OC(=O)$NR^{16}$—;

$R^{16}$ is H or methyl; and

Q is selected from oxygen or sulfur.

4. A compound of claim 1 of the formula:

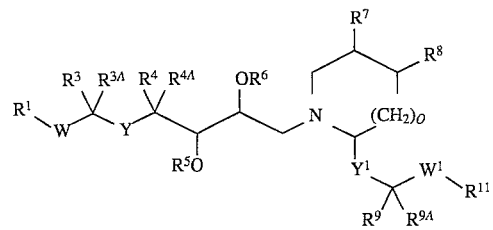

wherein:
$R^1$ is selected from the following:
hydrogen;
$C_1$–$C_3$ alkyl substituted with 0–1 $R^{18}$;
wherein $R^{18}$ is chosen from the following group:
keto, halogen, cyano, or $C_3$–$C_6$ cycloalkyl;
aryl substituted with 0–2 $R^{20}$;
or a heterocyclic ring substituted with 0–2 $R^{20}$, selected from pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, pyrrolidinyl, tetrahydroquinolinyl, or tetrahydroisoquinolinyl;
wherein $R^{20}$, when a substituent on carbon, is halogen, methyl, or methoxy;
and $R^{20}$, when a substituent on nitrogen, is methyl;

$R^3$ is selected from the following groups:
hydrogen;
$C_1$–$C_3$ alkyl substituted with 0–3 halogen or C(=O)$NH_2$;
with the proviso that the total number of non-hydrogen atoms comprising $R^3$ is less than or equal to 6;

$R^9$, $R^{9A}$, and $R^{11}$ are independently selected from $C_1$–$C_2$ alkyl or hydrogen $R^4$ is selected from the following groups:
$C_1$–$C_4$ alkyl substituted with 0–3 halogen or 0–1 $R^{26}$;
wherein $R^{26}$ is selected from the following groups:
$C_3$–$C_6$ cycloalkyl; aryl; or a heterocyclic ring selected from pyridyl, thienyl, pyrolyl, or indolyl;

$R^{3A}$ and $R^{4A}$ are hydrogen;

$R^5$ and $R^6$ are hydrogen;

$R^7$ and $R^8$ join together to form a saturated or unsaturated 5 or 6 membered carbocyclic ring;

W is selected from the following:
—$NR^{16}C(=O)NR^{16}$—; —C(=O)$NR^{16}$—; —OC(=O)$NR^{16}$—; or a direct bond;

$W^1$ is a direct bond;

Y and $Y^1$ are —C(=O)$NR^{16}$—; and $R^{16}$ is H or methyl.

5. A compound of claim 1 of the formula:

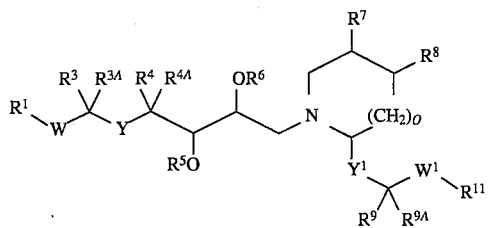

wherein:

R¹ is selected from the following:
hydrogen;
$C_1$–$C_2$ alkyl substituted with 0–1 $R^{18}$;
wherein $R^{18}$ is chosen from the following group:
aryl substituted with 0–2 $R^{20}$;
or a heterocyclic ring substituted with 0–2 $R^{20}$, selected from pyridyl, thienyl, pyrrolyl, pyrazolyl, imidazolyl, tetrazolyl, benzothiophenyl, indolyl, quinolinyl, isoquinolinyl, or benzimidazolyl;
wherein $R^{20}$, when a substituent on carbon, is halogen, methyl, or methoxy;
and $R^{20}$, when a substituent on nitrogen, is methyl;

R³ is selected from the following groups:
$C_1$–$C_3$ alkyl optionally substituted with C(=O)NH₂;
with the proviso that the total number of non-hydrogen atoms comprising R³ is less than or equal to 6;

$R^9$, $R^{9A}$, and $R^{11}$ are independently selected from methyl or hydrogen R⁴ is selected from the following groups:
$C_1$–$C_2$ alkyl substituted with 0–3 halogen or 0–1 $R^{26}$; wherein $R^{26}$ is selected from the following groups:
$C_3$–$C_6$ cycloalkyl; aryl; or a heterocyclic ring selected from pyridyl, thienyl, pyrolyl, or indolyl;

$R^{3A}$ and $R^{4A}$ are hydrogen;

R⁵ and R⁶ are hydrogen;

R⁷ and R⁸ join together to form a saturated or unsaturated 5 or 6 membered carbocyclic ring;

W is selected from the following:
—NHC(=O)NH—;   —C(=O)NH—;   or
—OC(=O)NH—;

W¹ is a direct bond; and

Y and Y¹ are —C(=O)NH—.

6. The compound of claim 1 which is:

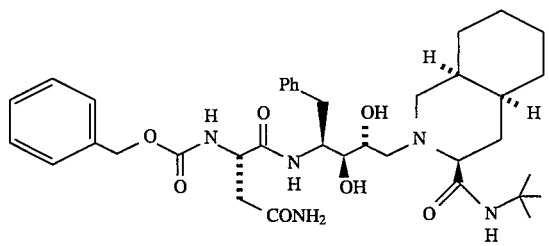

[3S-[2[1R*(R*),2R*,3S*],3a,4ab,8ab]]-(phenylmethyl)[3-amino-1-[[[4-[3-[[(1,1-dimethylethyl)amino] carbonyl]octahydro- 2(1H)-isoquinolinyl]-2,3-dihydroxy- 1(phenylmethyl)butyl]amino]carbonyl] -3-oxopropyl]carbamate.

7. The compound of claim 1 which is:

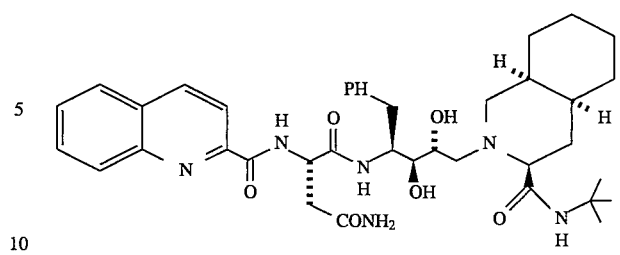

[3S-[2[1R*(R*),2R*,3S*],3a,4ab,8b]]-N1-[4-[3-[[(1,1-dimethylethyl)amino]carbonyl]octahydro-2(1H)-isoquinolinyl] -2,3-dihydroxy-1-(phenylmethyl)butyl]-2-[ (2-quinolinylcarbonyl)amino]butanediamide.

8. The compound of claim 1 which is:

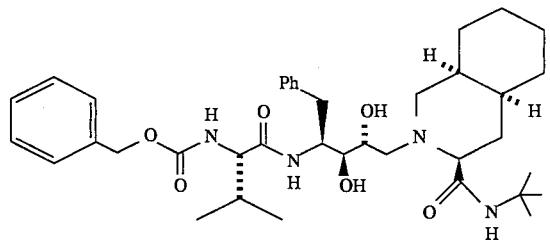

[3-[2[1R*(R*),2R*,3S*],3a,4ab,8ab]]-(phenylmethyl)[ 1-[[ [4-[3-[[(1,1 -dimethylethyl)amino]carbonyl]octahydro-2(1H)-isoquinolinyl- 2,3-dihydroxy-1-(phenylmethyl)butyl] amino]carbonyl]- 2-methylpropyl]carbamate.

9. The compound of claim 1 which is:

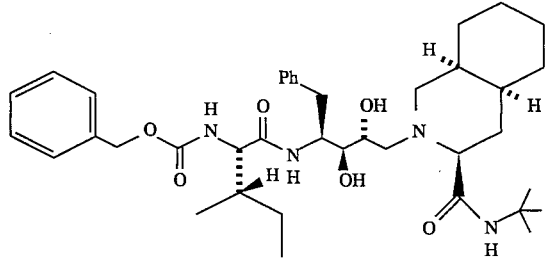

[3S-[2[1R*(R*,R*),2R*,3S*],3a,4ab,8ab]]-(phenylmethyl) [1-[[[4-[3-[[(1,1 -dimethylethyl)amino]carbonyl]octahydro-2(1H)-isoquinolinyl]-2,3-dihydroxy-1-(phenylmethyl)butyl] amino]carbonyl]-2-methylbutyl]carbamate.

10. The compound of claim 1 which is:

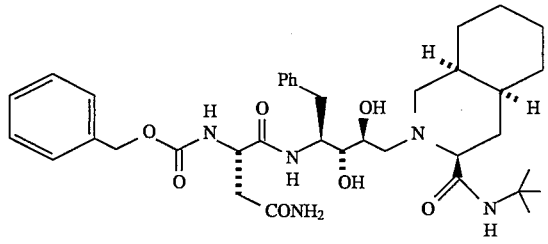

[3S-[2[1R*(R*),2S*,3R*],3a,4ab,8ab]]-(phenylmethyl)[[3-amino-1-[[[4-[3-[[(1,1-dimethylethyl)amino] carbonyl]octahydro- 2(1H)-isoquinolinyl]-2,3-dihydroxy-1-(phenylmethyl)butyl] amino]-carbonyl]-3-oxopropyl]carbamate.

11. The compound of claim 1 which is:

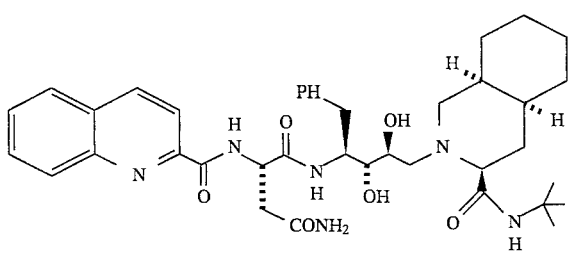

[3S-[2[1R*(R*),2S*,3R*],3a,4ab,8ab]]-N1-[4-[3-[[ (1,1-dimethylethyl)amino]carbonyl]octahydro-2(1H)-isoquinolinyl] -2,3-dihydroxy-1-(phenylmethyl)butyl]-2-[(2-quinolinylcarbonyl)amino]butanediamide.

12. The compound of claim 1 which is:

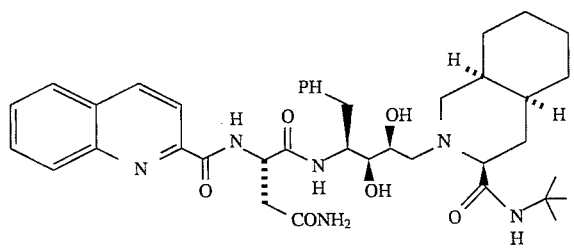

[3S-[2[1R*(R*),2R*,3R*],3a,4ab,8ab]]-N1-[4-[3-[[(1,1-dimethylethyl)amino]carbonyl]octahydro-2 -(1H)-isoquinolinyl] -2,3-dihydroxy-1-(phenylmethyl)butyl]-2-[(2-quinolinylcarbonyl)amino]butanediamide.

13. The compound of claim 1 which is:

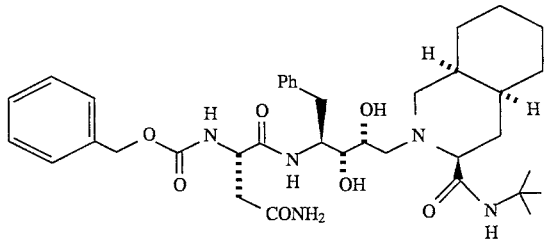

[3S-[2[1R*(R*),2S*,3S*],3a,4ab,8ab]]-(phenylmethyl)[3-amino-1-[[[4-[3-[[(1,1-dimethylethyl)amino] carbonyl]octahydro- 2(1H)-isoquinolinyl-2,3-dihydroxy-1-(phenylmethyl)butyl] amino]-carbonyl]-3-oxopropyl] carbamate.

14. The compound of claim 1 which is:

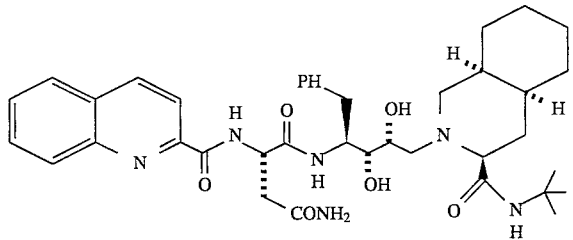

[3S-[2[1R*(R*),2S*,3S*],3a,4ab,8ab]]-N1-[4-[3 -[[(1,1-dimethylethyl)amino]carbonyl]octahydro-2(1H)-isoquinolinyl] -2,3-dihydroxy-1-(phenylmethyl)butyl]-2-[(2-quinolinylcarbonyl)amino] butanediamide.

15. A method for treatment of viral infections which comprises administering to a host in need of such treatment a pharmaceutically effective amount of a compound of claim 1.

16. A method for treatment of viral infections which comprises administering to a host in need of such treatment a pharmaceutically effective amount of a compound of claim 2.

17. A method for treatment of viral infections which comprises administering to a host in need of such treatment a pharmaceutically effective amount of a compound of claim 3.

18. A method for treatment of viral infections which comprises administering to a host in need of such treatment a pharmaceutically effective amount of a compound of claim 4.

19. A method for treatment of viral infections which comprises administering to a host in need of such treatment a pharmaceutically effective amount of a compound of claim 5.

20. A method for treatment of viral infections which comprises administering to a host in need of such treatment a pharmaceutically effective amount of a compound of claim 6.

21. A method for treatment of viral infections which comprises administering to a host in need of such treatment a pharmaceutically effective amount of a compound of claim 7.

22. A method for treatment of viral infections which comprises administering to a host in need of such treatment a pharmaceutically effective amount of a compound of claim 8.

23. A method for treatment of viral infections which comprises administering to a host in need of such treatment a pharmaceutically effective amount of a compound of claim 9.

24. A method for treatment of viral infections which comprises administering to a host in need of such treatment a pharmaceutically effective amount of a compound of claim 10.

25. A method for treatment of viral infections which comprises administering to a host in need of such treatment a pharmaceutically effective amount of a compound of claim 11.

26. A method for treatment of viral infections which comprises administering to a host in need of such treatment a pharmaceutically effective amount of a compound of claim 12.

27. A method for treatment of viral infections which comprises administering to a host in need of such treatment a pharmaceutically effective amount of a compound of claim 13.

28. A method for treatment of viral infections which comprises administering to a host in need of such treatment a pharmaceutically effective amount of a compound of claim 14.

29. A pharmaceutical composition comprising a pharmaceutically acceptable carrier and a pharmaceutically effective antiviral amount of a compound of claim 1.

30. A pharmaceutical composition comprising a pharmaceutically acceptable carrier and a pharmaceutically effective antiviral amount of a compound of claim 2.

31. A pharmaceutical composition comprising a pharmaceutically acceptable carrier and a pharmaceutically effective antiviral amount of a compound of claim 3.

32. A pharmaceutical composition comprising a pharmaceutically acceptable carrier and a pharmaceutically effective antiviral amount of a compound of claim 4.

33. A pharmaceutical composition comprising a pharmaceutically acceptable carrier and a pharmaceutically effective antiviral amount of a compound of claim 5.

34. A pharmaceutical composition comprising a pharmaceutically acceptable carrier and a pharmaceutically effective antiviral amount of a compound of claim 6.

35. A pharmaceutical composition comprising a pharmaceutically acceptable carrier and a pharmaceutically effective antiviral amount of a compound of claim 7.

36. A pharmaceutical composition comprising a pharmaceutically acceptable carrier and a pharmaceutically effective antiviral amount of a compound of claim 8.

37. A pharmaceutical composition comprising a pharmaceutically acceptable carrier and a pharmaceutically effective antiviral amount of a compound of claim 9.

38. A pharmaceutical composition comprising a pharmaceutically acceptable carrier and a pharmaceutically effective antiviral amount of a compound of claim 10.

39. A pharmaceutical composition comprising a pharmaceutically acceptable carrier and a pharmaceutically effective antiviral amount of a compound of claim 11.

40. A pharmaceutical composition comprising a pharmaceutically acceptable carrier and a pharmaceutically effective antiviral amount of a compound of claim 12.

41. A pharmaceutical composition comprising a pharmaceutically acceptable carrier and a pharmaceutically effective antiviral amount of a compound of claim 13.

42. A pharmaceutical composition comprising a pharmaceutically acceptable carrier and a pharmaceutically effective antiviral amount of a compound of claim 14.

* * * * *